(12) United States Patent
Romero et al.

(10) Patent No.: US 11,827,922 B2
(45) Date of Patent: Nov. 28, 2023

(54) HIGH THROUGHPUT NUCLEIC ACID PROFILING OF SINGLE CELLS

(71) Applicant: WISCONSIN ALUMNI RESEARCH FOUNDATION, Madison, WI (US)

(72) Inventors: Philip Anthony Romero, Madison, WI (US); Leland Bradford Hyman, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 292 days.

(21) Appl. No.: 16/978,027

(22) PCT Filed: Mar. 6, 2019

(86) PCT No.: PCT/US2019/020926
§ 371 (c)(1),
(2) Date: Sep. 3, 2020

(87) PCT Pub. No.: WO2019/173460
PCT Pub. Date: Sep. 12, 2019

(65) Prior Publication Data
US 2021/0363573 A1 Nov. 25, 2021
US 2022/0081711 A9 Mar. 17, 2022

Related U.S. Application Data

(60) Provisional application No. 62/639,822, filed on Mar. 7, 2018.

(51) Int. Cl.
| | | |
|---|---|---|
| C12Q 1/68 | (2018.01) | |
| C12Q 1/6844 | (2018.01) | |
| G02B 27/01 | (2006.01) | |
| G06T 19/00 | (2011.01) | |
| G02F 1/1335 | (2006.01) | |
| G02F 1/13363 | (2006.01) | |

(52) U.S. Cl.
CPC ....... *C12Q 1/6844* (2013.01); *G02B 27/0172* (2013.01); *G06T 19/006* (2013.01); *G02F 1/13363* (2013.01); *G02F 1/133526* (2013.01)

(58) Field of Classification Search
None
See application file for complete search history.

(56) References Cited

U.S. PATENT DOCUMENTS

| | | | |
|---|---|---|---|
| 2007/0072215 A1 | 3/2007 | Seelig et al. | |
| 2009/0042737 A1 | 2/2009 | Katz et al. | |
| 2011/0294687 A1* | 12/2011 | Kleinbaum | C12Q 1/6837 506/9 |
| 2015/0132743 A1 | 5/2015 | Egidio et al. | |
| 2016/0266105 A1 | 9/2016 | Ismagilov et al. | |
| 2017/0009274 A1 | 1/2017 | Abate et al. | |
| 2017/0369921 A1 | 12/2017 | Tan et al. | |

FOREIGN PATENT DOCUMENTS

| | | | |
|---|---|---|---|
| WO | WO-2015200717 A2 * | 12/2015 | ............ C12Q 1/686 |
| WO | WO 2017/141068 A1 | 8/2017 | |
| WO | WO 2019/136058 A1 | 7/2019 | |

OTHER PUBLICATIONS

Arezi B, McCarthy M, Hogrefe H. Mutant of Moloney murine leukemia Virus reverse transcriptase exhibits higher resistance to common RT-qPCR inhibitors. Anal Biochem. May 15, 2010;400(2):301-3.

Baccouche, A., Montagne, K., Padirac, A., Fujii, T., Rondelez, Y., Dynamic DNA-toolbox reaction circuits: A walkthrough. *Methods.* 2014. 67(2), 234-249.

Badolo, A., Okado, K., Guelbeogo, W. M., Aonuma, H., Bando, H., Fukumoto, S., Sagnon, N., Kanuka, H. Development of an allele-specific, loop-mediated, isothermal amplification method (AS-LAMP) to detect the L1014F kdr-w mutation in *Anopheles gambiae s. l. Malaria Journal.* 2012. 11(227), 1-7.

Bendall SC, Nolan GP. From single cells to deep phenotypes in cancer. Nat Biotechnol. Jul. 10, 2012;30(7):639-47.

Chen, Y., Song, Y., Wu, F., Liu, W., Fu, B., Feng, B., Zhou, X. A DNA logic gate based on strand displacement reaction and rolling circle amplification, responding to multiple low-abundance DNA fragment input signals, and its application in detecting miRNAs. *Chemical Communications.* 2015. 51. 6980-6983.

Deng, W., Xu, H., Ding, W., Liang, H. DNA Logic Gate Based on Metallo-Toehold Strand Displacement. *PLOS One.* 2014. 9(11), e111650.

Eastburn DJ, Sciambi A, Abate AR. Ultrahigh-throughput Mammalian single-cell reverse-transcriptase polymerase chain reaction in microfluidic drops. Anal Chem. Aug. 20, 2013;85(16):8016-21.

Guo MT, Rotem A, Heyman JA, Weitz DA. Droplet microfluidics for high-throughput biological assays. Lab Chip. Jun. 21, 2012;12(12):2146-55.

Hedman J, Rådström P. Overcoming inhibition in real-time diagnostic PCR. Methods Mol Biol. 2013;943:17-48.

(Continued)

*Primary Examiner* — Samuel C Woolwine
*Assistant Examiner* — Olayinka A Oyeyemi
(74) *Attorney, Agent, or Firm* — Daniel A. Blasiole; DeWitt LLP

(57) ABSTRACT

Methods of profiling the nucleic acid composition of single cells and tools for same. The methods can include isolating a single cell in a liquid droplet, lysing the single cell in the liquid droplet to release template nucleic acid from the cell, amplifying the template nucleic acid in the liquid droplet to generate amplified nucleic acid, and detecting the amplified nucleic acid in the liquid droplet. The methods can be useful for profiling expression patterns and/or detecting genetic characteristics such as single nucleotide polymorphisms. The tools include nucleic acid logic gates, including polymerase-dependent logic gates. The logic gates can perform logical operations such as YES, NOT, AND, OR, AND-NOT, NOT-AND, NOT-OR, EXCLUSIVE-OR, EXCLUSIVE-NOR, and IMPLY. The tools also include microfluidic systems for performing the methods.

20 Claims, 24 Drawing Sheets
(23 of 24 Drawing Sheet(s) Filed in Color)
Specification includes a Sequence Listing.

(56) References Cited

OTHER PUBLICATIONS

Hyman, Leland B., Single-cell nucleic acid profiling in droplets (SNAPD) enables high-throughput analysis of heterogeneous cell populations. Nucleic Acids Research, 2021, vol. 49(18): 1-14.
International Search Report and Written Opinion for PCT Application No. PCT/US2019/020926 dated May 13, 2019.
Jang, Minjeong et al. Droplet-based Digital PCR System for Detection of Single-cell Level of Foodborne Pathogens. BioChip J. (2017) 11(4): 329-337.
Kalisky T, Blainey P, Quake SR. Genomic analysis at the single-cell level. Annu Rev Genet. 2011;45:431-45.
Kalisky T, Quake SR. Single-cell genomics. Nat Methods. Apr. 8, 2011(4):311-4.
Levsky JM, Singer RH. Gene expression and the myth of the average cell. Trends Cell Biol. Jan. 2003;13(1):4-6.
Li X, Ding T, Sun L, Mao C. Ultrasensitive DNA detection by cycle isothermal amplification based on nicking endonuclease and its application to logic gates. Biosens Bioelectron. Dec. 15, 2011:30(1):241-8.
Li W, Yang Y, Yan H, Liu Y. Three-input majority logic gate and multiple input logic circuit based on DNA strand displacement. Nano Lett. Jun. 12, 2013;13(6):2980-8.
Li W, Zhang F, Yan H, Liu Y. DNA based arithmetic function: a half adder based on DNA strand displacement. Nanoscale. Feb. 14, 2016:8(6):3775-84.
Ma, Yu-Dong et al. A microfluidic chip capable of generating and trapping emulsion droplets for digital loop-mediated isothermal amplifi analysis. Lab Chin (2018) 18:296-303.
Mary P, Dauphinot L, Bois N, Potier MC, Studer V, Tabeling P. Analysis of gene expression at the single-cell level using microdroplet-based microfluidic technology. Biomicrofluidics. Jun. 2011;5(2):24109.
Massey M, Medintz IL, Ancona MG, Algar WR. Time-Gated FRET and DNA-Based Photonic Molecular Logic Gates: AND, OR, NAND, and NOR. ACS Sens. Aug. 25. 2017:2(8):1205-1214.
Novak R, Zeng Y, Shuga J, Venugopalan G, Fletcher DA, Smith MT, Mathies RA. Single-cell multiplex gene detection and sequencing with microfluidically generated agarose emulsions. Angew Chem Int Ed Engl. Jan. 10, 2011:50(2):390-5.
Okamoto, A., Tanaka, K., Saito, I. DNA Logic Gates. *Journal of the American Chemical Society*. 2004. 126. 9458-9463.
Qian L, Winfree E. A simple DNA gate motif for synthesizing large-scale circuits. J R Soc Interface. Sep. 7, 2011;8(62):1281-97.
Qian L, Winfree E, Bruck J. Neural network computation with DNA strand displacement cascades. Nature. Jul. 20, 2011;475(7356):368-72.
Rane, Tushar D. et al. Microfluidic Continuous Flow Digital Loop-Mediated Isothermal Amplification (LAMP). Lab Chip. (2015); 15(3):776-782.
Ravan H, Amandadi M, Esmaeili-Mahani S. DNA Domino-Based Nanoscale Logic Circuit: A Versatile Strategy for Ultrasensitive Multiplexed Analysis of Nucleic Acids. Anal Chem. Jun. 6, 2017;89(11):6021-6028.
Sciarnbi A, Abate AR. Accurate microfluidic sorting of droplets at 30 kHz. Lab Chip. Oct. 22, 2015:15:47-51.
Sieuwerts AM, Mostert B, Bolt-de Vries J, Peeters D, de Jongh FE, Stouthard J M, Dirix LY, van Dam PA, Van Galen A, de Weerd V, Kraan J, van der Spoel P, Ramírez-Moreno R, van Deurzen CH, Smid M, Yu JX, Jiang J, Wang Y, Gratama JW, Sleijfer S, Foekens JA, Martens JW. mRNA and microRNA expression profiles in circulating tumor cells and primary tumors of metastatic breast cancer patients. Clin Cancer Res. Jun. 1, 2011;17(11):3600-18.

Supplementary Search Report on European Application No. 197651169 dated Oct. 21, 2021.
Tanner, N. A., Zhang, Y., Evans, Jr., T. C. Simultaneous multiple target detection in real-time loop-mediated isothermal amplification. *BioTechniques*. 2012. 53. 81-89.
Teh SY, Lin R, Hung LH, Lee AP. Droplet microfluidics. Lab Chip. Feb. 2008;8(2):198-220.
Thubagere AJ, Thachuk C, Berleant J, Johnson RF, Ardelean DA, Cherry KM, Qian L. Compiler-aided systematic construction of large-scale DNA strand displacement circuits using unpurified components. Nat Commun. Feb. 23, 2017;8:14373.
University of Washington Computer Science & Engineering. Moduel 5: Logic circuits with DNA strand displacement (part 1). Presentation. 2014.
Vyawahare S, Griffiths AD, Merten CA. Miniaturization and parallelization of biological and chemical assays in microfluidic devices. Chem Biol. Oct. 29, 2010;17(10):1052-65.
Wang, Y., Zhang, W., Li, X., Cui, G. Molecular Logic Gates Based on Localized DNA Strand Displacement. *Journal of Computational and Theoretical Nanoscience*. 2016. 13. 1-5.
Wei H, Hu B, Tang S, Zhao G, Guan Y. Repressor logic modules assembled by rolling circle amplification platform to construct a set of logic gates. Sci Rep. Nov. 21, 2016;6:37477.
White AK, VanInsberghe M, Petriv OI, Hamidi M, Sikorski D, Marra MA, Piret J, Aparicio S, Hansen CL. High-throughput microfluidic single-cell RT-qPCR. Proc Natl Acad Sci U S A. Aug. 23, 2011;108(34):13999-4004.
Xu W, Deng R, Wang L, Li J. Multiresponsive rolling circle amplification for DNA logic gates mediated by endonuclease. Anal Chem. Aug. 5, 2014;86(15):7813-8.
Yang J, Shen L, Ma J, Schlaberg HI, Liu S, Xu J, Zhang C. Fluorescent nanoparticle beacon for logic gate operation regulated by strand displacement. ACS Appl Mater Interfaces. Jun. 26, 2013:5(12):5392-6.
Yang J, Song Z, Liu S, Zhang Q, Zhang C. Dynamically Arranging Gold Nanoparticles on DNA Origami for Molecular Logic Gates. ACS Appl Mater Interfaces. Aug. 31, 2016;8(34):22451-6.
Yang B, Zhang XB, Kang LP, Huang ZM, Shen GL, Yu RQ, Tan W. Intelligent layered nanoflare: "lab-on-a-nanoparticle" for multiple DNA logic gate operations and efficient intracellular delivery. Nanoscale. Aug. 7, 2014;6(15):8990-6.
Yao D, Wang B, Xiao S, Song T, Huang F, Liang H. What Controls the "Off/On Switch" in the Toehold-Mediated Strand Displacement Reaction on DNA Conjugated Gold Nanoparticles? Langmuir. Jun. 30, 2015;31(25):7055-61.
Yongkiettrakul, S., Kampeera, J ., Chareanchim, W., Rattanajak, R., Pomthanakasem, W., Kiatpathomchai, W., Kongkasuriyachai, D. Simple detection of single nucleotide polymorphism in *Plasmodium falciparum* by SNP-LAMP assay combined with lateral flow dipstick. *Parasitology International*. 2017. 66. 964-971.
Zanoli LM, Spoto G. Isothermal amplification methods for the detection of nucleic acids in microfluidic devices. Biosensors (Basel). Dec. 27, 2012;3(1):18-43.Zhang C, Yang J, Xu J. Circular DNA logic gates with strand displacement. Langmuir. Feb. 2. 2010;26(3):1416-9.
Zhang H, Jenkins G, Zou Y, Zhu Z, Yang CJ. Massively parallel single-molecule and single-cell emulsion reverse transcription polymerase chain reaction using agarose droplet microfluidics. Anal Chem. Apr. 17, 2012;84(8):3599-606.
Zhu J, Zhang L, Dong S, Wang E. Four-way junction-driven DNA strand displacement and its application in building majority logic circuit. ACS Nano. Nov. 26, 2013;7(11):10211-7.
Zou C, Wei X, Zhang Z, Liu C, Zhou C, Liu Y. Four-Analog Computation Based on DNA Strand Displacement. ACS Omega 2017 2 (8), 4143-4160.

* cited by examiner

Waste Outlet

Sorted Outlet

SEQUENCE LISTING

```
<160> NUMBER OF SEQ ID NOS: 73

<210> SEQ ID NO 1
<211> LENGTH: 1921
<212> TYPE: DNA
<213> ORGANISM: Homo sapiens

<400> SEQUENCE: 1
gagtgagcgg cgcggggcca atcagcgtgc gccgttccga aagttgcctt ttatggctcg      60
agcggccgcg gcggcgccct ataaaaccca gcggcgcgac gcgccaccac cgccgagacc     120
gcgtccgccc cgcgagcaca gagcctcgcc tttgccgatc cgccgcccgt ccacacccgc     180
cgccagctca ccatggatga tgatatcgcc gcgctcgtcg tcgacaacgg ctccggcatg     240
tgcaaggccg gcttcgcggg cgacgatgcc ccccgggccg tcttcccctc catcgtgggg     300
cgccccaggc accaggcgt gatggtgggc atgggtcaga aggattccta tgtgggcgac     360
gaggcccaga gcaagagagg catcctcacc ctgaagtacc ccatcgagca cggcatcgtc     420
accaactggg acgacatgga gaaatctgg caccacacct tctacaatga gctgcgtgtg     480
gctcccgagg agcacccgt gctgctgacc gaggccccc tgaaccccaa ggccaaccgc     540
gagaagatga cccagatcat gtttgagacc ttcaacaccc cagccatgta cgttgctatc     600
caggctgtgc tatccctgta cgcctctggc cgtaccactg gcatcgtgat ggactccggt     660
gacggggtca cccacactgt gcccatctac gaggggtatg ccctccccca tgccatcctg     720
cgtctggacc tggctggccg ggacctgact gactacctca tgaagatcct caccgagcgc     780
ggctacagct tcaccaccac ggccgagcgg gaaatcgtgc gtgacattaa ggagaagctg     840
```

```
tgctacgtcg ccctggactt cgagcaagag atggccacgg ctgcttccag ctcctccctg    900
gagaagagct acgagctgcc tgacggccag gtcatcacca ttggcaatga gcggttccgc    960
tgccctgagg cactcttcca gccttccttc ctgggcatgg agtcctgtgg catccacgaa   1020
actaccttca actccatcat gaagtgtgac gtggacatcc gcaaagacct gtacgccaac   1080
acagtgctgt ctggcggcac caccatgtac cctggcattg ccgacaggat gcagaaggag   1140
atcactgccc tggcacccag cacaatgaag atcaagatca ttgctcctcc tgagcgcaag   1200
tactccgtgt ggatcggcgg ctccatcctg gcctcgctgt ccaccttcca gcagatgtgg   1260
atcagcaagc aggagtatga cgagtccggc ccctccatcg tccaccgcaa atgcttctag   1320
gcggactatg acttagttgc gttacaccct tcttgacaa acctaactt gcgcagaaaa    1380 caagatgaga ttggcatggc tttatttgtt ttttttgttt tgttttggtt ttttttttt    1440 ttttggcttg actcaggatt taaaaactgg aacggtgaag gtgacagcag tcggttggag   1500
cgagcatccc ccaaagttca caatgtggcc gaggactttg attgcacatt gttgtttttt   1560
taatagtcat tccaaatatg agatgcgttg ttacaggaag tcccttgcca tcctaaaagc   1620 cacccccactt ctctctaagg agaatggccc agtcctctcc caagtccaca caggggaggt   1680
gatagcattg ctttcgtgta aattatgtaa tgcaaaattt ttttaatctt cgccttaata   1740
cttttttatt ttgttttatt ttgaatgatg agccttcgtg cccccccttc cccctttttt   1800
gtcccccaac ttgagatgta tgaaggcttt tggtctccct gggagtgggt ggaggcagcc   1860
agggcttacc tgtacactga cttgagacca gttgaataaa agtgcacacc ttaaaaatga   1920
g                                                                  1921

<210> SEQ ID NO 2
<211> LENGTH: 1921
<212> TYPE: DNA
<213> ORGANISM: Homo sapiens

<400> SEQUENCE: 2
gagtgagcgg cgcggggcca atcagcgtgc gccgttccga aagttgcctt ttatggctcg    60
agcggccgcg gcggcgccct ataaaaccca gcggcgcgac gcgccaccac cgccgagacc   120
gcgtccgccc cgcgagcaca gagcctcgcc tttgccgatc cgccgcccgt ccacacccgc   180
cgccagctca ccatggatga tgatatcgcc gcgctcgtcg tcgacaacgg ctccggcatg   240
tgcaaggccg gcttcgcggg cgacgatgcc ccccgggccg tcttcccctc catcgtgggg   300
cgccccaggc accagggcgt gatggtgggc atgggtcaga aggattccta tgtgggcgac   360
gaggcccaga gcaagagagg catcctcacc ctgaagtacc ccatcgagca cggcatcgtc   420
accaactggg acgacatgga aaaatctgg caccacacct tctacaatga gctgcgtgtg   480
gctcccgagg agcaccccgt gctgctgacc gaggcccccc tgaaccccaa ggccaaccgc   540
gagaagatga cccagatcat gtttgagacc ttcaacaccc cagccatgta cgttgctatc   600
caggctgtgc tatccctgta cgcctctggc cgtaccactg gcatcgtgat ggactccggt   660
gacggggtca cccacactgt gcccatctac gaggggtatg ccctccccca tgccatcctg   720
cgtctggacc tggctggccg ggacctgact gactacctca tgaagatcct caccgagcgc   780
ggctacagct tcaccaccac ggccgagcgg gaaatcgtgc gtgacattaa ggagaagctg   840
tgctacgtcg ccctggactt cgagcaagag atggccacgg ctgcttccag ctcctccctg    900
gagaagagct acgagctgcc tgacggccag gtcatcacca ttggcaatga gcggttccgc    960
```

-continued

```
tgccctgcgg cactcttcca gccttccttc ctgggcatgg agtcctgtgg catccacgaa    1020
actaccttca actccatcat gaagtgtgac gtggacatcc gcaaagacct gtacgccaac    1080
acagtgctgt ctggcggcac caccatgtac cctggcattg ccgacaggat gcagaaggag    1140
atcactgccc tggcacccag cacaatgaag atcaagatca ttgctcctcc tgagcgcaag    1200
tactccgtgt ggatcggcgg ctccatcctg gcctcgctgt ccaccttcca gcagatgtgg    1260
atcagcaagc aggagtatga cgagtccggc ccctccatcg tccaccgcaa atgcttctag    1320
gcggactatg acttagttgc gttacaccct ttcttgacaa aacctaactt gcgcagaaaa    1380
caagatgaga ttggcatggc tttatttgtt ttttttgttt tgttttggtt ttttttttt     1440 ttttggcttg actcaggatt taaaaactgg aacggtgaag gtgacagcag tcggttggag    1500
cgagcatccc ccaaagttca caatgtggcc gaggactttg attgcacatt gttgtttttt    1560
taatagtcat tccaaatatg agatgcgttg ttacaggaag tcccttgcca tcctaaaagc    1620 cacccccactt ctctctaagg agaatggccc agtcctctcc caagtccaca caggggaggt    1680
gatagcattg ctttcgtgta aattatgtaa tgcaaaattt ttttaatctt cgccttaata    1740
cttttttatt ttgttttatt ttgaatgatg agccttcgtg ccccccttc cccctttttt     1800 gtcccccaac ttgagatgta tgaaggcttt tggtctccct gggagtgggt ggaggcagcc    1860
agggcttacc tgtacactga cttgagacca gttgaataaa agtgcacacc ttaaaaatga    1920
g                                                                     1921
```

```
<210> SEQ ID NO 3
<211> LENGTH: 19
<212> TYPE: DNA
<213> ORGANISM: Artificial Sequence
<220> FEATURE:
<223> OTHER INFORMATION: Primer KRT19 LAMP-3 F3

<400> SEQUENCE: 3
agtgacatgc gaagccaat                                                    19

<210> SEQ ID NO 4
<211> LENGTH: 20
<212> TYPE: DNA
<213> ORGANISM: Artificial Sequence
<220> FEATURE:
<223> OTHER INFORMATION: Primer KRT19 LAMP-3 B3

<400> SEQUENCE: 4
gctttcatgc tcagctgtga                                                   20

<210> SEQ ID NO 5
<211> LENGTH: 41
<212> TYPE: DNA
<213> ORGANISM: Artificial Sequence
<220> FEATURE:
<223> OTHER INFORMATION: Primer KRT19 LAMP-3 FIP

<400> SEQUENCE: 5
agcgacctcc cggttcaatt ctcgagcaga accggaagga t                           41

<210> SEQ ID NO 6
<211> LENGTH: 41
<212> TYPE: DNA
<213> ORGANISM: Artificial Sequence
<220> FEATURE:
<223> OTHER INFORMATION: KRT19 LAMP-3 BIP

<400> SEQUENCE: 6
```
cacacggagc agctccagat gtgcagctca atctcaagac c                41

<210> SEQ ID NO 7
<211> LENGTH: 19
<212> TYPE: DNA
<213> ORGANISM: Artificial Sequence
<220> FEATURE:
<223> OTHER INFORMATION: Primer KRT19 LAMP-3 LF

<400> SEQUENCE: 7
tggtgaacca ggcttcagc                                         19

<210> SEQ ID NO 8
<211> LENGTH: 22
<212> TYPE: DNA
<213> ORGANISM: Artificial Sequence
<220> FEATURE:
<223> OTHER INFORMATION: Primer KRT19 LAMP-3 LB

<400> SEQUENCE: 8
aggtccgagg ttactgacct gc                                     22

<210> SEQ ID NO 9
<211> LENGTH: 17
<212> TYPE: DNA
<213> ORGANISM: Artificial Sequence
<220> FEATURE:
<223> OTHER INFORMATION: Primer VIM LAMP-2 F3

<400> SEQUENCE: 9
ccgcaccaac gagaagg                                           17

<210> SEQ ID NO 10
<211> LENGTH: 18
<212> TYPE: DNA
<213> ORGANISM: Artificial Sequence
<220> FEATURE:
<223> OTHER INFORMATION: Primer VIM LAMP-2 B3

<400> SEQUENCE: 10
tggttagctg gtccacct                                          18

<210> SEQ ID NO 11
<211> LENGTH: 38
<212> TYPE: DNA
<213> ORGANISM: Artificial Sequence
<220> FEATURE:
<223> OTHER INFORMATION: Primer VIM LAMP-2 FIP

<400> SEQUENCE: 11
tccaggaagc gcaccttgtc ggagctgcag gagctgaa                    38

<210> SEQ ID NO 12
<211> LENGTH: 40
<212> TYPE: DNA
<213> ORGANISM: Artificial Sequence
<220> FEATURE:
<223> OTHER INFORMATION: Primer VIM LAMP-2 BIP

<400> SEQUENCE: 12
aagatcctgc tggccgagct cccgcatctc ctcctcgtag                  40

<210> SEQ ID NO 13
<211> LENGTH: 17
<212> TYPE: DNA

```
<213> ORGANISM: Artificial Sequence
<220> FEATURE:
<223> OTHER INFORMATION: Primer VIM LAMP-2 LF

<400> SEQUENCE: 13
agttggcgaa gcggtca                                                    17

<210> SEQ ID NO 14
<211> LENGTH: 20
<212> TYPE: DNA
<213> ORGANISM: Artificial Sequence
<220> FEATURE:
<223> OTHER INFORMATION: Primer VIM LAMP-2 LB

<400> SEQUENCE: 14
cagctcaagg gccaaggcaa                                                 20

<210> SEQ ID NO 15
<211> LENGTH: 18
<212> TYPE: DNA
<213> ORGANISM: Artificial Sequence
<220> FEATURE:
<223> OTHER INFORMATION: Primer ESR1 LAMP-1 F3

<400> SEQUENCE: 15
agagctgcca acctttgg                                                   18

<210> SEQ ID NO 16
<211> LENGTH: 19
<212> TYPE: DNA
<213> ORGANISM: Artificial Sequence
<220> FEATURE:
<223> OTHER INFORMATION: Primer ESR1 LAMP-1 B3

<400> SEQUENCE: 16
tgaaccagct ccctgtctg                                                  19

<210> SEQ ID NO 17
<211> LENGTH: 40
<212> TYPE: DNA
<213> ORGANISM: Artificial Sequence
<220> FEATURE:
<223> OTHER INFORMATION: Primer ESR1 LAMP-1 FIP

<400> SEQUENCE: 17
ggcactgacc atctggtcgg aagcccgctc atgatcaaac                           40

<210> SEQ ID NO 18
<211> LENGTH: 40
<212> TYPE: DNA
<213> ORGANISM: Artificial Sequence
<220> FEATURE:
<223> OTHER INFORMATION: Primer ESR1 LAMP-1 BIP

<400> SEQUENCE: 18
ttgttggatg ctgagccccc cccatcatcg aagcttcact                           40

<210> SEQ ID NO 19
<211> LENGTH: 22
<212> TYPE: DNA
<213> ORGANISM: Artificial Sequence
<220> FEATURE:
<223> OTHER INFORMATION: Primer ESR1 LAMP-1 LF

<400> SEQUENCE: 19
gccaggctgt tcttcttaga gc                                              22
```

<210> SEQ ID NO 20
<211> LENGTH: 25
<212> TYPE: DNA
<213> ORGANISM: Artificial Sequence
<220> FEATURE:
<223> OTHER INFORMATION: Primer ESR1 LAMP-1 LB

<400> SEQUENCE: 20
actctattcc gagtatgatc ctacc                               25

<210> SEQ ID NO 21
<211> LENGTH: 16
<212> TYPE: DNA
<213> ORGANISM: Artificial Sequence
<220> FEATURE:
<223> OTHER INFORMATION: Primer GAPDH LAMP-2 F3

<400> SEQUENCE: 21
gctgccaagg ctgtgg                                         16

<210> SEQ ID NO 22
<211> LENGTH: 18
<212> TYPE: DNA
<213> ORGANISM: Artificial Sequence
<220> FEATURE:
<223> OTHER INFORMATION: Primer GAPDH LAMP-2 B3

<400> SEQUENCE: 22
cccaggatgc ccttgagg                                       18

<210> SEQ ID NO 23
<211> LENGTH: 41
<212> TYPE: DNA
<213> ORGANISM: Artificial Sequence
<220> FEATURE:
<223> OTHER INFORMATION: Primer GAPDH LAMP-2 FIP

<400> SEQUENCE: 23
gttggcagtg gggacacgga acaaggtcat ccctgagctg a             41

<210> SEQ ID NO 24
<211> LENGTH: 38
<212> TYPE: DNA
<213> ORGANISM: Artificial Sequence
<220> FEATURE:
<223> OTHER INFORMATION: Primer GAPDH LAMP-2 BIP

<400> SEQUENCE: 24
tgtcagtggt ggacctgacc tgtccgacgc ctgcttca                 38

<210> SEQ ID NO 25
<211> LENGTH: 18
<212> TYPE: DNA
<213> ORGANISM: Artificial Sequence
<220> FEATURE:
<223> OTHER INFORMATION: Primer GAPDH LAMP-2 LF

<400> SEQUENCE: 25
ggccatgcca gtgagctt                                       18

<210> SEQ ID NO 26
<211> LENGTH: 25
<212> TYPE: DNA
<213> ORGANISM: Artificial Sequence
<220> FEATURE:

<223> OTHER INFORMATION: Primer GAPDH LAMP-2 LB

<400> SEQUENCE: 26
cgtctagaaa aacctgccaa atatg                                              25

<210> SEQ ID NO 27
<211> LENGTH: 17
<212> TYPE: DNA
<213> ORGANISM: Artificial Sequence
<220> FEATURE:
<223> OTHER INFORMATION: Primer ACTB 4 B3-SNP

<400> SEQUENCE: 27
ggctggaaga gtgccgc                                                       17

<210> SEQ ID NO 28
<211> LENGTH: 18
<212> TYPE: DNA
<213> ORGANISM: Artificial Sequence
<220> FEATURE:
<223> OTHER INFORMATION: Primer ACTB 4 F3

<400> SEQUENCE: 28
gcggctacag cttcacca                                                      18

<210> SEQ ID NO 29
<211> LENGTH: 42
<212> TYPE: DNA
<213> ORGANISM: Artificial Sequence
<220> FEATURE:
<223> OTHER INFORMATION: Primer ACTB 4 FIP

<400> SEQUENCE: 29
cgtggccatc tcttgctcga aggggaaatc gtgcgtgaca tt                           42

<210> SEQ ID NO 30
<211> LENGTH: 38
<212> TYPE: DNA
<213> ORGANISM: Artificial Sequence
<220> FEATURE:
<223> OTHER INFORMATION: Primer ACTB 4 BIP

<400> SEQUENCE: 30
gcttccagct cctccctgga ccgctcattg ccaatggt                                38

<210> SEQ ID NO 31
<211> LENGTH: 20
<212> TYPE: DNA
<213> ORGANISM: Artificial Sequence
<220> FEATURE:
<223> OTHER INFORMATION: Primer ACTB 4 LF

<400> SEQUENCE: 31
acgtagcaca gcttctcctt                                                    20

<210> SEQ ID NO 32
<211> LENGTH: 19
<212> TYPE: DNA
<213> ORGANISM: Artificial Sequence
<220> FEATURE:
<223> OTHER INFORMATION: Primer ACTB 4 LB

<400> SEQUENCE: 32
gaagagctac gagctgcct                                                     19

```
<210> SEQ ID NO 33
<211> LENGTH: 17
<212> TYPE: DNA
<213> ORGANISM: Artificial Sequence
<220> FEATURE:
<223> OTHER INFORMATION: Primer ACTB 4 B3-Sink

<400> SEQUENCE: 33
gcggcactct tccagcc                                                    17

<210> SEQ ID NO 34
<211> LENGTH: 30
<212> TYPE: DNA
<213> ORGANISM: Artificial Sequence
<220> FEATURE:
<223> OTHER INFORMATION: Reporter RepF

<400> SEQUENCE: 34
cgagtgctgc gtatgacaag ggctagcgtt                                      30

<210> SEQ ID NO 35
<211> LENGTH: 30
<212> TYPE: DNA
<213> ORGANISM: Artificial Sequence
<220> FEATURE:
<223> OTHER INFORMATION: Reporter RepF-HEX

<400> SEQUENCE: 35
cgagtgctgc gtatgacaag ggctagcgtt                                      30

<210> SEQ ID NO 36
<211> LENGTH: 22
<212> TYPE: DNA
<213> ORGANISM: Artificial Sequence
<220> FEATURE:
<223> OTHER INFORMATION: Reporter RepQ

<400> SEQUENCE: 36
cccttgtcat acgcagcact cg                                              22

<210> SEQ ID NO 37
<211> LENGTH: 30
<212> TYPE: DNA
<213> ORGANISM: Artificial Sequence
<220> FEATURE:
<223> OTHER INFORMATION: Reporter RepF2-AF647

<400> SEQUENCE: 37
cgccgcgtcc tgatctaact gactgactgc                                      30

<210> SEQ ID NO 38
<211> LENGTH: 22
<212> TYPE: DNA
<213> ORGANISM: Artificial Sequence
<220> FEATURE:
<223> OTHER INFORMATION: Reporter RepQ2

<400> SEQUENCE: 38
tcagttagat caggacgcgg cg                                              22

<210> SEQ ID NO 39
<211> LENGTH: 60
<212> TYPE: DNA
<213> ORGANISM: Artificial Sequence
<220> FEATURE:
<223> OTHER INFORMATION: KRT19 -> Rep Transducer Gate
```

```
<400> SEQUENCE: 39
cgagtgctgc gtatgacaag ggctagcgtt atgctacgag cgacctcccg gttcaattct    60

<210> SEQ ID NO 40
<211> LENGTH: 30
<212> TYPE: DNA
<213> ORGANISM: Artificial Sequence
<220> FEATURE:
<223> OTHER INFORMATION: KRT19 -> Rep Transducer Output

<400> SEQUENCE: 40
aacgctagcc cttgtcatac gcagcactcg                                     30

<210> SEQ ID NO 41
<211> LENGTH: 58
<212> TYPE: DNA
<213> ORGANISM: Artificial Sequence
<220> FEATURE:
<223> OTHER INFORMATION: VIM -> Rep Transducer Gate

<400> SEQUENCE: 41
cgagtgctgc gtatgacaag ggctagcgtt atgctacgtc caggaagcgc accttgtc     58

<210> SEQ ID NO 42
<211> LENGTH: 30
<212> TYPE: DNA
<213> ORGANISM: Artificial Sequence
<220> FEATURE:
<223> OTHER INFORMATION: VIM -> Rep Transducer Output

<400> SEQUENCE: 42
aacgctagcc cttgtcatac gcagcactcg                                     30

<210> SEQ ID NO 43
<211> LENGTH: 88
<212> TYPE: DNA
<213> ORGANISM: Artificial Sequence
<220> FEATURE:
<223> OTHER INFORMATION: KRT19 AND VIM Strand 1

<400> SEQUENCE: 43
cgagtgctgc gtatgacaag ggctagcgtt atgctacgtc caggaagcgc accttgtcat    60
gctacgagcg acctcccggt tcaattct                                       88

<210> SEQ ID NO 44
<211> LENGTH: 88
<212> TYPE: DNA
<213> ORGANISM: Artificial Sequence
<220> FEATURE:
<223> OTHER INFORMATION: KRT19 AND VIM Strand 2

<400> SEQUENCE: 44
cgagtgctgc gtatgacaag ggctagcgtt atgctacgag cgacctcccg gttcaattct    60
atgctacgtc caggaagcgc accttgtc                                       88

<210> SEQ ID NO 45
<211> LENGTH: 88
<212> TYPE: DNA
<213> ORGANISM: Artificial Sequence
<220> FEATURE:
<223> OTHER INFORMATION: KRT19 OR VIM Gate

<400> SEQUENCE: 45
cgagtgctgc gtatgacaag ggctagcgtt atgctacgtc caggaagcgc accttgtcat    60
```

```
gctacgagcg acctcccggt tcaattct                                          88

<210> SEQ ID NO 46
<211> LENGTH: 30
<212> TYPE: DNA
<213> ORGANISM: Artificial Sequence
<220> FEATURE:
<223> OTHER INFORMATION: KRT19 OR VIM Output

<400> SEQUENCE: 46
aacgctagcc cttgtcatac gcagcactcg                                        30

<210> SEQ ID NO 47
<211> LENGTH: 20
<212> TYPE: DNA
<213> ORGANISM: Artificial Sequence
<220> FEATURE:
<223> OTHER INFORMATION: VIM F1

<400> SEQUENCE: 47
gacaaggtgc gcttcctgga                                                   20

<210> SEQ ID NO 48
<211> LENGTH: 22
<212> TYPE: DNA
<213> ORGANISM: Artificial Sequence
<220> FEATURE:
<223> OTHER INFORMATION: KRT19 F1

<400> SEQUENCE: 48
agaattgaac cgggaggtcg ct                                                22

<210> SEQ ID NO 49
<211> LENGTH: 60
<212> TYPE: DNA
<213> ORGANISM: Artificial Sequence
<220> FEATURE:
<223> OTHER INFORMATION: KRT19 Transducer 2 Gate

<400> SEQUENCE: 49
ctgctctcac ggaggcgcac cggtaagggt catcgatgag cgacctcccg gttcaattct       60

<210> SEQ ID NO 50
<211> LENGTH: 58
<212> TYPE: DNA
<213> ORGANISM: Artificial Sequence
<220> FEATURE:
<223> OTHER INFORMATION: VIM Transducer 2 Gate

<400> SEQUENCE: 50
ctgctctcac ggaggcgcac cggtaagggt catcgatgtc caggaagcgc accttgtc        58

<210> SEQ ID NO 51
<211> LENGTH: 35
<212> TYPE: DNA
<213> ORGANISM: Artificial Sequence
<220> FEATURE:
<223> OTHER INFORMATION: KRT19/VIM Transducer 2 Output

<400> SEQUENCE: 51
cgatgaccct taccggtgcg cctccgtgag agcag                                  35

<210> SEQ ID NO 52
<211> LENGTH: 45
<212> TYPE: DNA
```

<213> ORGANISM: Artificial Sequence
<220> FEATURE:
<223> OTHER INFORMATION: KRT19 AND VIM Gate

<400> SEQUENCE: 52
cgagtgctgc gtatgacaag ggctagcgtt atgctgctct cacgg        45

<210> SEQ ID NO 53
<211> LENGTH: 30
<212> TYPE: DNA
<213> ORGANISM: Artificial Sequence
<220> FEATURE:
<223> OTHER INFORMATION: KRT19 AND VIM Out

<400> SEQUENCE: 53
aacgctagcc cttgtcatac gcagcactcg        30

<210> SEQ ID NO 54
<211> LENGTH: 50
<212> TYPE: DNA
<213> ORGANISM: Artificial Sequence
<220> FEATURE:
<223> OTHER INFORMATION: KRT19 AND VIM Threshold

<400> SEQUENCE: 54
ccgctggtga tcactctgct ctcacggagg cgcaccggta agggtcatcg        50

<210> SEQ ID NO 55
<211> LENGTH: 60
<212> TYPE: DNA
<213> ORGANISM: Artificial Sequence
<220> FEATURE:
<223> OTHER INFORMATION: KRT19 Transducer 3 Gate

<400> SEQUENCE: 55
cgcgatccga gtgctgcgta tgacaagggc tagcgtttgc cggaagcgac ctcccggttc        60

<210> SEQ ID NO 56
<211> LENGTH: 60
<212> TYPE: DNA
<213> ORGANISM: Artificial Sequence
<220> FEATURE:
<223> OTHER INFORMATION: VIM Transducer 3 Gate

<400> SEQUENCE: 56
cgcgatccga gtgctgcgta tgacaagggc tagcgtttgc cggatccagg aagcgcacct        60

<210> SEQ ID NO 57
<211> LENGTH: 44
<212> TYPE: DNA
<213> ORGANISM: Artificial Sequence
<220> FEATURE:
<223> OTHER INFORMATION: KRT19/VIM Transducer 3 Output

<400> SEQUENCE: 57
tccggcaaac gctagccctt gtcatacgca gcactcggat cgcg        44

<210> SEQ ID NO 58
<211> LENGTH: 60
<212> TYPE: DNA
<213> ORGANISM: Artificial Sequence
<220> FEATURE:
<223> OTHER INFORMATION: VIM Transducer 4 Gate

<400> SEQUENCE: 58
ccatcgcgga gacacggaca tcgttaaggc agcctgtagg cagcctccag gaagcgcacc        60

<210> SEQ ID NO 59
<211> LENGTH: 60
<212> TYPE: DNA
<213> ORGANISM: Artificial Sequence
<220> FEATURE:
<223> OTHER INFORMATION: KRT19 Transducer 4 Gate

<400> SEQUENCE: 59
gtgtctccgc gatggcgagt gctgcgtatg acaagggcta gcgttagcga cctcccggtt    60

<210> SEQ ID NO 60
<211> LENGTH: 45
<212> TYPE: DNA
<213> ORGANISM: Artificial Sequence
<220> FEATURE:
<223> OTHER INFORMATION: KRT19 AND-NOT VIM Inhibitor

<400> SEQUENCE: 60
ggctgcctac aggctgcctt aacgatgtcc gtgtctccgc gatgg    45

<210> SEQ ID NO 61
<211> LENGTH: 45
<212> TYPE: DNA
<213> ORGANISM: Artificial Sequence
<220> FEATURE:
<223> OTHER INFORMATION: KRT19 AND-NOT VIM Output

<400> SEQUENCE: 61
aacgctagcc cttgtcatac gcagcactcg ccatcgcgga gacac    45

<210> SEQ ID NO 62
<211> LENGTH: 60
<212> TYPE: DNA
<213> ORGANISM: Artificial Sequence
<220> FEATURE:
<223> OTHER INFORMATION: KRT19 -> Rep2 Transducer Gate

<400> SEQUENCE: 62
gtgtctccgc gatggcgccg cgtcctgatc taactgactg actgcagcga cctcccggtt    60

<210> SEQ ID NO 63
<211> LENGTH: 45
<212> TYPE: DNA
<213> ORGANISM: Artificial Sequence
<220> FEATURE:
<223> OTHER INFORMATION: KRT19 -> Rep2 Transducer Output

<400> SEQUENCE: 63
gcagtcagtc agttagatca ggacgcggcg ccatcgcgga gacac    45

<210> SEQ ID NO 64
<211> LENGTH: 55
<212> TYPE: DNA
<213> ORGANISM: Artificial Sequence
<220> FEATURE:
<223> OTHER INFORMATION: CK19 Sensor

<400> SEQUENCE: 64
gagttaccag cctggagttc tcaatggtgg cctggtaact cactgaccga gctaa    55

<210> SEQ ID NO 65
<211> LENGTH: 67
<212> TYPE: DNA
<213> ORGANISM: Artificial Sequence
<220> FEATURE:

<223> OTHER INFORMATION: Oligo H1

<400> SEQUENCE: 65
cgacatctaa cctagctcac tgaccgagct aagctgttct cgattagctc ggtcagtgag    60
ttaccag                                                              67

<210> SEQ ID NO 66
<211> LENGTH: 46
<212> TYPE: DNA
<213> ORGANISM: Artificial Sequence
<220> FEATURE:
<223> OTHER INFORMATION: Oligo H2

<400> SEQUENCE: 66
gctgttctcg atcactgacc gagctaatcg agaacagctt agctcg                   46

<210> SEQ ID NO 67
<211> LENGTH: 67
<212> TYPE: DNA
<213> ORGANISM: Artificial Sequence
<220> FEATURE:
<223> OTHER INFORMATION: Oligo H3

<400> SEQUENCE: 67
gtcagtgagc taggttagat gtcgccatgt gtagacgaca tctaacctag cccttgtcat    60
agagcac                                                              67

<210> SEQ ID NO 68
<211> LENGTH: 46
<212> TYPE: DNA
<213> ORGANISM: Artificial Sequence
<220> FEATURE:
<223> OTHER INFORMATION: Oligo H4

<400> SEQUENCE: 68
agatgtcgtc tacacatggc gacatctaac ctagcccatg tgtaga                   46

<210> SEQ ID NO 69
<211> LENGTH: 27
<212> TYPE: DNA
<213> ORGANISM: Artificial Sequence
<220> FEATURE:
<223> OTHER INFORMATION: Oligo RepF-CHA

<400> SEQUENCE: 69
cgagtgctct atgacaaggg ctaggtt                                        27

<210> SEQ ID NO 70
<211> LENGTH: 20
<212> TYPE: DNA
<213> ORGANISM: Artificial Sequence
<220> FEATURE:
<223> OTHER INFORMATION: Oligo RepQ-CHA

<400> SEQUENCE: 70
cccttgtcat agagcactcg                                                20

<210> SEQ ID NO 71
<211> LENGTH: 21
<212> TYPE: DNA
<213> ORGANISM: Artificial Sequence
<220> FEATURE:
<223> OTHER INFORMATION: Oligo CK19 Input

<400> SEQUENCE: 71
gccaccattg agaactccag g     21

<210> SEQ ID NO 72
<211> LENGTH: 1496
<212> TYPE: DNA
<213> ORGANISM: Artificial Sequence
<220> FEATURE:
<223> OTHER INFORMATION: KRT19 gBlock

<400> SEQUENCE: 72

```
caggtctcgt atgagatatc cgccctgac accattcctc ccttccccc tccaccggcc      60
gcgggcataa aaggcgccag gtgagggcct cgccgctcct cccgcgaatc gcagcttctg    120
agaccagggt tgctccgtcc gtgctccgcc tcgccatgac ttcctacagc tatcgccagt    180
cgtcggccac gtcgtccttc ggaggcctgg gcggcggctc cgtgcgtttt gggccggggg    240
tcgcctttcg cgcgcccagc attcacgggg gctccggcgg ccgcggcgta tccgtgtcct    300
ccgcccgctt tgtgtcctcg tcctcctcgg gggcctacgg cggcggctac ggcggcgtcc    360
tgaccgcgtc cgacgggctg ctggcgggca acgagaagct aaccatgcag aacctcaacg    420
accgcctggc ctcctacctg gacaaggtgc gcgccctgga ggcggccaac ggcgagctag    480
aggtgaagat ccgcgactgg taccagaagc aggggcctgg gccctcccgc gactacagcc    540
actactacac gaccatccag gacctgcggg acaagattct tggtgccacc attgagaact    600
ccaggattgt cctgcagatc gacaatgccc gtctggctgc agatgacttc gaaccaagt     660
ttgagacgga acaggctctg cgcatgagcg tggaggccga catcaacggc ctgcgcaggg    720
tgctggatga gctgaccctg gccaggaccg acctggagat gcagatcgaa ggcctgaagg    780
aagagctggc ctacctgaag aagaaccatg aggaggaaat cagtacgctg aggggccaag    840
tgggaggcca ggtcagtgtg gaggtggatt ccgctccggg caccgatctc gccaagatcc    900
tgagtgacat gcgaagccaa tatgaggtca tggccgagca gaaccggaag gatgctgaag    960
cctggttcac cagccggact gaagaattga accgggaggt cgctggccac acggagcagc   1020
tccagatgag caggtccgag gttactgacc tgcggcgcac ccttcagggt cttgagattg   1080
agctgcagtc acagctgagc atgaaagctg ccttggaaga cacactggca gaaacggagg   1140
cgcgctttgg agcccagctg gcgcatatcc aggcgctgat cagcggtatt gaagcccagc   1200
tgggcgatgt gcgagctgat agtgagcggc agaatcagga gtaccagcgg ctcatggaca   1260
tcaagtcgcg gctggagcag gagattgcca cctaccgcag cctgctcgag ggacaggaag   1320
atcactacaa caatttgtct gcctccaagg tcctctgagg cagcaggctc tggggcttct   1380
gctgtccttt ggagggtgtc ttctgggtag agggatggga aggaagggac ccttacccc     1440
ggctcttctc ctgacctgcc aataaaaatt tatggtccaa gggtgagcga gaccac        1496
```

<210> SEQ ID NO 73
<211> LENGTH: 706
<212> TYPE: DNA
<213> ORGANISM: Artificial Sequence
<220> FEATURE:
<223> OTHER INFORMATION: VIM gBlock

<400> SEQUENCE: 73

```
caggtctcgt atgccaccca cacccaccgc gccctcgttc gcctcttctc cgggagccag      60
tccgcgccac cgccgccgcc caggccatcg ccacccctccg cagccatgtc caccaggtcc    120
gtgtcctcgt cctcctaccg caggatgttc ggcggcccgg gcaccgcgag ccggccgagc    180
```

```
tccagccgga gctacgtgac tacgtccacc cgcacctaca gcctgggcag cgcgctgcgc    240
cccagcacca gccgcagcct ctacgcctcg tccccgggcg gcgtgtatgc cacgcgctcc    300
tctgccgtgc gcctgcggag cagcgtgccc ggggtgcggc tcctgcagga ctcggtggac    360
ttctcgctgg ccgacgccat caacaccgag ttcaagaaca cccgcaccaa cgagaaggtg    420
gagctgcagg agctgaatga ccgcttcgcc aactacatcg acaaggtgcg cttcctggag    480
cagcagaata agatcctgct ggccgagctc gagcagctca agggccaagg caagtcgcgc    540
ctgggggacc tctacgagga ggagatgcgg gagctgcgcc ggcaggtgga ccagctaacc    600
aacgacaaag cccgcgtcga ggtggagcgc gacaacctgg ccgaggacat catgcgcctc    660
cgggagaaat tgcaggagga gatgcttcag agatgagcga gaccac                  706
```

HIGH THROUGHPUT NUCLEIC ACID PROFILING OF SINGLE CELLS

SEQUENCE LISTING

The instant application contains a Sequence Listing which has been submitted in ASCII format via EFS-Web and is hereby incorporated by reference in its entirety. The ASCII copy, created on Aug. 31, 2020, is named USPTO--200904--Pat App--P180094US02--SEQ LIST.TXT and is 22,345 bytes in size.

FIELD OF THE INVENTION

The invention is directed to high-throughput methods, systems, and devices for profiling the nucleic acid composition of single cells within a heterogeneous population of cells.

SEQUENCE LISTING

The instant application contains a Sequence Listing which has been submitted in ASCII format via EFS-Web and is hereby incorporated by reference in its entirety. The ASCII copy, created on Aug. 31, 2020, is named USPTO—200904—Pat App—P180094US02—SEQ LIST.TXT and is 22,345 bytes in size.

BACKGROUND

Cellular heterogeneity and its impact on biological function and disease are becoming increasingly important for questions in human immunology, stem cell biology, and cancer research. By transcriptionally analyzing individual cells with reverse-transcriptase polymerase chain reaction (RT-PCR), for example, it is possible to identify rare cells or transient cell states that are unobservable when studying the entire population in bulk (Bendall et al. 2012, Kalisky and Blainey et al. 2011, Kalisky and Quake 2011, Levsky et al. 2003). However, obtaining meaningful information on these cells necessitates tools capable of high-throughput analysis. Current methods for manipulating, isolating, and transcriptionally profiling single cells with RT-PCR are cumbersome and limited in throughput, enabling the examination of just hundreds of individual cells.

The ultrahigh-throughput capability of droplet-based microfluidics is ideal for single-cell analysis applications (Guo et al. 2012, Novak et al. 2011, Vyawahare et al. 2010). These microfluidic techniques rely on microdroplets, tiny spheres of aqueous liquid ranging from 1 to 100 μm in diameter, to encapsulate biological components in an oil-based emulsion (The et al. 2008). The drops serve, essentially, as very tiny "test tubes," compartmentalizing millions of reactions. A major advantage of this approach is that a minimal amount of reagent is used, greatly reducing the cost for a given experiment. In addition, with microfluidic techniques, the drops can be formed, split, injected with reagent, and sorted at kilohertz rates, holding potential for performing millions of single-cell reactions at unprecedented throughput. However, an obstacle to realizing the potential of this approach is that, at concentrations of a single cell in a microdroplet, cell lysate is a potent inhibitor of RT-PCR (Arezi et al. 2010, Hedman et al. 2013, White et al. 2011).

To avoid cell lysate inhibition of RT-PCR, previous drop-based methods have utilized large droplets (2 nL) in which the lysate concentration is no longer inhibitory, or agarose droplets that can be solidified, rinsed, and stained with DNA dyes (Mary et al. 2011, Zhang et al. 2012). Methods using large droplets have only been able to analyze ~100 cells in total, while the agarose method is unable to use TaqMan probes or cell staining, precluding correlation of specific cell types with associated transcriptional targets. An alternative strategy for performing single-cell RT-PCR on cells is to isolate the cells in microwells fabricated into an elastomeric device. This approach allows robust and specific single-cell transcriptional profiling. However, because each microwell and its control valves must be fabricated and individually controlled, throughput is also limited to just a few hundred cells in total (Kalisky and Blainey et al. 2011, Kalisky and Quake 2011, White et al. 2013). Yet other strategies for performing single-cell RT-PCR on single cells is lyse cells in microdroplets and then dilute the microdroplets prior to RT-PCR (Eastburn et al. 2013). While this dilution approach is effective, it is a highly cumbersome process that limits processivity.

To enable expression analysis of large numbers of cells in a heterogeneous population, new methods, systems, and devices are needed that combine the throughput of droplet-based microfluidic techniques with the specificity of microwell reactions. Aspects of the invention provided herein address these needs.

SUMMARY OF THE INVENTION

One aspect of the invention is directed to methods of profiling a nucleic acid composition of a single cell. The methods comprise isolating the single cell in a liquid droplet, lysing the single cell in the liquid droplet to release template nucleic acid from the cell, amplifying the template nucleic acid in the liquid droplet to generate amplified nucleic acid, and detecting the amplified nucleic acid in the liquid droplet.

Another aspect of the invention is directed to polymerase-dependent logic gates. The polymerase-dependent logic gates can be used in the profiling methods of the invention.

Another aspect of the invention is directed to microfluidic systems for performing the profiling methods of the invention.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIGS. 2-4, nucleic acid portions designated with a given number (e.g., "1") are substantially identical to nucleic acid portions designated with the same number and are substantially complementary to nucleic acid portions designated with the same number and an asterisk (e.g., "1*").

FIG. 3 shows an exemplary branch migration-mediated strand displacement logic gate employing a YES logical operation. The half arrowheads indicate 3' ends of depicted nucleic acid strands.

FIG. 4 shows a schematic of an exemplary polymerase-dependent logic gate employing a YES logical operation. The half arrowheads indicate 3' ends of depicted nucleic acid strands.

FIG. 7A shows components of the logic gate. FIG. 7B show operation of the logic gate in the presence of both of two targeted inputs. FIGS. 7C and 7D show operation of the logic gate in the presence of only one of the two targeted inputs. The half arrowheads indicate 3' ends of depicted nucleic acid strands. The logic gate shown in FIG. 7A can constitute an inclusive-OR logical operation if the threshold strand is absent.

FIG. 9A shows components of the logic gate. FIG. 9B shows operation of the logic gate in the presence of both of two targeted inputs, wherein the presence of input 2 negates the signal generated from the presence of input 1. FIGS. 9C and 9D show operation of the logic gate in the presence of only one of the two targeted inputs. The half arrowheads indicate 3' ends of depicted nucleic acid strands.

FIG. 14A shows high background using CHA in the presence of lysate. FIG. 14B shows concentration-dependent lysate inhibition. In FIG. 14A, error bars denote +/−1 standard deviation of the mean.

FIG. 15A shows amplification at a lysate concentration of $10^6$ cells/mL, which is equivalent to the lysate concentration of a single cell in a microdroplet. FIG. 15B shows amplification above and below a lysate concentration of $10^6$ cells/mL. Error bars denote +/−1 standard deviation of the mean.

FIG. 23A shows histograms for Alexa Fluor 647 signal with a human CK19− osteosarcoma cell line (U-2 OS) and a human CK19+ breast cancer cell line (SK-BR-3), after a 60-minute or 5-minute incubation. FIG. 23B shows histograms for HEX signal with a human VIM− breast cancer cell line (SK-BR-3) and a human VIM+ osteosarcoma cell line (U-2 OS), after a 60-minute or 5-minute incubation. Each YES gate was structured as shown in FIG. 4, and each reporter complex was structured as shown in FIG. 2.

DETAILED DESCRIPTION OF THE INVENTION

One aspect of the invention is directed to a method of profiling the nucleic acid composition of a single cell. The method may comprise isolating the single cell in a liquid droplet, lysing the single cell in the liquid droplet to release template nucleic acid from the cell, amplifying the template nucleic acid in the liquid droplet to generate amplified nucleic acid, and detecting the amplified nucleic acid in the liquid droplet.

Figure 1:
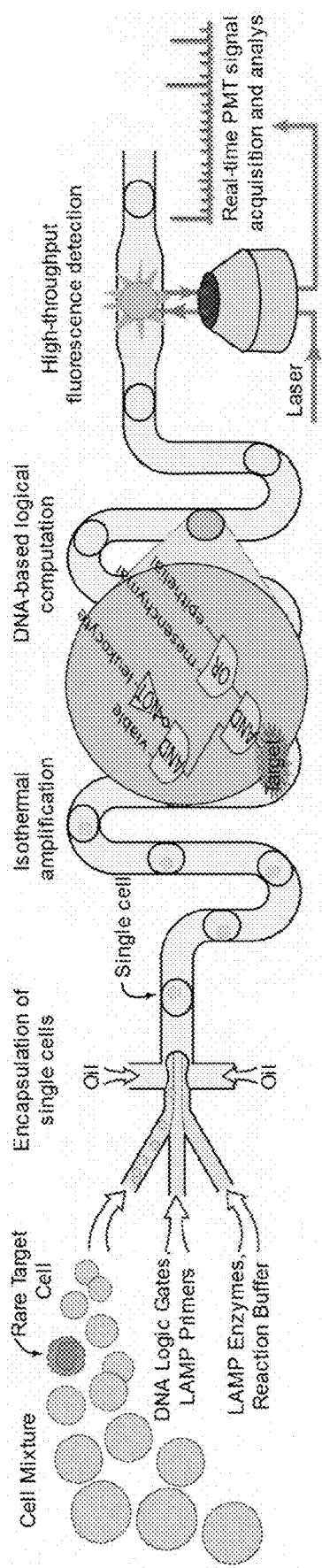
FIG. 1 shows a schematic of an exemplary version of a process of the invention.

A schematic of an exemplary version of this process is shown in FIG. 1. The exemplary process is for profiling nucleated blood cells for the presence of circulating tumor cells (CTCs). The isolating in FIG. 1 is depicted as "encapsulation of single cells," the lysing is depicted as "cell lysis," the amplifying is depicted as "amplification," and the detecting is depicted as "DNA-based logical computation" and "High-throughput fluorescence detection." As shown in FIG. 1, the isolating, the lysing, the amplifying, and the detecting can all occur in a single network of channels in a continuous, high-throughput manner. This is contrasted with processes that conduct certain steps in batch. The channels can be microfluidic channels generated using any suitable method. An exemplary method is provided in the following examples. As used herein, "channels" refers to passages embedded in a solid device as well as exposed tubing.

The isolating may comprise isolating the cell in an aqueous liquid droplet suspended in a water-immiscible medium. This can be performed by feeding the cells through microfluidic channels in a continuous aqueous solution stream past inlets for the water-immiscible medium. The water-immiscible medium disrupts the continuous aqueous solution stream and "pinches off" distinct liquid droplets such that the liquid droplets become suspended in the water-immiscible medium. The cells can be present in the continuous aqueous solution stream at a low enough concentration such that one or fewer cells become isolated in per aqueous liquid droplet formed. The water-immiscible medium may comprise an oil. An exemplary oil is fluorinated oil, such as QX200™ Droplet Generation Oil for EvaGreen #1864005 (BioRad, Hercules, Calif.). Various surfactants present in the water-immiscible medium and or the aqueous phase may help to stabilize the liquid droplets within the water-immiscible medium. The liquid droplets preferably have a volume of from about 1 pL to about 100 nL, such as a volume from about 10 pL to about 10 nL or from about 100 pL to about 1 nL. Amounts above and below these amounts are acceptable.

For downstream steps, such as the lysing, amplification, and detecting, each cell is preferably isolated in the liquid droplet with one or more reagents such as a lysis reagent, a DNA polymerase, amplification primers, deoxynucleotide triphosphates, RNase inhibitor, one or more nucleic acid logic gates, and a reporter. This can be performed by merging one or more solutions containing these reagents with a cell-containing solution upstream of where the droplets are formed. The solutions may form adjacent laminar flows prior to droplet formation. The solutions become co-encapsulated by the water-immiscible medium to form the droplet. Formation of the droplets thereby isolates individual cells with the reagents.

The lysis reagent isolated with the cell in the droplet may comprise a detergent. The detergent preferably comprises a non-denaturing detergent. The non-denaturing detergent preferably comprises a non-ionic detergent. Exemplary non-denaturing, non-ionic detergents include Tween 20 (Millipore Sigma, Burlington, Mass.), TRITON X-100 (Dow Chemical Company, Midland, Mich.) (4-(1,1,3,3-Tetramethylbutyl)phenyl-polyethylene glycol, t-octylphenoxypolyethoxyethanol, polyethylene glycol tert-octylphenyl ether), NP-40 (nonyl phenoxypolyethoxylethanol), NONIDET P-40 (Shell Chemical Co., The Hague, The Netherlands) (octyl phenoxypolyethoxylethanol), and others. The detergent is preferably present in the liquid droplet at a concentration of from about 0.5% v/v to about 5% v/v, such as a concentration of from about 1% v/v to about 5% v/v or a concentration of about 2.5% v/v. The lysis reagent may alternatively or additionally comprise a lytic enzyme. Exemplary lytic enzymes include lysozyme and phage lysins. Suitable lysozyme concentrations of lysozyme include concentrations between about 1 kU/ml and 60 kU/ml, such as about 30 kU/ml. Concentrations above and below these amounts are also acceptable. Optimal concentrations of other particular lytic enzymes can be easily determined. A detergent should be sufficient to lyse most cells, particularly when heated. For cells with cell walls, such as certain types of bacteria, the lysis reagent preferably includes a detergent in addition to a lytic enzyme. In some versions of the invention, a lysis reagent is absent and cell lysis occurs by virtue of heating alone.

The polymerase isolated with the cell in the droplet can be any polymerase suitable for downstream amplification of the target nucleic acid. For amplification of DNA target nucleic acid, the polymerase is preferably a DNA-dependent DNA polymerase. DNA-dependent DNA polymerases are enzymes that catalyze the replication of DNA from a DNA template. An exemplary DNA-dependent DNA polymerase is Taq polymerase. For the amplification of RNA target nucleic acid, the polymerase is preferably a DNA- and RNA-dependent DNA polymerase or a combination of a DNA-dependent DNA polymerase with a separate RNA-dependent DNA polymerase. RNA-dependent DNA polymerases are enzymes that catalyze the production of DNA from a RNA template. RNA-dependent DNA polymerases are sometimes known as "reverse transcriptases." DNA- and RNA-dependent DNA polymerases are enzymes that have both DNA-dependent DNA polymerase activity and RNA-dependent DNA polymerase (reverse transcriptase) activity. "Amplification" is used herein as is typically used in the art except that it is understood herein also to encompass the reverse transcription of an RNA target nucleic acid to DNA.

For the certain types of amplification, such as isothermal amplification, the polymerase additionally has strand displacement activity and lacks 5'→3" exonuclease activity. The polymerase may also contain or lack and 3'→5' exonuclease activity. The polymerase is preferably thermostable. An exemplary polymerase is the Bst 2.0 DNA Polymerase (New England BioLabs, Inc., Ipswich, Mass.). This enzyme has RNA-dependent DNA polymerase (reverse transcriptase) activity, DNA-dependent DNA polymerase activity, and strand displacement activity and lacks 5'→3" exonuclease activity. Other polymerases with these characteristics are well-known in the art.

The amplification primers isolated with the cell in the droplet include any primers suitable for amplification of the nucleic acid template. A number of amplification methods and the design of suitable primers therefor are known in the art. The dNTPs serve as the building blocks for the amplified nucleic acids in the amplification.

The nucleic acid logic gate isolated with the cell in the droplet may comprise any one or more nucleic acid gates suitable for profiling nucleic acids. Exemplary nucleic acid logic gates are known in the art and are described elsewhere herein.

The reporter isolated with the cell in the droplet may comprise any reagent suitable for indicating the presence of nucleic acids generally or particular nucleic acids specifically. Exemplary reporters are known in the art and are described elsewhere herein.

The lysing step may comprise heating the cell either in the presence or absence of a lysis reagent within the droplet. This step may be performed by heating the droplet containing the cell or the cell and lysis reagent. Heating the droplet may be performed by flowing the droplet containing the cell or the cell and lysis reagent through a heated zone. The heated zone may comprise an entire channel-containing device or subsections thereof. In some versions, a heating step is not required, as mixing the lysis reagent with the cell may be sufficient on its own to lyse the cell.

The amplifying may comprise amplifying a DNA template or reverse transcribing template RNA into DNA and amplifying the reverse transcribed DNA. The type of amplification used depends on the type of nucleic acid targeted for profiling. DNA templates, for example, will typically require only amplification of the DNA itself. RNA templates, by contrast, will typically require reverse transcription and DNA amplification.

The amplification method may comprise any method suitable for amplifying nucleic acids. Exemplary methods comprise PCR and isothermal amplification methods. Reverse transcription may be combined with PCR or the isothermal amplification method. Exemplary isothermal amplification methods include enzyme-free isothermal amplification methods and enzyme-dependent isothermal amplification methods. Exemplary enzyme-free isothermal amplification methods include hybridization chain reaction (HCR), catalytic hairpin assembly (CHA), and others. Exemplary enzyme-dependent isothermal amplification methods include loop-mediated isothermal amplification (LAMP), rolling circle amplification (RCA), multiple displacement amplification (MDA), recombinase polymerase amplification (RPA), nucleic acid sequence-based amplification (NASBA), among others.

The presence of lysis reagent and/or undiluted cell lysate during amplification can inhibit certain amplification methods such as PCR and enzyme-free isothermal amplification methods such as HCR and CHA. As shown in the following examples, LAMP was capable of producing a strong amplification signal in the presence of the lysis reagent and undiluted cell lysate. Thus, preferred amplification methods for performing in the presence of lysis reagent and/or undiluted cell lysate include enzyme-mediated isothermal amplification methods such as LAMP.

After nucleic acid amplification, the amplified nucleic acid can be detected by a number of methods. Preferred methods include fluorescent methods. The methods can include non-specific nucleic acid detection and specific nucleic acid detection.

Non-specific nucleic acid detection detects nucleic acid regardless of the particular sequence using a non-specific nucleic acid reporter, such as a non-specific fluorescent DNA reporter. Exemplary non-specific nucleic acid reporters include ethidium bromide, propidium iodide, CRYSTAL VIOLET (hexamethylpararosaniline chloride) (Sigma-Aldrich, St. Louis, Mo.), dUTP-conjugated probes, DAPI (4',6-diamidino-2-phenylindole) (Thermo Fisher Scientific Corporation, Waltham, Mass.), 7-AAD (7-aminoactinomycin D) (Thermo Fisher Scientific Corporation, Waltham, MA), HOECHST 33342 (2'-[14-ethoxyphenyl]-5-[14-methyl-1-piperazinyl]-2,5'-bi-1H-benzimidazole trihydrochloride trihydrate) (Thermo Fisher Scientific Corporation, Waltham, MA), HOECHST 34580 (N,N-dimethyl-4-[15-(4-methyl-1-piperazinyl)[2,5 '-bi-1H-benzimidazol]-2'-yl]benzenamine trihydrochloride) (Thermo Fisher Scientific Corporation, Waltham, MA), PICOGREEN® (2-[N-bis-(3-dimethylaminopropyl)-amino]-4-[2,3-dihydro-3-methyl-(benzo-1,3-thiazol-2-yl)-methylidene]-1-phenyl-quinolinium) (Molecular Probes, Inc., Eugene, OR), HELIXYTE™ (green double-stranded DNA quantifying reagent) (AAT Bioquest, Sunnyvale, CA), YOYO™-1 (quinolinium, 1,1 '-[1,3-propanediylbis [(dimethyliminio)-3,1-propanediyl]]bis[4-[(3-methyl-2(3H)-benzoxazolylidene) methyl]-, tetraiodide) (Thermo Fisher Scientific Corporation, Waltham, MA), DITO™-1 (1,1'-(4,4,7,7-tetramethyl-4,7-diazaundecamethylene)bis-4-(3-methyl-2,3-dihydro(benzo-1,3-thiazole)-2-methylidene)quinolinium) (AAT Bioquest. Sunnyvale, CA), and SYBR® dyes (Molecular Probes, Inc., Eugene, OR), such as SYBR® Green I (N',N'-dimethyl-N-[4-[(E)-(3-methyl-1,3-benzothiazol-2-ylidene)methyl]-1-phenylquinolin-1-ium-2-yl]-N-propyl-propane-1,3-diamine) (Molecular Probes, Inc., Eugene, OR), SYBR® Green II (RNA gel stain) (Molecular Probes, Inc., Eugene, OR), SYBR® Gold ([2-[N-(3-dimethylaminopropyl)-N-propylamino]-4-[2,3-dihydro-3-methyl-(benzo-1,3-thiazol-2-yl)-methylidene]-1-phenyl-quinolinium]) (Molecular Probes, Inc., Eugene, OR), etc. Many of these non-specific nucleic acid reporters are DNA intercalating agents.

Figure 2:
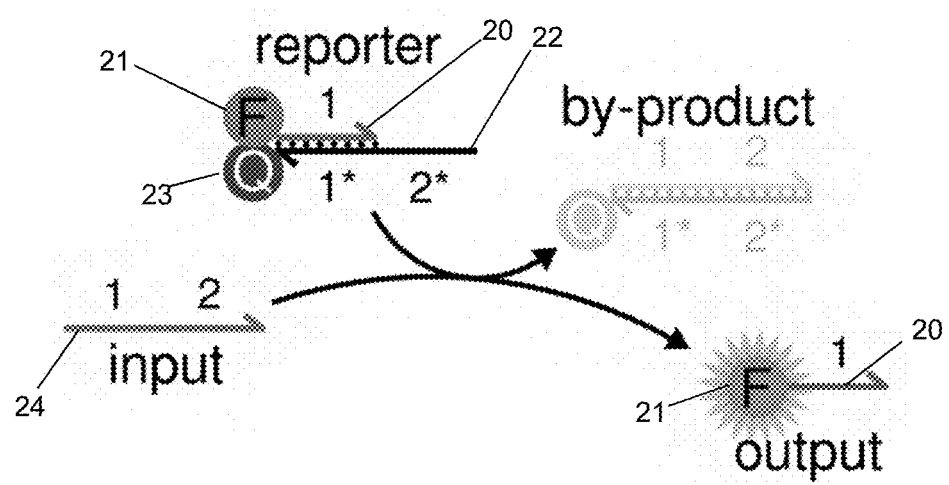
FIG. 2 shows a schematic of an exemplary branch migration-mediated strand displacement reporter. The half arrowheads indicate 3' ends of depicted nucleic acid strands.

Specific nucleic acid detection detects species of nucleic acid having a particular sequence with a sequence-specific nucleic acid reporter, such as a sequence-specific fluorescent nucleic acid reporter. A number of sequence-specific nucleic acid fluorescent reporters are known in the art. Exemplary sequence-specific fluorescent nucleic acid reporters include quenched reporters that release the quencher upon binding to a particular sequence. An example of a sequence-specific fluorescent nucleic acid reporter is shown in FIG. 2. This reporter is configured to operate through branch migration-mediated strand displacement. The reporter comprises a quencher strand 22 (black) annealed to a substantially complementary reporter strand 20 (red). The quencher strand 22 comprises a quencher 23 (Q). The reporter strand 20 comprises a fluorophore 21 (F). Annealing of the quencher strand 22 to the reporter strand 20 places the quencher 23 in close proximity to the fluorophore 21, thereby quenching any fluorescence emitted from the fluorophore 21. The reporter strand 20 anneals only to a first portion (1*) of the quencher strand 22, leaving a second portion (2*) of the quencher strand 22, referred to as a toehold, exposed. The quencher strand 22 is designed to be substantially complementary to an input strand 24 (blue). The input strand 24 is a nucleic acid intended to be detected. The input strand 24 comprises a portion (2) substantially complementary to the toehold (1*). When present, the input strand 24 binds to the toehold via the substantially complementary portion and displaces the reporter strand 20 from the quencher strand 22 upon annealing to the remainder of the quencher strand 22. Displacement of the reporter strand 20 removes the fluorophore 21 from the proximity of the quencher 23, thereby resulting in an activated reporter (shown as "output" in FIG. 2). The activated reporter can then fluoresce upon excitation with light. In alternative versions, the reporter strand is substantially complementary to the input strand and comprises a toehold such that binding of the input strand to the toehold on the reporter strand followed by branch migration displaces the quencher strand from the reporter strand. The resulting input strand/reporter strand duplex is then capable of fluorescing.

The detection may comprise profiling the composition of amplified nucleic acids by performing a molecular logical computation using a molecular logic circuit. The molecular logic circuit inputs one or more particular species of nucleic acid, performs a logical computation, and outputs one or more different species of nucleic acid. The molecular logic circuit comprises one or more nucleic acid logic gates used alone or in various combinations. As used herein, "molecular logical computation" or "molecularly computing" refers to the production of one or more output nucleic acids (e.g., output strands) from one or more nucleic acid logic gates in response to one or more input nucleic acids (e.g., input strands). "Production" in this context refers to the displacement of the output nucleic acid from a nucleic acid logic gate such that the output nucleic acid can be detected or used as an input for one or more downstream nucleic acid logic gates, as described in further detail below. The molecular logic circuit may be a DNA-based molecular logic circuit containing one or more DNA logic gates, an RNA-based molecular logic circuit containing one or more logic gates, or a combination thereof.

Each logic gate is configured to perform a specific logical operation. Exemplary logical operations include YES, NOT, AND, OR, AND-NOT, NOT-AND, NOT-OR, EXCLUSIVE-OR, EXCLUSIVE-NOR, and IMPLY.

YES and NOT gates are each configured for profiling a single input.

A YES gate produces an output (1) if and only if the input is in high abundance. This means that the gate fails to produce an output (0) if the input is not in high abundance. A YES gate may also be referred to as a "transducer." A logical operation performed by a YES gate for input A is shown in the following truth table:

| YES gate | |
|---|---|
| A | A |
| 1 | 1 |
| 0 | 0 |

The NOT gate is a circuit that produces an inverted version of the input at its output. It is also known as an inverter. If the input variable is A, the inverted output is NOT A. This is also shown as A', or A with a bar over the top. A logical operation performed by a NOT gate for input A is shown in the following truth table:

| NOT gate | |
|---|---|
| A | $\overline{A}$ |
| 0 | 1 |
| 1 | 0 |

The AND, OR, AND-NOT, NOT-AND, NOT-OR, EXCLUSIVE-OR, and EXCLUSIVE-NOR operations are each configured for profiling multiple inputs.

The AND gate is configured to give a high output (1) only if all its inputs are high and otherwise fails to produce a high output (0). A dot (.) is used to show the AND operation: A.B. The dot is sometimes omitted: AB. A logical operation performed by an AND gate for inputs A and B is shown in the following truth table:

| 2 Input AND gate | | |
|---|---|---|
| A | B | A.B |
| 0 | 0 | 0 |
| 0 | 1 | 0 |
| 1 | 0 | 0 |
| 1 | 1 | 1 |

An OR gate (otherwise known as an INCLUSIVE-OR gate) is configured to give a high output (1) if one or more of its inputs are high. A plus (+) is used to show the OR operation. A logical operation performed by an OR gate for inputs A and B is shown in the following truth table:

| 2 Input OR gate | | |
|---|---|---|
| A | B | A + B |
| 0 | 0 | 0 |
| 0 | 1 | 1 |
| 1 | 0 | 1 |
| 1 | 1 | 1 |

A NOT-AND (NAND) gate is equal to an AND gate followed by a NOT gate. The outputs of all NAND gates are high (1) if any of the inputs are low (0). A logical operation performed by a NAND gate for inputs A and B is shown in the following truth table:

| 2 Input NAND gate | | |
|---|---|---|
| A | B | $\overline{A.B}$ |
| 0 | 0 | 1 |
| 0 | 1 | 1 |
| 1 | 0 | 1 |
| 1 | 1 | 0 |

An AND-NOT gate detects the presence of only one of two possible inputs. The outputs of AND-NOT gates are high (1) if one and only one of two possible inputs are high (1) and low (0) if any other conditions obtain. A truth table for an AND-NOT gate in which input B is negated (A AND-NOT B) is as follows:

| 2 Input AND-NOT gate | | |
|---|---|---|
| A | B | Output |
| 0 | 0 | 0 |
| 0 | 1 | 0 |
| 1 | 0 | 1 |
| 1 | 1 | 0 |

A NOT-OR (NOR) gate is equal to an OR gate followed by a NOT gate. The outputs of all NOR gates are low (0) if any of the inputs are high (1). A logical operation performed by a NOR gate for inputs A and B is shown in the following truth table:

| 2 Input NOR gate | | |
|---|---|---|
| A | B | $\overline{A+B}$ |
| 0 | 0 | 1 |
| 0 | 1 | 0 |
| 1 | 0 | 0 |
| 1 | 1 | 0 |

An EXCLUSIVE-OR (EXOR) gate is configured to give a high output if either, but not both, of its two inputs are high (1). An encircled plus sign is used to show the EXOR operation. A logical operation performed by an EXCLUSIVE-OR gate for inputs A and B is shown in the following truth table:

| 2 Input EXOR gate | | |
|---|---|---|
| A | B | $A \oplus B$ |
| 0 | 0 | 0 |
| 0 | 1 | 1 |
| 1 | 0 | 1 |
| 1 | 1 | 0 |

An EXCLUSIVE-NOR (EXNOR) gate does the opposite of the EXOR gate. The EXCLUSIVE-NOR gate is configured to give a high output if both of two inputs are high (1) or if both of two inputs are low (0). It gives a low output if either, but not both, of its two inputs are high. A logical operation performed by an EXCLUSIVE-NOR gate for inputs A and B is shown in the following truth table:

| 2 Input EXNOR gate | | |
|---|---|---|
| A | B | $\overline{A \oplus B}$ |
| 0 | 0 | 1 |
| 0 | 1 | 0 |
| 1 | 0 | 0 |
| 1 | 1 | 1 |

An IMPLY gate employs a CONDITIONAL logical operation, by conveying "if-then" logic.

Nucleic acid logic gates configured to perform logical operations are known in the art. See, e.g., Baccouche et al. 2014, Chen et al. 2015, Deng et al. 2014, Li et al. 2011, Li et al. 2013, Li et al. 2016, Massey et al. 2017, Okamoto et al. 2004, Qian and Winfree 2011, Qian and Winfree et al. 2011, Ravan et al. 2017, Thubagere et al. 2017, Wei et al. 2016, Xu et al. 2014, Yang et al. 2013, Yang et al. 2016, Yang et al. 2014, Yao et al. 2015, Zhang et al. 2010, Zhu et al. 2013, Zou et al. 2017, US 2007/0072215, and WO 2017/141068.

Figure 3:
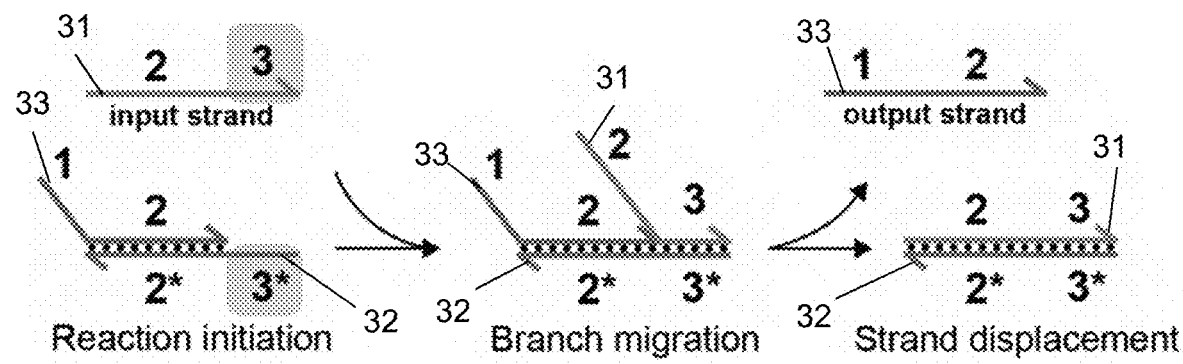

Exemplary logic gates operate through branch migration-mediated strand displacement, also known as toehold-mediated branch migration or random-walk branch migration. A schematic of an exemplary branch migration-mediated strand displacement logic gate employing a YES logical operation is shown in FIG. 3. The logic gate comprises an output strand 33 (brown strand) annealed to a substantially complementary gate strand 32 (blue). An input strand 31 (green) that is substantially complementary to the gate strand 32 binds to an exposed toehold (3*) portion of the gate strand 32 and subsequently displaces the output strand 33 upon further annealing to the gate strand 32. The branch migration-mediated strand displacement mechanism can be configured to generate logic gates employing other operations, such as NOT, AND, OR, NOT-AND, NOT-OR, EXCLUSIVE-OR, EXCLUSIVE-NOR operations, among others. See, e.g., the references provided above.

Figure 4:
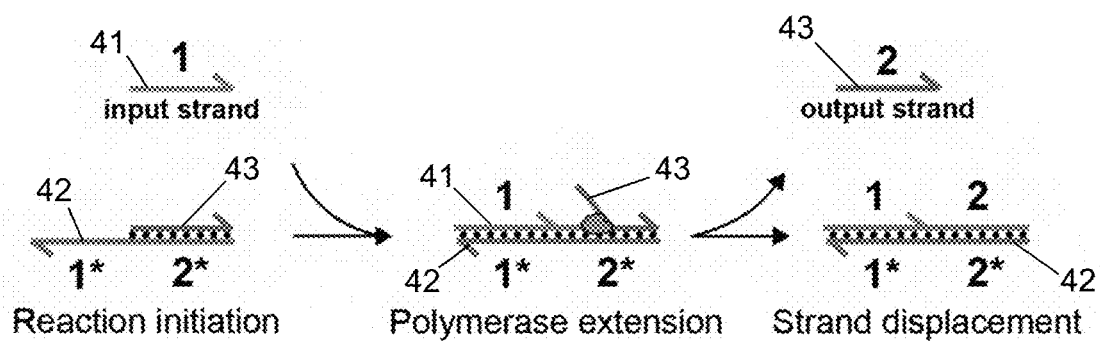

Other exemplary logic gates include polymerase-dependent logic gates. Polymerase-dependent logic gates require polymerase-mediated extension of an input strand along a gate strand to displace an output strand from the gate strand. These logic gates are designed to operate with polymerases that have strand displacement activity and lack 5'→3' exonuclease activity. A schematic of an exemplary polymerase-dependent logic gate employing a YES logical operation is shown in FIG. 4. The polymerase-dependent logic gate comprises an output strand 43 (brown) annealed to a gate strand 42 (blue). The output strand 43 anneals to an output-strand annealing portion (2*) of the gate strand 42. The output strand 43 does not anneal to an output-strand non-annealing portion (1*) of the gate strand 42, leaving an exposed portion on the gate strand 42. The output-strand annealing portion is closer to the 5' end of the gate strand 42 (brown) than the output-strand non-annealing portion. An input strand 41 (green) anneals to an input-strand annealing portion (1*) of the gate strand 42. In the example in FIG. 4, the input-strand annealing portion of the gate strand 42 is the same as the output-strand non-annealing portion, but it does not have to be so. The input strand 41 does not anneal to an input-strand non-annealing portion (2*) of the gate strand 42. In the example in FIG. 4, the input-strand non-annealing portion of the gate strand 42 is the same as the output-strand annealing portion, but it does not have to be so. Mere binding of the input strand 41 to the input-strand annealing portion of the gate strand 42 is on its own insufficient to displace the output strand 43 from the gate strand 42. Extension of the input strand 41 along the gate strand 42 must occur to displace the output strand 43 from the gate strand 42. The output strand 43 can then be directly detected with a reporter gate or serve as input for one or more additional logic gates.

The input-strand non-annealing portion of the gate strand does not have to be the same as the output-strand annealing portion. In order for there to be an exposed portion near the 3' end of the input strand to facilitate binding of the input strand, however, the input-strand annealing portion and the output-strand non-annealing portion at least partially overlap. In some versions, the input-strand annealing portion is a sub-portion of the output-strand non-annealing portion. For binding of the input strand not to be sufficient displace the output strand (i.e., for extension of the input strand along the gate strand to be necessary for displacement of the output strand), the output-strand annealing portion and the input-strand non-annealing portion at least partially overlap. In some versions, the output-strand annealing portion and the input-strand annealing portion at least partially overlap. Too much overlap, however, will induce displacement of the output strand merely by the input strand binding to the exposed portion on the gate strand without requiring polymerase-mediated extension of the input strand. Thus, any overlap between the output-strand annealing portion and the input-strand annealing portion is an amount less than that sufficient for the input strand to displace the output strand without polymerase-mediated extension. In preferred versions of the invention, the output-strand annealing portion and the input-strand annealing portion do not overlap. This is thought to permit faster binding kinetics between the input strand and the gate strand.

In some versions, the input-strand annealing portion the gate strand can serve as a primer for an amplification reaction, wherein the input-strand annealing portion binds to a sequence on a template nucleic acid. In some versions, the amplification reaction is LAMP. The gate strand can serve as a forward internal primer (FIP) or a backward internal primer (BIP) in the LAMP reaction. Amplification from the forward outer primer (FP) and/or backward outer primer (BP), respectively, can displace an output strand initially bound to the gate strand.

The polymerase-dependent logic gates can be configured to perform any of the logical operations described herein, including the YES, NOT, AND, OR, AND-NOT, NOT-AND, NOT-OR, EXCLUSIVE-OR, EXCLUSIVE-NOR, and IMPLY operations, among others.

Figure 5:
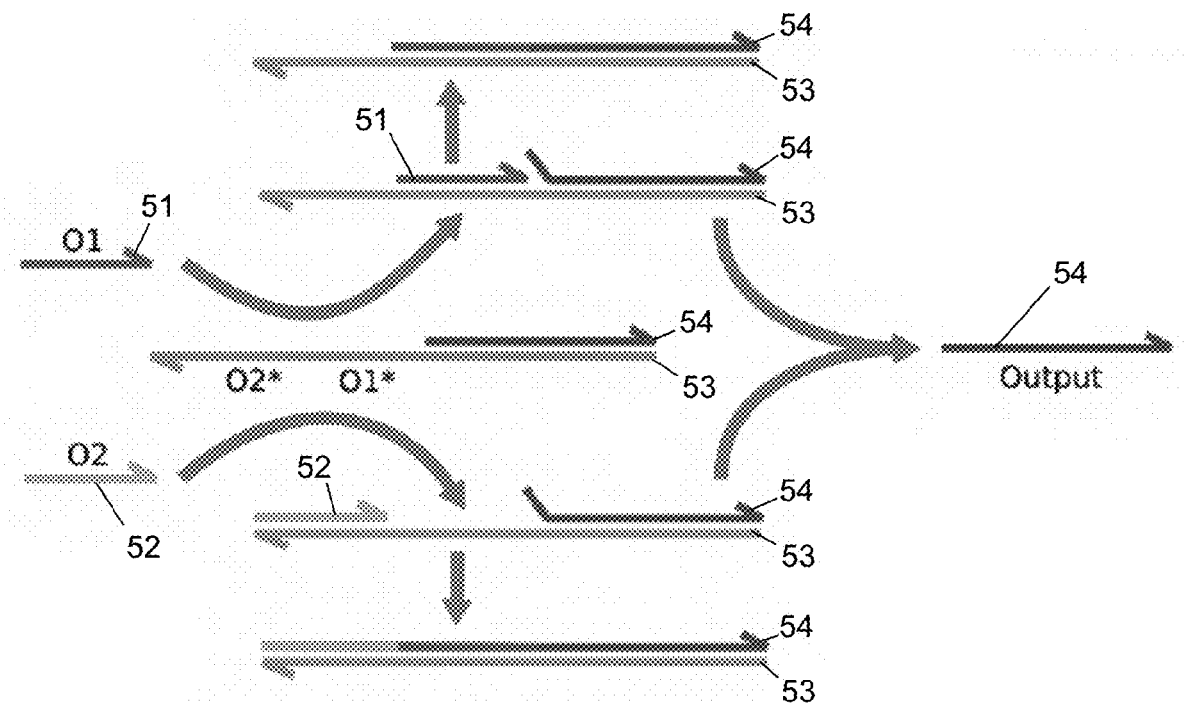
FIG. 5 shows a schematic of an exemplary polymerase-dependent logic gate employing an OR logical operation. The half arrowheads indicate 3' ends of depicted nucleic acid strands.

An exemplary polymerase-dependent OR logic gate is shown in FIG. 5. The input-strand annealing portion of the gate strand 53 (green) has a first input-strand annealing portion (O1*) and a second input-strand annealing portion (O2*). The first input-strand annealing portion is substantially complementary to and anneals to a first input strand 51 (red). The second input-strand annealing portion (O2*) is substantially complementary to and anneals to a second input strand 52 (teal). Annealing of either or both of the first 51 and second 52 input strands induces polymerase-mediated extension thereof and displaces the output strand 54 (blue) from the gate strand.

Figure 6:
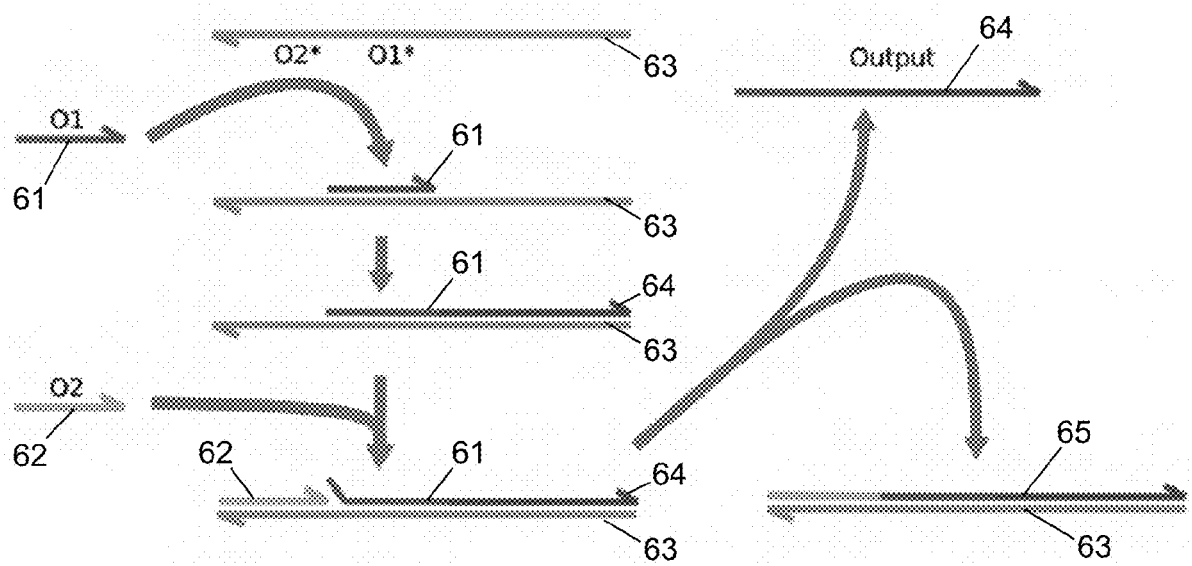
FIG. 6 shows a schematic of an exemplary polymerase-dependent logic gate employing an AND logical operation. The half arrowheads indicate 3' ends of depicted nucleic acid strands.

An exemplary polymerase-dependent AND logic gate is shown in FIG. 6. This logic gate has a gate strand 63 (green) without a pre-annealed output strand and instead employs an output strand 64 (red/blue) that is generated in situ. As with the OR logic gate, the input-strand annealing portion (O2*O1*) of the gate strand 63 has a first input-strand annealing portion (O1*) and a second input-strand annealing portion (O2*). The first input-strand annealing portion (O1*) is substantially complementary to and anneals to a first input strand 61 (red). The second input-strand annealing portion (O2*) is substantially complementary to and anneals to a second input strand 62 (teal). The output strand 64 is generated in situ through binding of the first input strand 61 to the first input-strand annealing portion and polymerase-mediated extension of the first input strand 61 along the gate strand. The generated output strand 64 is then displaced upon binding of the second input strand 62 to the second input-strand annealing portion and extension of the second input strand to generate an extended input strand 65 (teal/red/blue).

Figure 7A:
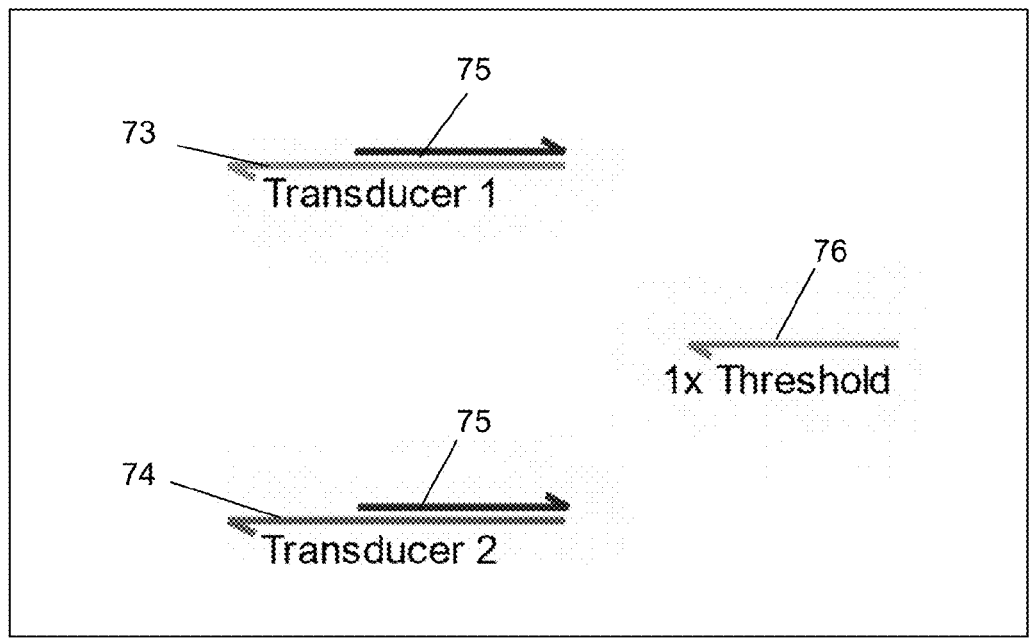
FIGS. 7A-7D show a schematic of an alternative exemplary polymerase-dependent logic gate employing an AND logical operation.
Figure 7B:
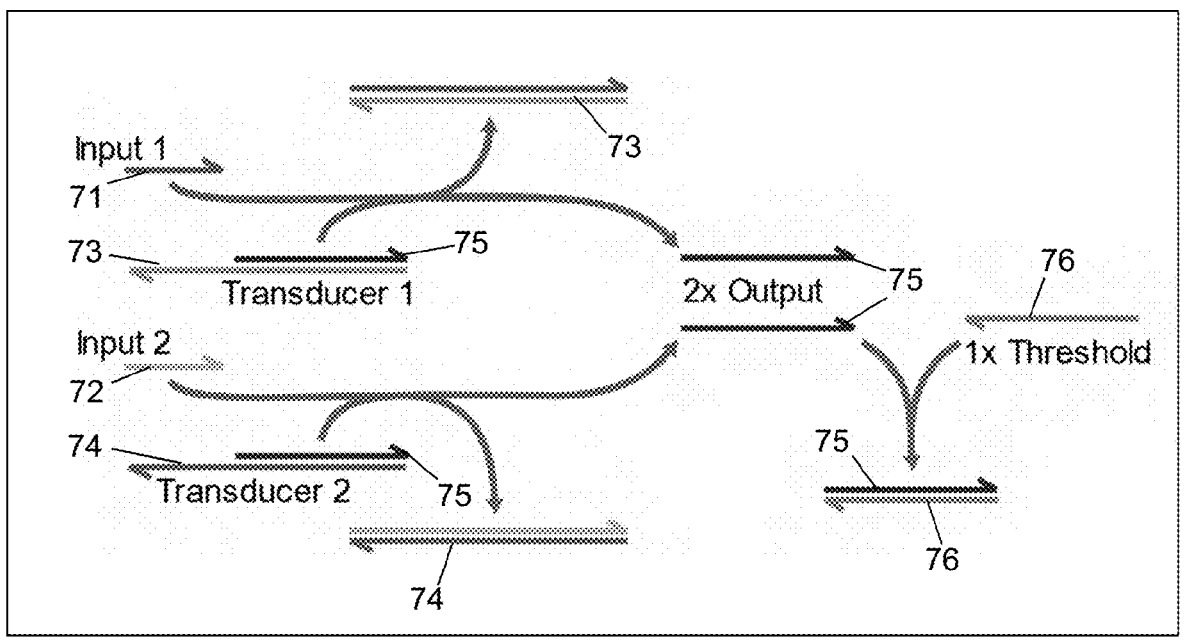
Figure 7C:
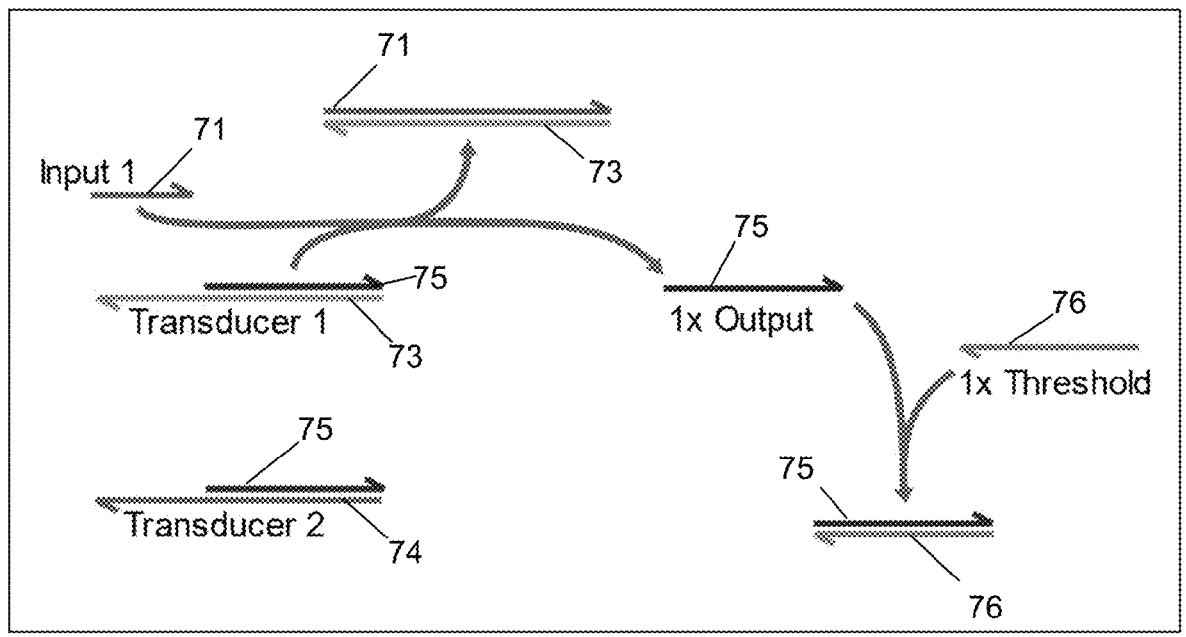
Figure 7D:
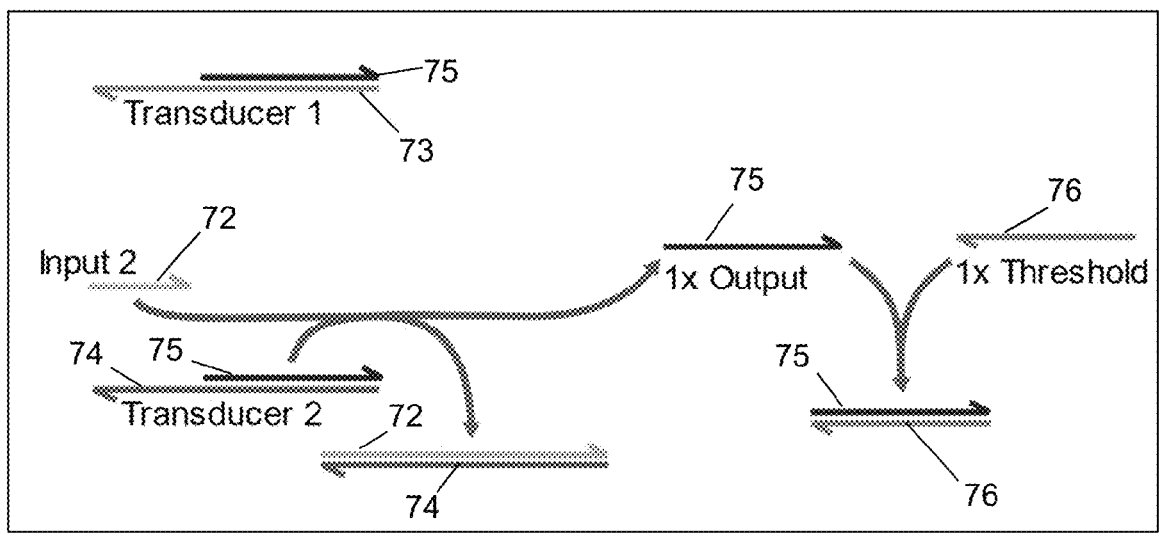

An alternative exemplary polymerase-dependent AND logic gate is shown in FIGS. 7A-7D. This logic gate includes at least two distinct gate strands 73,74 (green, fuchsia), output strands 75 (blue), and a threshold strand 76. "Distinct" used with reference to nucleic acid means that the nucleic acids have different nucleotide sequences. The output strands 75 are initially bound to the gate strands 73,74 but are substantially complementary to and are capable of annealing to the threshold strand 76. The threshold strand 76 each of the at least two distinct gate strands 73,74 with the output strands 75 bound thereto are present in a substantially equimolar concentration. "Substantially equimolar" in this context refers to equimolar amounts or a molar excess of one strand over each other relevant strand less than about 40%, less than about 35%, less than about 30%, less than about 25%, less than about 20%, less than about 15%, less than about 10%, less than about 5%, less than about 4%, less than about 3%, less than about 2%, or less than about 1%. A slight molar excess of the threshold strand over each of the at least two distinct gate strands 73,74 with the output strands 75 bound thereto is acceptable. The slight excess may be a molar excess less than about 40%, less than about 35%, less than about 30%, less than about 25%, less than about 20%, less than about 15%, less than about 10%, less than about 5%, less than about 4%, less than about 3%, less than about 2%, or less than about 1%. In the present example, the output strands 75 for each of the two gate strands 73,74 are identical. However, they need not be identical, so long as they each have a portion that is capable of binding to the threshold strand 76 (and any downstream logic gate or reporter gate), and are therefore substantially identical. The input-strand annealing portion of a first 73 (green) of the at least two distinct gate strands 73,74 anneals to a first 71 (red/Input 1) of at least two distinct input strands 71,72 but not to a second 72 (teal/Input 2) of the at least two distinct input strands 71,72. The input-strand annealing portion of a second 74 (fuschia) of the at least two distinct gate strands 73,74 anneals to the second 72 (teal/Input 2) of the at least two distinct input strands 71,72 but not to the first 71 (red/Input 1) of the at least two distinct input strands 71,72. As shown in FIG. 7C and FIG. 7D, the presence of only one of the two input strands 71,72 displaces an amount of output strand 75 (1×) that is less than or equal to the amount of threshold strand 76. The threshold strand 76 thus binds to all of the displaced output strand 75 and quarantines it from detection or further signaling through downstream logic gates. As shown in FIG. 7B, however, the presence of both of the two input strands 71,72, displaces an amount of output strand 75 (2×) that is greater than the amount of threshold strand 76. The threshold strand 76 is therefore capable of binding only to subset of the displaced output strand 75, leaving a second subset free for detection or further signaling through downstream logic gates. If the threshold strand 76 is omitted, then activation of either transducer 73,75 or 74,75 is sufficient to produce free output strand 75 (blue), and this forms an alternative, exemplary OR gate.

Figure 8:
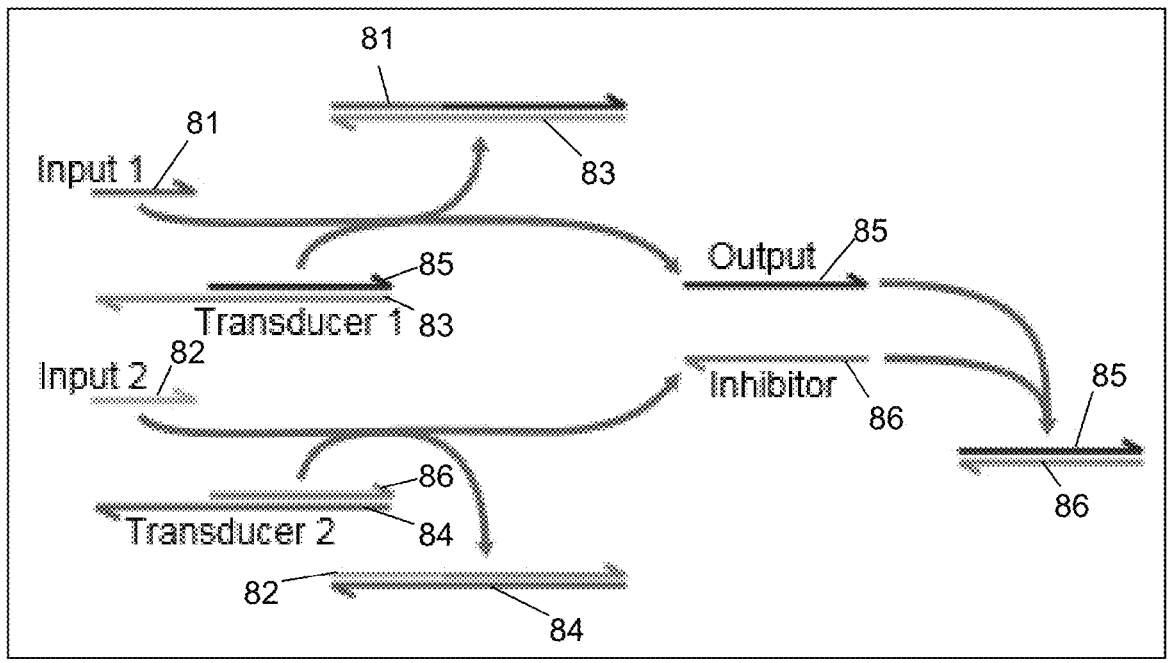
FIG. 8 shows a schematic of an exemplary polymerase-dependent logic gate employing an AND-NOT logical operation. The half arrowheads indicate 3' ends of depicted nucleic acid strands.

An exemplary polymerase-dependent AND-NOT logic gate is shown in FIG. 8. This logic gate comprises at least two distinct gate strands 83,84 (green, fuchsia). Each gate strand 83,84 is bound to a distinct output strand 85,86 (blue, red, respectively). The output strands 85,86 are substantially complementary to each other and are capable of annealing to each other once displaced from the gate strands 83,84. The input-strand annealing portion of a first 83 (green) of the at least two distinct gate strands 83,84 anneals to a first 81 (red/Input 1) of at least two distinct input strands 81,82 but not to a second 82 (teal/Input 2) of the at least two distinct input strands 81,82. The input-strand annealing portion of a second 84 (fuschia/Input 2) of the at least two distinct gate strands 83,84 anneals to the second 82 (fuchsia/Input 2) of the at least two distinct input strands 81,82 but not to the first 81 (teal/Input 2) of the at least two distinct input strands 81,82. When only one 81 (teal/Input 2 or fuschia/Input 2) of the two distinct input strands 81,82 is present, the output strand 85 or 86 (blue or red, respectively) is displaced and can be detected or used for signaling in downstream logic gates. When both of the input strands 81,82 (teal/Input 2 and fuschia/Input 2) are present, the displaced output strands 85,86 anneal to each other when released from the gate strands 83,84 and quarantine each other from detection or signaling in downstream logic gates.

Figure 9A:
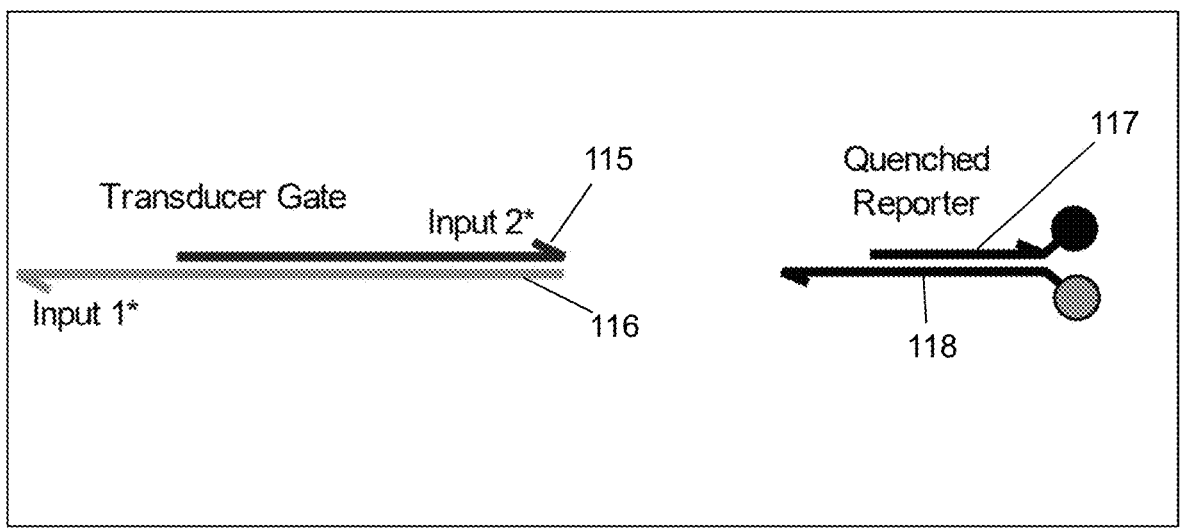
FIGS. 9A-9D show a schematic of an alternative exemplary polymerase-dependent logic gate employing an AND-NOT logical operation. The half arrowheads indicate 3' ends of depicted nucleic acid strands.
Figure 9B:
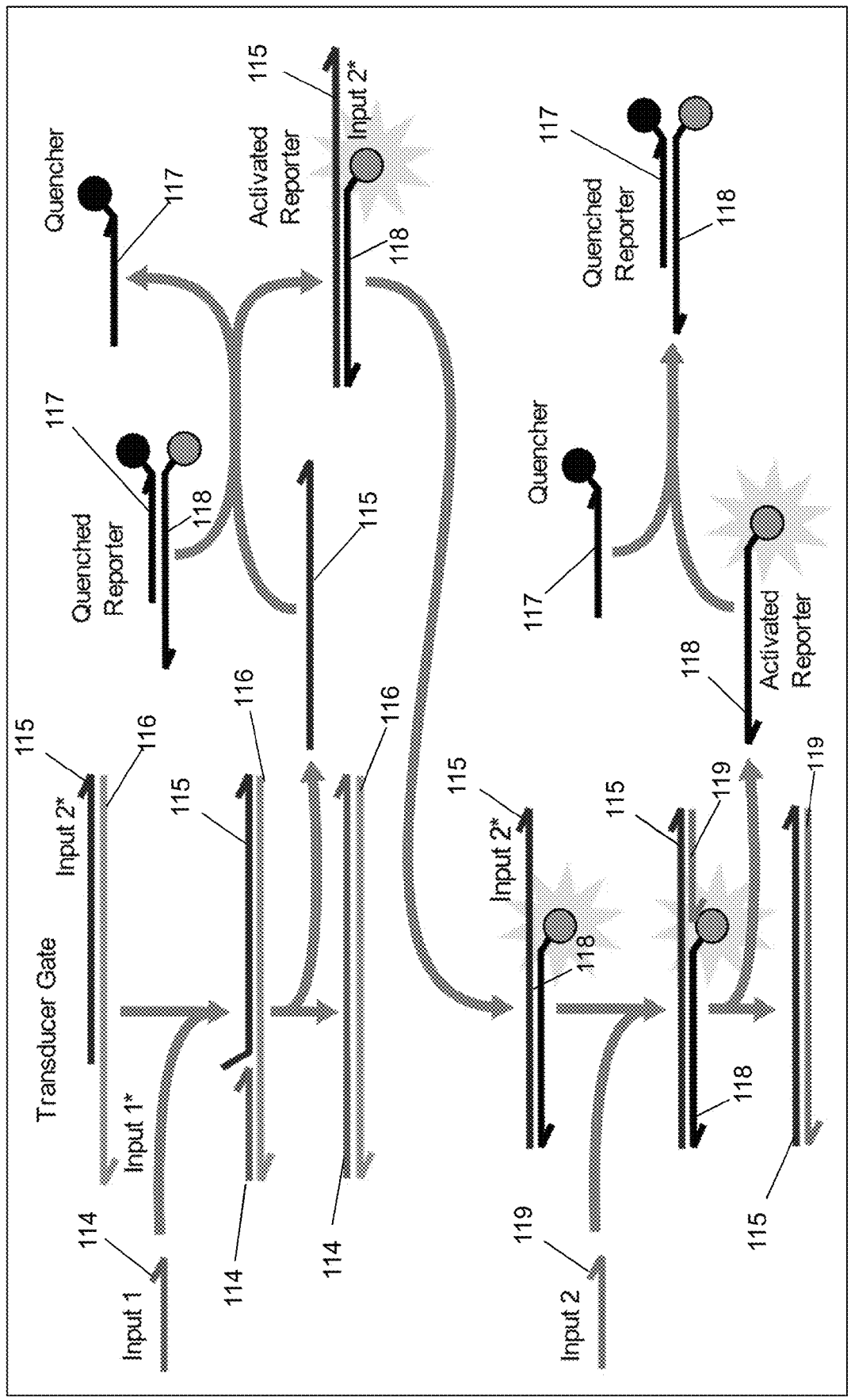
Figure 9C:
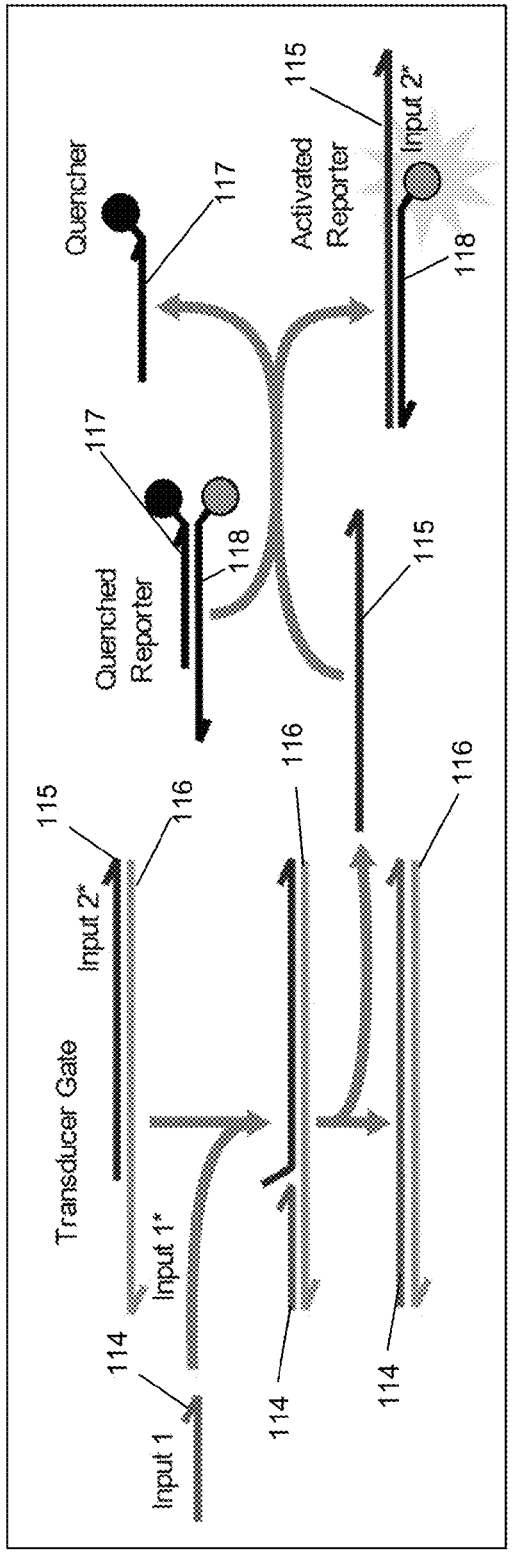
Figure 9D:
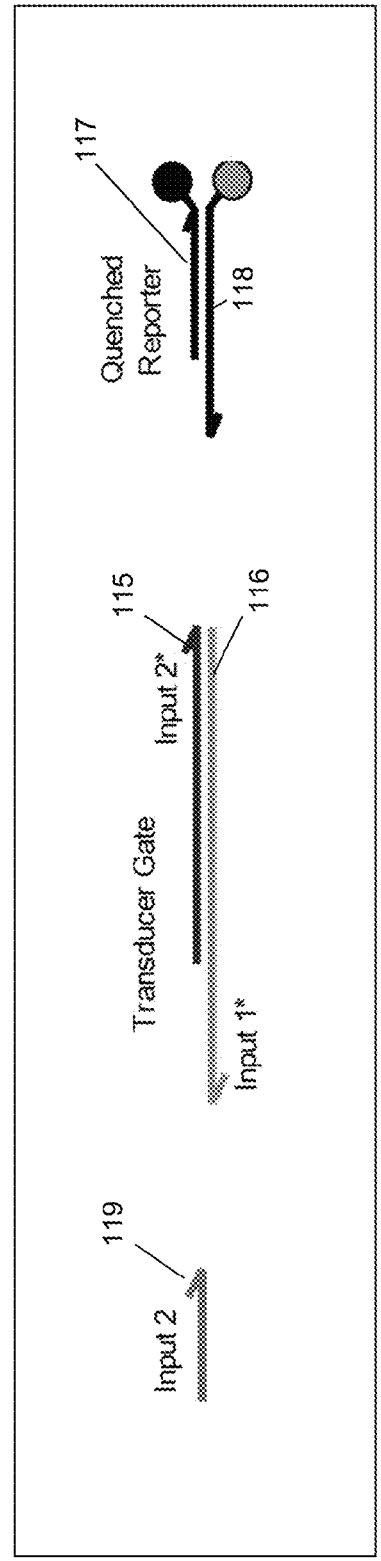

An alternative exemplary polymerase-dependent AND-NOT logic gate is shown in FIGS. 9A-9D. As shown in FIG. 9A, this logic gate comprises a gate strand 116 (green) comprising a site (Input 1*) capable of binding to a first input strand 114 (red/Input 1). The gate strand 116 is initially bound to an output strand 115 (blue). The output strand 115 (blue) is substantially complementary to a reporter strand 118 (black), and additionally includes a site (Input 2*)

capable of binding to a second input strand 119 (fuschia/Input 2). The input-strand annealing portion of the gate strand 116 anneals to the first input strand 114 (red/Input 1) but not to the second input strand 119 (fuschia/Input 2). When only the second input strand 119 (fuschia/Input 2) is present, as shown in FIG. 9D, no reaction occurs. However, when only the first input strand 114 (red/Input 1) is present, as shown in FIG. 9C, the output strand 115 (blue) is displaced upon polymerization of the first input strand 114 (red/Input 1) and can be detected or used for signaling in downstream logic gates. In this example, the output strand 115 binds to a toehold region of reporter strand 118 (black), displacing quencher strand 117 (black), and producing a fluorescent signal. (The output strand 115 could alternatively bind to the quencher strand 117 (black) or to either a reporter strand or a quencher strand of a polymerase-dependent reporter gate, depending on the desired format.) When the second input strand 119 (fuschia/Input 2) is also present, as in FIG. 9B, the output strand 115 anneals to the second input strand 119 (fuschia/Input 2), and reporter strand 118 (black) is displaced from output strand 115 upon polymerization of the second input strand 119 (fuschia/Input 2). Displaced reporter strand 118 then binds to displaced quencher strand 117, removing the fluorescent signal.

Figure 10:
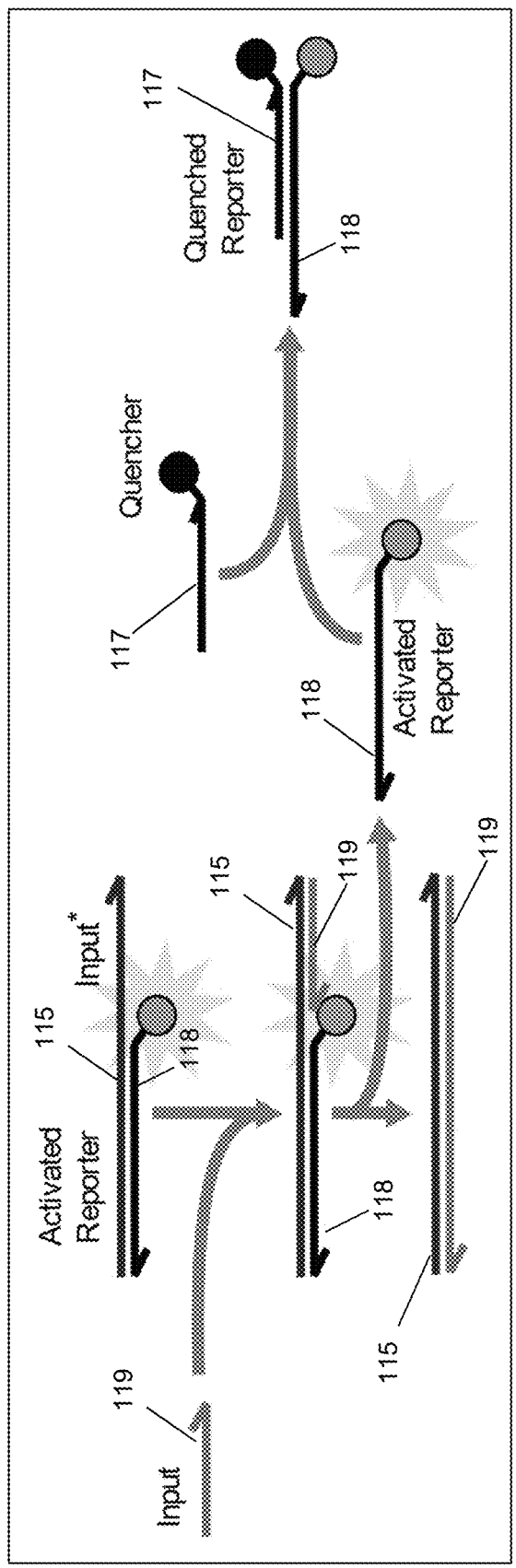
FIG. 10 shows a schematic of an exemplary polymerase-dependent logic gate employing a NOT logical operation. The half arrowheads indicate 3' ends of depicted nucleic acid strands.

Another exemplary polymerase-dependent NOT logic gate is shown in FIG. 10. This logic gate comprises an activated output complex comprising a reporter strand 118 (black) serving as an output strand and a gate strand 115 (blue). The gate strand 115 (blue) is substantially complementary to input strand 119 (fuschia) at portion Input*. In its initial state, reporter strand 118 is not bound to a quenching moiety and therefore yields a fluorescent signal. When input strand 119 binds output strand 115, it displaces reporter strand 118 upon polymerization. Displaced reporter strand 118 can then bind to quencher strand 117 (black), which can be referred to as a "NOT strand," to quench the fluorescent signal. In this example, strands 118 and 117 comprise a fluorophore-quencher reporter complex, but in principle this NOT operation can act on any reversible logic gate or output strand, wherein strands 118 and 117 could be devoid of a fluorophore or quencher, strand 117 could constitute an output strand from another gate or any other strand substantially complementary to strand 118, and binding of strand 118 with strand 117 would effectively quarantine strand 118 and prevent downstream signaling. Similar to the embodiment above, the output strand 115 could alternatively bind to the quencher strand 117 (black) or to either a reporter strand or a quencher strand of a polymerase-dependent reporter gate, thereby making the initially non-bound member of the reporter gate the NOT strand.

Exemplary lengths of the gate strand in the polymerase-dependent logic gates include lengths of from about 4, about 10, about 15, about 20, about 25, about 30, about 35, about 40, about 45, about 50 or more nucleotide bases to about 10, about 15, about 20, about 25, about 30, about 35, about 40, about 45, about 50, about 60, about 70, about 80, about 90, about 100, about 150, about 200, about 250, about 300 or more nucleotide bases.

Exemplary lengths of the output-strand annealing portion of the gate strand in the polymerase-dependent logic gates include lengths of from about 2, about 4, about 10, about 15, about 20, about 25, about 30, about 35, about 40, about 45, about 50 or more nucleotide bases to about 5, about 10, about 15, about 20, about 25, about 30, about 35, about 40, about 45, about 50, about 60, about 70, about 80, about 90, about 100, about 150, about 200, about 250, about 300 or more nucleotide bases.

Exemplary lengths of the output-strand non-annealing portion of the gate strand in the polymerase-dependent logic gates include lengths of from about 1, about 2, about 4, about 10, about 15, about 20, about 25, about 30, about 35, about 40, about 45, about 50 or more nucleotide bases to about 5, about 10, about 15, about 20, about 25, about 30, about 35, about 40, about 45, about 50, about 60, about 70, about 80, about 90, about 100, about 150, about 200, about 250, about 300 or more nucleotide bases.

Exemplary lengths of the input-strand annealing portion of the gate strand in the polymerase-dependent logic gates include lengths of from about 1, about 2, about 4, about 10, about 15, about 20, about 25, about 30, about 35, about 40, about 45, about 50 or more nucleotide bases to about 5, about 10, about 15, about 20, about 25, about 30, about 35, about 40, about 45, about 50, about 60, about 70, about 80, about 90, about 100, about 150, about 200, about 250, about 300 or more nucleotide bases.

Exemplary lengths of the output strand in the polymerase-dependent logic gates include lengths of from about 2, about 4, about 10, about 15, about 20, about 25, about 30, about 35, about 40, about 45, about 50 or more nucleotide bases to about 5, about 10, about 15, about 20, about 25, about 30, about 35, about 40, about 45, about 50, about 60, about 70, about 80, about 90, about 100, about 150, about 200, about 250, about 300 or more nucleotide bases.

Figure 11:
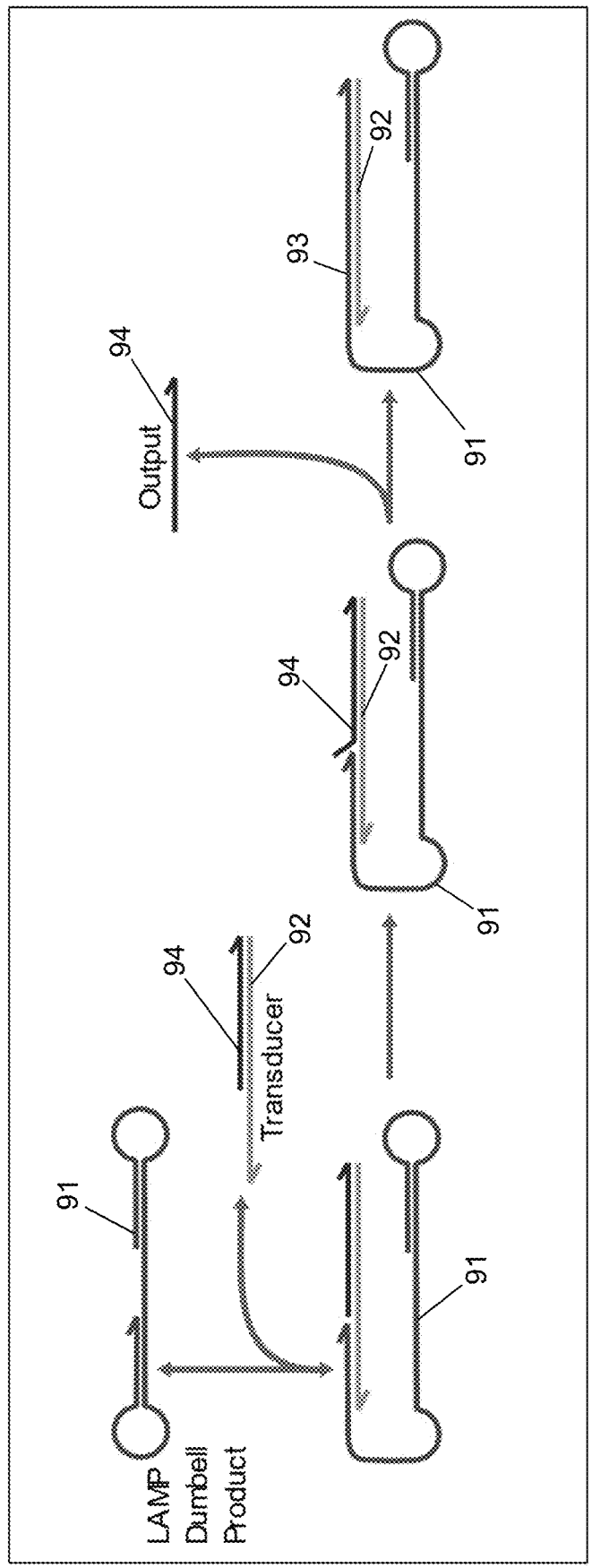
FIG. 11 shows a schematic of an exemplary polymerase-dependent logic gate employing a YES logical operation that uses the 3' end of a LAMP dumbbell product as an input. The half arrowheads indicate 3' ends of depicted nucleic acid strands.

The input strand in any polymerase-dependent logic gate can comprise a species of the amplified nucleic acid or can comprise an output strand from an upstream logic gate in the circuit. When employing LAMP, for example, the input strand can comprise a LAMP amplification product, such as a portion of a LAMP dumbbell product. A 3' portion of the LAMP dumbbell product, for example, can bind to the input-strand annealing portion of a gate strand. A schematic of such a mechanism is shown in FIG. 11, wherein a LAMP dumbbell product 91 serves as an input strand. A 3' portion of the LAMP dumbbell product 91 binds to and extends along a gate strand 92 to generate an extended input strand 93, thereby displacing an output strand 94 from the gate strand 92.

The output strand in any polymerase-dependent logic gate can comprise an input strand for a downstream logic gate or an input strand for a reporter gate.

A reporter gate configured to detect an output strand can comprise a branch migration-mediated strand displacement reporter as shown in FIG. 2 or a polymerase-dependent reporter gate. A polymerase-dependent reporter gate can be generated by placing a fluorophore on the gate strand 42 (such as on the 5' end) and a quencher on the output strand 43 (such as on the 3' end) of a polymerase-dependent logic gate as shown in FIG. 4, thereby generating a reporter strand and a quencher strand. Alternatively, a polymerase-dependent reporter gate can be generated by placing a fluorophore on the output strand 43 (such as on the 5' end) and a quencher on the gate strand 42 (such as on the 3' end) of a polymerase-dependent logic gate as shown in FIG. 4, thereby generating a reporter strand and a quencher strand. In either case, binding and polymerase-mediated extension of an input strand will displace the quencher strand from the reporter strand and permit fluorescence to be detected from the fluorophore.

As used herein, "identical" refers to nucleic acid sequences that are the same. "Substantially identical" refers to nucleic acids sequences that are identical or sufficiently identical as to bind to a same third nucleic acid sequence under conditions suitable for enzyme-dependent isothermal amplification, such as loop-mediated isothermal amplification (LAMP). Substantial identity therefore encompasses identity, and any embodiment described herein as having substantial identity can therefore have identity. "Complementary" refers to nucleic acid sequences that have perfect base pairing. "Substantially complementary" refers to nucleic acid sequences that have perfect base pairing (complementarity) or sufficient base pairing as to bind to each other under conditions suitable for enzyme-dependent isothermal amplification, such as LAMP. Substantial complementarity therefore encompasses complementarity, and any embodiment described herein as having substantial complementarity can therefore have complementarity (perfect base pairing). In any embodiment described herein, the identity, substantial identity, complementarity or substantial complementarity can occur over a length of 2-200 bases or more, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 60, at least 70, at least 80, at least 90, at least 100, at least 110, at least 120, at least 130, at least 140, at least 150, at least 160, at least 170, at least 180, or at least 190 to at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 60, at least 70, at least 80, at least 90, at least 100, at least 110, at least 120, at least 130, at least 140, at least 150, at least 160, at least 170, at least 180, at least 190, at least 200 or more bases.

In the methods described herein, the isolating can occur prior to the lysing, the lysing can occur prior to the amplifying, and/or the amplifying can occur prior to the detecting. In preferred versions, the liquid droplet remains at a substantially constant volume throughout and between each of the lysing, the amplifying, and the detecting. In preferred versions, the lysing, the amplifying, and the detecting all occur without diluting the liquid droplet, adding additional reagents to the liquid droplet, and/or removing reagents or liquid from the liquid droplet after the isolating.

The lysing, the amplifying, and/or the molecular logical computation in some versions are performed at substantially the same temperature. "Substantially same temperature" refers to a temperature range spanning about 50° C., about 45° C., about 40° C., about 35° C., about 30° C., about 25° C., about 20° C., about 20° C., about 15° C., about 10° C., about 5° C. or less.

The lysing, the amplifying, and/or the molecular logical computation in some versions are performed at a substantially constant temperature. "Substantially constant temperature" refers to temperature maintained over time within a range of about 50° C., about 45° C., about 40° C., about 35° C., about 30° C., about 25° C., about 20° C., about 20° C., about 15° C., about 10° C., about 5° C. or less.

In some versions, a substantially constant temperature is maintained throughout and between each of the lysing, the amplifying, and/or performing the molecular logical computation.

The lysing, the amplifying, and the molecular logical computation in some versions are performed at a temperature of from about 45° C., about 50° C., about 55° C., or about 60° C. to about 70° C., about 75° C., about 80° C., about 85° C., or about 90° C.

The methods described herein can be used to profile a number of aspects of the nucleic acid composition of a single cell using the cell's RNA or DNA as a nucleic acid template. The methods, for example, can be used in expression profiling to characterize the expression pattern of the cell's mRNA or miRNA. Certain cell types, such as circulating tumor cells (CTCs) or cells having particular lineages, have distinguishable expression patterns. See, e.g., Sieuwerts et al. 2011. The methods of the invention can be used to distinguish CTCs from non-CTCs, or cells of one lineage from cells of another lineage. The methods of the invention can also be used to detect certain genetic mutations in a cell, such as single nucleotide polymorphisms (SNPs) or other types of mutations. See, e.g., Yongkiettrakul et al. 2016 and Badolo et al. 2012 for appropriate LAMP primer design for detecting SNPs.

Figure 12:
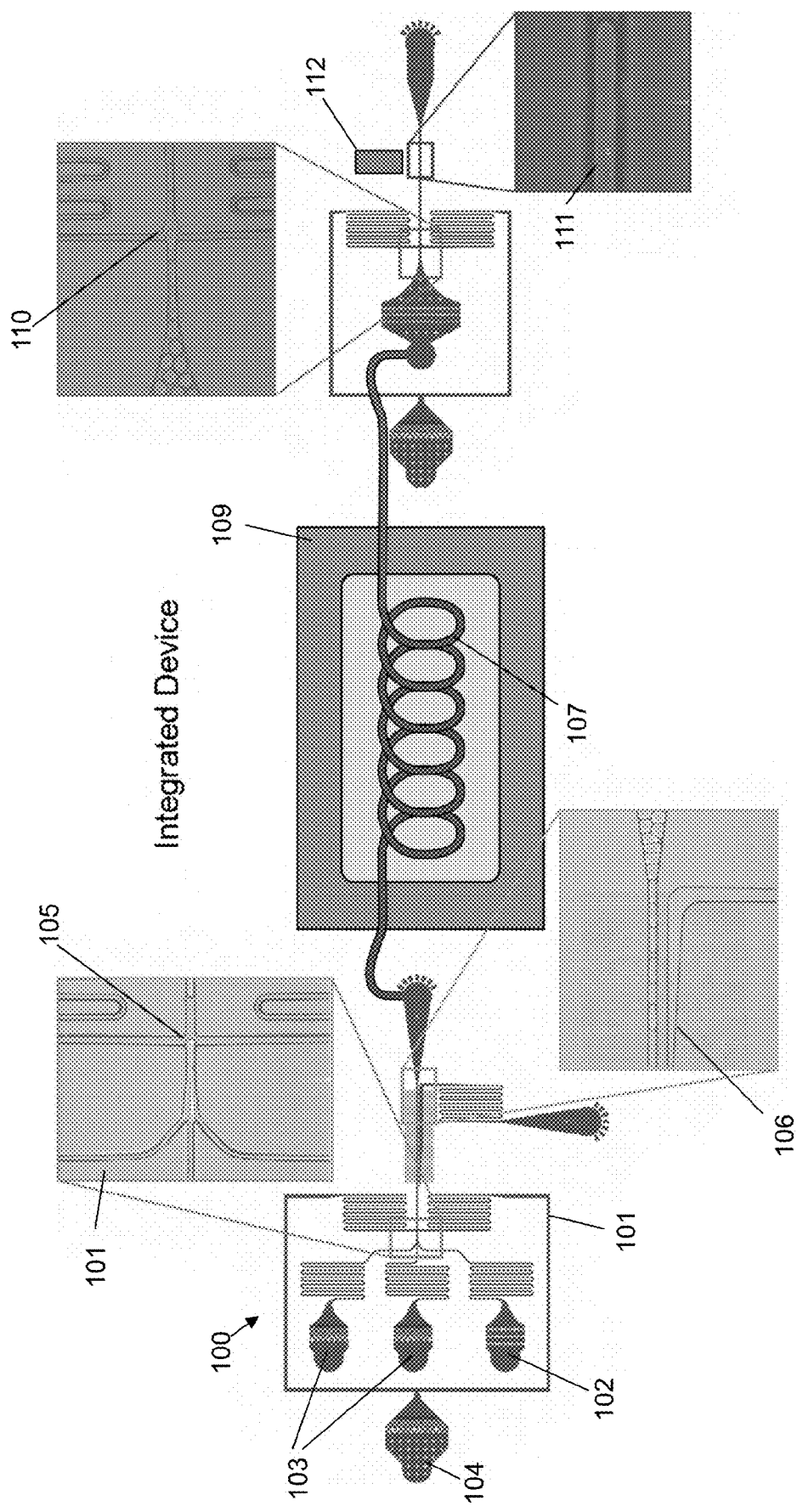
FIG. 12 shows an exemplary device suitable for performing the methods described herein.

An exemplary device 100 suitable for performing the methods described herein is shown in FIG. 12. The device 100 comprises a single, continuous network of microfluidic channels 101 and tubing 107, in combination with a number of additional elements. The additional elements include a cell-solution inlet 102, reagent-solution inlets 103, an oil inlet 104, a droplet former 105, an oil extractor 106, an incubation section comprising tubing 107 running through a heating element 109, an oil injector 110, a laser 111, and a fluorescence detector 112. Cell solution and reagent solutions are introduced in the channels via the cell-solution inlet 102 and the reagent-solution inlets 103, respectively. The cell solution can include any collection of cells desired to be profiled. The reagent solution can include any reagent described herein such as a lysis reagent, a DNA polymerase, amplification primers, deoxynucleotide triphosphates, RNAse inhibitors, one or more nucleic acid logic gates, and one or more reporters, or any other reagent. The device can optionally include more than one reagent-solution inlets 103, such as two, three, or more, for introducing the reagents separately (see the examples). The cell solution and reagent solution(s) merge upstream of the droplet former 105 to form a cell-and-reagent solution. The cell-and-reagent solution may comprise laminar flows of each of the cell solution and reagent solution(s). The cell-and-reagent solution flows to the droplet former 105. The droplet former 105 includes oil channels connected to the oil inlet 104 that inject oil perpendicularly into the aqueous flow. The injected oil separates the cell-and-reagent solution into aqueous droplets suspended in the oil. The droplets are then compacted in the oil by flowing past the oil extractor 106, which removes some of the oil surrounding the droplets using suction. The compacted droplets flow into the incubation section. The length of tubing section 107 determines the time each droplet spends in the incubation section to allow controlled cell lysis, nucleic acid template amplification, and logical computation with the nucleic acid logic gates. Heating of the tubing 107 by the heating element 109 facilitates the cell lysis and amplification. The heating element 109 may heat the entire device 100 or any sub-portion thereof, such as the incubation section. The droplets are then decompacted within the channel by virtue of the oil injector 110 injecting oil into the channel. This permits analysis of each individual liquid droplet without interference from other droplets and provides data acquisition software time to collect and process collected data. Activated reporters generated during the logical computation are then illuminated with the laser 111, and fluorescence is detected with the fluorescence detector 112. Droplet sorting can occur with a sorting device depending on the emitted fluorescence. The devices of the invention may include some or all of the exemplary elements described herein and may include others.

In some versions, the device 100 can be configured to split the droplets at any point after formation to increase throughput.

Figure 13:
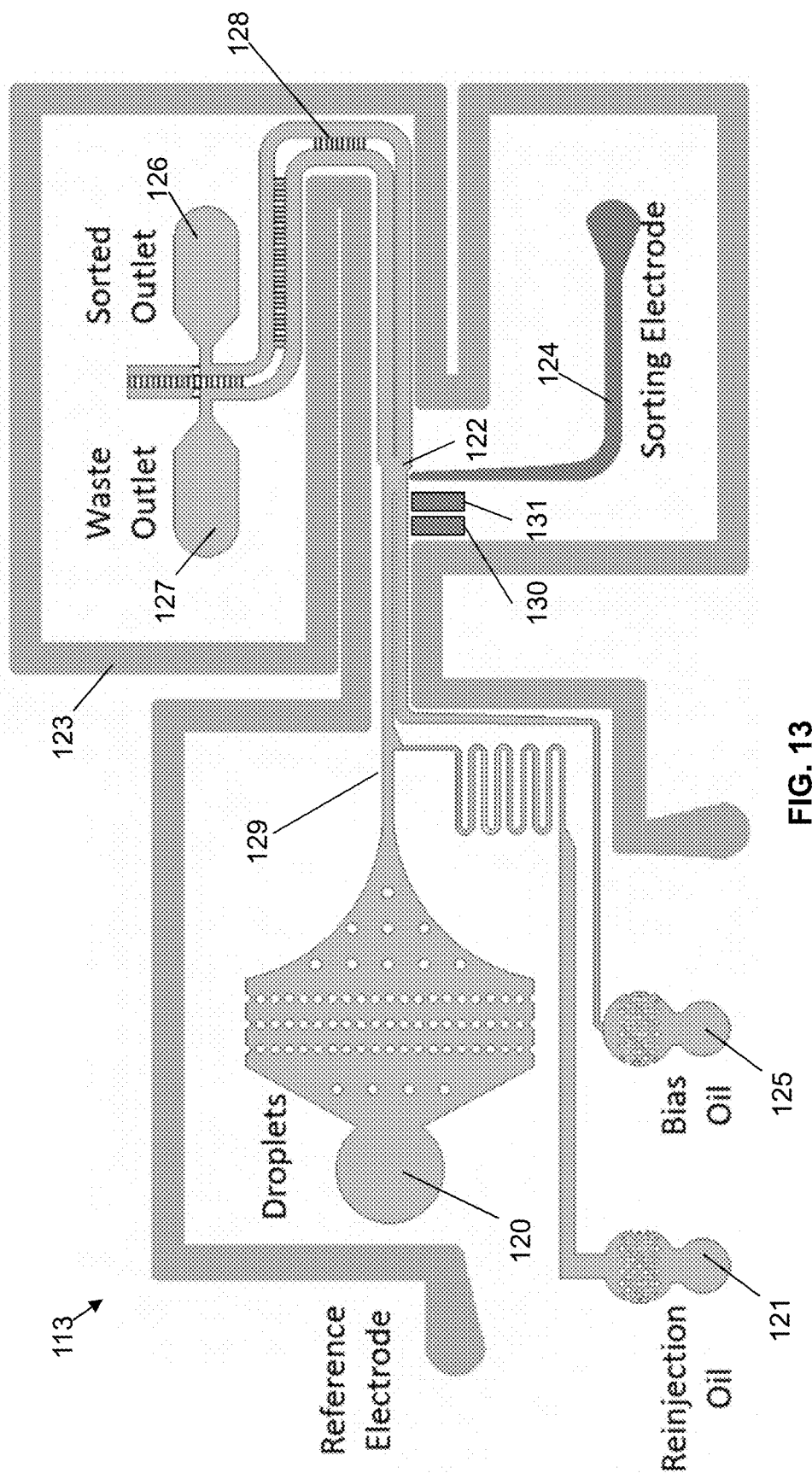
FIG. 13 shows an exemplary device for sorting droplets, as performed in the methods described herein.

An exemplary device 113 capable of sorting droplets is shown in FIG. 13. This device comprises a continuous network of microfluidic channels 129 suitable for processing droplets, as well as a set of liquid electrodes 123,124 capable of conducting electricity. Droplets first flow into injection port 120 and are spaced out by reinjecting oil via an additional port 121. Droplets pass through sorting junction 122 after having their fluorescence measured via laser(s) 130 and detector(s) 131. Based on their fluorescence, droplets are directed into sorted outlet 126 or waste outlet 127 through application of an electric field via liquid electrodes 123 and 124. Intermittent application of this field creates a dielectric force on the droplet, deflecting it into the sorted outlet 126. Sorting is tuned by the amplitude and frequency of DC current application between reference electrode 123 and sorting electrode 124. Bias oil, applied through inlet 125, also tunes sorting. Pressure relief shunts 128 equilibrate the oil pressure between the sorting outlet 126 and waste outlet 127, thereby preventing pressure fluctuations which can disrupt sorting.

Systems of the invention include any combination of elements described herein for performing the method steps recited herein.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Background

The following examples show aspects of the invention for profiling the nucleic acid composition of each individual cell within a large population of hematopoietic cells for detecting circulating tumor cells (CTCs) therein.

During cancer progression, cells detach from the primary tumor and disseminate throughout the blood stream. These CTCs serve as valuable biomarkers for real-time monitoring of carcinogenesis, and the methods described herein for detecting them provide a critical tool in cancer detection and treatment.

Detecting CTCs remains technically challenging due to their ultra-low abundance among normal hematopoietic cells and their highly heterogeneous phenotypes. The present invention provides a high-throughput platform for single-cell analysis that affords the ability to detect CTCs with high sensitivity and specificity.

The CTC analysis platform combines the specificity of molecular computation with the massive throughput of droplet-based microfluidics. Single cells are encapsulated in microdroplets containing a DNA-based logic circuit that inputs cellular transcripts, performs a logical computation, and outputs a fluorescence signal based on the cell's phenotypic state (FIG. 1). The microdroplets are generated, incubated, and analyzed on a microfluidic device that can process millions of cells per hour. This approach is highly scalable and can be applied to tens of RNA inputs, providing a detailed profile of a cell's phenotypic state.

Materials and Methods

Device Fabrication

Microfluidic devices were fabricated from polydimethylsiloxane (PDMS) via a soft photolithography process. SU-8 3025 or 3010 Photoresist (Microchem) was deposited onto a silicon wafer and spun to achieve the desired layer height. A photomask was used to create patterns of polymerized photoresist during UV exposure. The patterned wafer was then placed in a petri dish to form a mold, and Sylgard® 184 PDMS (Dow Corning, Cat. No. 4019862) in an 11:1 polymer:activator ratio was added. After polymerization, patterned PDMS was excised and bonded to a glass microscope slide via plasma treatment. Finally, Aquapel (Pittsburgh Glass Works) was applied to the channels to provide a hydrophobic coating.

DNA Complexes and Primer Mixes

All DNA oligos were ordered from Integrated DNA Technologies (Coralville, Iowa) using standard desalting, with the exception of reporter complex strands, which were HPLC purified. All LAMP primers were diluted in DNase/RNase-free water (Invitrogen Cat. No. 10977023) prior to storage at −20° C. Logic gate and reporter strands were diluted in DEPC-treated 10 mM Phosphate-Buffered Saline (pH 7.4) prior to storage at −20° C. 100× stocks of each DNA complex were prepared in diethyl pyrocarbonate (DEPC)-treated phosphate buffered phosphate buffered saline (PBS) and stored at −20° C. On the day of experiment, each DNA complex was separately annealed via heating to 97° C. for 5 minutes and cooling at a rate of −2° C./min to 23° C. DNA complexes were stored on ice until the time of experiment. 20×LAMP primer mixes were prepared in DNase/RNase-free water and stored at −20° C. Sequences of primers and logic gates used in LAMP experiments are shown in Table 1.

TABLE 1

Sequences of primers and logic gates used in LAMP experiments.

| Strand | Sequence | SEQ ID NO |
|---|---|---|
| KRT19 LAMP Primers | | |
| KRT19 LAMP-3 F3 | AGTGACATGCGAAGCCAAT | 3 |
| KRT19 LAMP-3 B3 | GCTTTCATGCTCAGCTGTGA | 4 |
| KRT19 LAMP-3 FIP | AGCGACCTCCCGGTTCAATTCTC GAGCAGAACCGGAAGGAT | 5 |
| KRT19 LAMP-3 BIP | CACACGGAGCAGCTCCAGATGTG CAGCTCAATCTCAAGACC | 6 |
| KRT19 LAMP-3 LF | TGGTGAACCAGGCTTCAGC | 7 |
| KRT19 LAMP-3 LB | AGGTCCGAGGTTACTGACCTGC | 8 |
| VIM LAMP Primers | | |
| VIM LAMP-2 F3 | CCGCACCAACGAGAAGG | 9 |
| VIM LAMP-2 B3 | TGGTTAGCTGGTCCACCT | 10 |
| VIM LAMP-2 FIP | TCCAGGAAGCGCACCTTGTCGGA GCTGCAGGAGCTGAA | 11 |
| VIM LAMP-2 BIP | AAGATCCTGCTGGCCGAGCTCCC GCATCTCCTCCTCGTAG | 12 |
| VIM LAMP-2 LF | AGTTGGCGAAGCGGTCA | 13 |
| VIM LAMP-2 LB | CAGCTCAAGGGCCAAGGCAA | 14 |
| ESR1 LAMP Primers | | |
| ESR1 LAMP-1 F3 | AGAGCTGCCAACCTTTGG | 15 |
| ESR1 LAMP-1 B3 | TGAACCAGCTCCCTGTCTG | 16 |
| ESR1 LAMP-1 FIP | GGCACTGACCATCTGGTCGGAAG CCCGCTCATGATCAAAC | 17 |
| ESR1 LAMP-1 BIP | TTGTTGGATGCTGAGCCCCCCCC ATCATCGAAGCTTCACT | 18 |
| ESR1 LAMP-1 LF | GCCAGGCTGTTCTTCTTAGAGC | 19 |
| ESR1 LAMP-1 LB | ACTCTATTCCGAGTATGATCCTA CC | 20 |
| GAPDH LAMP Primers | | |
| GAPDH LAMP-2 F3 | GCTGCCAAGGCTGTGG | 21 |
| GAPDH LAMP-2 B3 | CCCAGGATGCCCTTGAGG | 22 |
| GAPDH LAMP-2 FIP | GTTGGCAGTGGGGACACGGAAC AAGGTCATCCCTGAGCTGA | 23 |
| GAPDH LAMP-2 BIP | TGTCAGTGGTGGACCTGACCTGT CCGACGCCTGCTTCA | 24 |
| GAPDH LAMP-2 LF | GGCCATGCCAGTGAGCTT | 25 |
| GAPDH LAMP-2 LB | CGTCTAGAAAAACCTGCCAAATA TG | 26 |
| ACTB SNP Detection LAMP Primers | | |
| ACTB 4 B3-SNP | GGCTGGAAGAGTGCCGC | 27 |
| ACTB 4 F3 | GCGGCTACAGCTTCACCA | 28 |
| ACTB 4 FIP | CGTGGCCATCTCTTGCTCGAAGG GGAAATCGTGCGTGACATT | 29 |

TABLE 1-continued

Sequences of primers and logic gates used in LAMP experiments.

| Strand | Sequence | SEQ ID NO |
|---|---|---|
| ACTB 4 BIP | GCTTCCAGCTCCTCCCTGGACCGCTCATTGCCAATGGT | 30 |
| ACTB 4 LF | ACGTAGCACAGCTTCTCCTT | 31 |
| ACTB 4 LB | GAAGAGCTACGAGCTGCCT | 32 |
| ACTB 4 B3-Sink | GCGGCACTCTTCCAGCC | 33 |
| Reporter Complexes | | |
| RepF | 6-FAM-CGAGTGCTGCGTATGACAAGGGCTAGCGTT | 34 |
| RepF-HEX | HEX-CGAGTGCTGCGTATGACAAGGGCTAGCGTT | 35 |
| RepQ | CCCTTGTCATACGCAGCACTCG-IowaBlackFQ | 36 |
| RepF2-AF647 | AlexaFluor647-CGCCGCGTCCTGATCTAACTGACTGACTGC | 37 |
| RepQ2 | TCAGTTAGATCAGGACGCGGCG-IowaBlackRQ | 38 |
| Transducer Orthogonality Experiments | | |
| KRT19 -> Rep Transducer Gate | CGAGTGCTGCGTATGACAAGGGCTAGCGTTATGCTACGAGCGACCTCCCGGTTCAATTCT | 39 |
| KRT19 -> Rep Transducer Output | AACGCTAGCCCTTGTCATACGCAGCACTCG | 40 |
| VIM -> Rep Transducer Gate | CGAGTGCTGCGTATGACAAGGGCTAGCGTTATGCTACGTCCAGGAAGCGCACCTTGTC | 41 |
| VIM -> Rep Transducer Output | AACGCTAGCCCTTGTCATACGCAGCACTCG | 42 |
| Exemplary Logic Gates Corresponding to Gates Shown in FIGS. 5 and 6 | | |
| KRT19 AND VIM Strand 1 | CGAGTGCTGCGTATGACAAGGGCTAGCGTTATGCTACGTCCAGGAAGCGCACCTTGTCATGCTACGAGCGACCTCCCGGTTCAATTCT | 43 |
| KRT19 AND VIM Strand 2 | CGAGTGCTGCGTATGACAAGGGCTAGCGTTATGCTACGAGCGACCTCCCGGTTCAATTCTATGCTACGTCCAGGAAGCGCACCTTGTC | 44 |
| KRT19 OR VIM Gate | CGAGTGCTGCGTATGACAAGGGCTAGCGTTATGCTACGTCCAGGAAGCGCACCTTGTCATGCTACGAGCGACCTCCCGGTTCAATTCT | 45 |
| KRT19 OR VIM Output | AACGCTAGCCCTTGTCATACGCAGCACTCG | 46 |
| VIM F1 | GACAAGGTGCGCTTCCTGGA | 47 |
| KRT19 F1 | AGAATTGAACCGGGAGGTCGCT | 48 |

TABLE 1-continued

Sequences of primers and logic gates used in LAMP experiments.

| Strand | Sequence | SEQ ID NO |
|---|---|---|
| AND Gate with LAMP Inputs | | |
| KRT19 Transducer 2 Gate | CTGCTCTCACGGAGGCGCACCGG TAAGGGTCATCGATGAGCGACCT CCCGGTTCAATTCT | 49 |
| VIM Transducer 2 Gate | CTGCTCTCACGGAGGCGCACCGG TAAGGGTCATCGATGTCCAGGAA GCGCACCTTGTC | 50 |
| KRT19/VIM Transducer 2 Output | CGATGACCCTTACCGGTGCGCCT CCGTGAGAGCAG | 51 |
| KRT19 AND VIM Gate | CGAGTGCTGCGTATGACAAGGGC TAGCGTTATGCTGCTCTCACGG | 52 |
| KRT19 AND VIM Out | AACGCTAGCCCTTGTCATACGCA GCACTCG | 53 |
| KRT19 AND VIM Threshold | CCGCTGGTGATCACTCTGCTCTC ACGGAGGCGCACCGGTAAGGGT CATCG | 54 |
| OR Gate with LAMP Inputs | | |
| KRT19 Transducer 3 Gate | CGCGATCCGAGTGCTGCGTATGA CAAGGGCTAGCGTTTGCCGGAAG CGACCTCCCGGTTC | 55 |
| VIM Transducer 3 Gate | CGCGATCCGAGTGCTGCGTATGA CAAGGGCTAGCGTTTGCCGGATC CAGGAAGCGCACCT | 56 |
| KRT19/VIM Transducer 3 Output | TCCGGCAAACGCTAGCCCTTGTC ATACGCAGCACTCGGATCGCG | 57 |
| NOT/AND-NOT Gates with LAMP Inputs | | |
| VIM Transducer 4 Gate | CCATCGCGGAGACACGGACATCG TTAAGGCAGCCTGTAGGCAGCCT CCAGGAAGCGCACC | 58 |
| KRT19 Transducer 4 Gate | GTGTCTCCGCGATGGCGAGTGCT GCGTATGACAAGGGCTAGCGTTA GCGACCTCCCGGTT | 59 |
| KRT19 AND-NOT VIM Inhibitor | GGCTGCCTACAGGCTGCCTTAAC GATGTCCGTGTCTCCGCGATGG | 60 |
| KRT19 AND-NOT VIM Output | AACGCTAGCCCTTGTCATACGCA GCACTCGCCATCGCGGAGACAC | 61 |
| Transducer Orthogonality Experiments in Droplets | | |
| KRT19 -> Rep2 Transducer Gate | GTGTCTCCGCGATGGCGCCGCGT CCTGATCTAACTGACTGACTGCA GCGACCTCCCGGTT | 62 |
| KRT19 -> Rep2 Transducer Output | GCAGTCAGTCAGTTAGATCAGGA CGCGGCGCCATCGCGGAGACAC | 63 |
| VIM Transducer 3 Gate | CGCGATCCGAGTGCTGCGTATGA CAAGGGCTAGCGTTTGCCGGATC CAGGAAGCGCACCT | 56 |
| KRT19/VIM Transducer 3 Output | TCCGGCAAACGCTAGCCCTTGTC ATACGCAGCACTCGGATCGCG | 57 |

TABLE 2

Sequences of oligos used in CHA experiments.

| Strand | Sequence | SEQ ID NO |
|---|---|---|
| CK19 Sensor | GAGTTACCAGCCTGGAGTTCTCAATGGTGGCCTGGTAACTCACTGACCGAGCTAA | 64 |
| H1 | CGACATCTAACCTAGCTCACTGACCGAGCTAAGCTGTTCTCGATTAGCTCGGTCAGTGAGTTACCAG | 65 |
| H2 | GCTGTTCTCGATCACTGACCGAGCTAATCGAGAACAGCTTAGCTCG | 66 |
| H3 | GTCAGTGAGCTAGGTTAGATGTCGCCATGTGTAGACGACATCTAACCTAGCCCTTGTCATAGAGCAC | 67 |
| H4 | AGATGTCGTCTACACATGGCGACATCTAACCTAGCCCATGTGTAGA | 68 |
| RepF-CHA | 6-FAM-CGAGTGCTCTATGACAAGGGCTAGGTT | 69 |
| RepQ-CHA | CCCTTGTCATAGAGCACTCG-IowaBlackFQ | 70 |
| CK19 Input | GCCACCATTGAGAACTCCAGG | 71 |

In Vitro Transcription

DNA templates for KRT19 and VIM transcripts were synthesized as "gBlocks" (SEQ ID NO:72 and SEQ ID NO:73, respectively) by Integrated DNA Technologies (Coralville, Iowa) and cloned into a pET-22b(+) vector (available from Novagen, Cat. No. 69744-3) under a T7 promoter. In vitro transcription was performed with a HiScribe™ T7 High Yield RNA Synthesis Kit (New England Biolabs, Cat. No. E2040S), and resulting RNA was purified using a GeneJET RNA Purification Kit (Thermo Scientific, Cat. No. K0731). RNA concentration was quantified on a NanoDrop™ Spectrophotometer (Thermo Scientific) and stocks were stored at −80° C. in DEPC-treated PBS.

Cell Culture and Staining

MOLT-4 cells (American Type Culture Collection) were subcultured in a 1:8 ratio every two days and grown in RPMI-1640 Medium (Gibco, Cat. No. 11875093) supplemented with 10% FBS (Gibco, Cat. No. 10082147) and 1× Antibiotic-Antimycotic (Gibco, Cat. No. 15240062). SK-BR-3, U-2 OS, and MCF7 cells (American Type Culture Collection) were subcultured in a 1:4 ratio every two days and grown in DMEM, high glucose (Gibco, Cat. No. 11965-092) supplemented with 10% FBS and 1× Antibiotic-Antimycotic. On the day of experiment, each cell type was collected and washed twice with Dulbecco's Phosphate-Buffered Saline (DPBS) (Gibco, Cat. No. 14190144). Cells were then stained on ice using either 1 µM CellTrace™ Calcein Red-Orange AM (Invitrogen, Cat. No. C34851), 1 µM CellTrace™ Calcein Violet AM for 405 nm Excitation (Invitrogen, Cat. No. C34858), or 0.6 µM Calcein AM (BD Biosciences, Cat. No. 564061) in DPBS for 30 minutes. Cells were subsequently washed twice with DPBS and resuspended in 18.75% v/v Optiprep™ Density Gradient Medium (Sigma Aldrich, Cat. No. D1556) in DPBS for microfluidic assays.

Batch RT-LAMP Experiments

Batch RT-LAMP assays were performed in triplicate on a BioRad CFX Connect at 65° C. Reactions were prepared at a total volume of 10 with 1.6 µM each FIP/BIP primer, 0.2 µM each F3/B3 Primer, 0.4 µM each LoopF/B Primer, 1× WarmStart LAMP Master Mix (New England Biolabs, Cat. No. E1700S), 0.5 U/µL SUPERase•In™ RNase Inhibitor (Invitrogen, Cat. No. AM2696), and 0.5× Phosphate Buffered Saline. DNA complexes were added at varying concentrations. LAMP primer and logic gate sequences are shown in Table 1. In reactions without any DNA complexes, LAMP Fluorescent Dye (New England Biolabs) was added as a general LAMP indicator. In lysate experiments, 1% Triton X-100 (Sigma Aldrich, Cat. No. T8787) was included in the reaction mixture. Intact, unstained cells were added to each well immediately before the start of each experiment. For all experiments, "standard concentrations" of LAMP primers are defined as 1.6 µM of each FIP/BIP primer, 0.2 µM of each F3/B3 Primer, and 0.4 µM of each LoopF/B Primer for a given LAMP primer set.

Transducer Orthogonality Experiments

Experiments were performed in triplicate as described above in "Batch RT-LAMP Experiments," with slight modifications. Each reaction included two LAMP primer sets: one specific to a KRT19 transcript, and another specific to a VIM transcript. Only one transducer was added to each reaction, recognizing either VIM or KRT19 amplification products. In vitro transcribed KRT19 or VIM RNAs were added to each reaction at a concentration of 10 nM. PBS was also added in non-template control reactions for each transducer. Each reaction included 400 nM transducer gate strand pre-annealed to 200 nM transducer output strand, and 200 nM reporter quenching strand pre-annealed to 100 nM reporter fluorophore strand. Logic gate and LAMP primer sequences are shown in Table 1.

AND Logic Gate Experiment with LAMP Inputs

Experiments were performed in triplicate, similarly to "Batch RT-LAMP Experiments." Each reaction included both KRT19 and VIM LAMP primer sets at standard concentrations (as defined in "Batch RT-LAMP Experiments"). In vitro transcribed KRT19 and/or VIM RNAs were added at 10 nM concentrations. Each reaction also contained 50 nM RepF pre-annealed to 100 nM RepQ. Every reaction included both KRT19 and VIM transducers: 60 nM KRT19 Transducer 2 pre-annealed to 120 nM KRT19/VIM Transducer 2 Output, and 60 nM VIM Transducer 2 pre-annealed to 120 nM KRT19 I VIM Transducer 2 Output. Each reaction contained 55 nM KRT19 AND VIM Output strand pre-annealed to 60 nM KRT19 AND VIM Gate strand. In KRT19 AND VIM logic experiments, the KRT19 AND VIM Threshold strand was included at 65 nM. All LAMP primer and logic strand sequences are given in Table 1.

OR Logic Gate Experiment with LAMP Inputs

Each reaction included both KRT19 and VIM LAMP primer sets at standard concentrations (as defined in "Batch RT-LAMP Experiments"). In vitro transcribed KRT19 and/or VIM RNAs were added at 1 nM concentrations, or an equivalent volume of water as a non-template control. Each reaction contained 100 nM RepF pre-annealed to 200 nM RepQ, 220 nM KRT19 Transducer 3 pre-annealed to 200 nM KRT19/VIM Transducer 3 Output, and 220 nM VIM Transducer 3 pre-annealed to 200 nM KRT19/VIM Transducer 3 Output. Experiments were performed in triplicate, as described in "Batch RT-LAMP Experiments." All LAMP primer and logic strand sequences are given in Table 1.

YES Logic Gate Experiment with LAMP Inputs

Each reaction included the KRT19 primer set at standard concentrations (as defined in "Batch RT-LAMP Experiments"). In vitro transcribed KRT19 RNA was added at 1 nM concentrations, or an equivalent volume of water as a non-template control. Each reaction contained 100 nM RepF pre-annealed to 200 nM RepQ, and 220 nM KRT19 Transducer 3 pre-annealed to 200 nM KRT19/VIM Transducer 3

Output. Experiments were performed in triplicate, as described in "Batch RT-LAMP Experiments." All LAMP primer and logic strand sequences are given in Table 1.

NOT Logic Gate Experiment with LAMP Inputs

Each reaction included 200 nM KRT19 AND-NOT VIM Output pre-annealed to 100 nM RepF, 240 nM VIM Transducer 4 Gate pre-annealed to 220 nM KRT19 AND-NOT VIM Inhibitor, and 200 nM unbound RepQ. Each reaction also included the VIM LAMP primer set at standard concentrations (as defined in "Batch RT-LAMP Experiments"). 1 nM VIM in vitro transcribed RNA was added, or water as a negative control. Experiments were performed in triplicate as described in "Batch RT-LAMP Experiments."

AND-NOT Logic Gate Experiment with LAMP Inputs

Each reaction included 220 nM KRT19 Transducer 4 Gate pre-annealed to 200 nM KRT19 AND-NOT VIM Output, 240 nM VIM Transducer 4 Gate pre-annealed to 220 nM KRT19 AND-NOT VIM Inhibitor, and 200 nM RepQ pre-annealed to 100 nM RepF. Each reaction also included the KRT19 and VIM LAMP primer set at standard concentrations (as defined in "Batch RT-LAMP Experiments"). 1 nM KRT19 and/or VIM in vitro transcribed RNA was added, or water as a negative control. Experiments were performed in triplicate as described in "Batch RT-LAMP Experiments."

Droplet RT-LAMP Experiments with dsDNA-Specific Reporter

Experiments were performed as described above in "Droplet RT-LAMP Experiments with Fluorogenic Logic Gate Reporter," with some modifications. Prior to the experiment, MOLT-4 and SK-BR-3 cells were stained separately with Calcein Red-Orange AM (Invitrogen), as described above in "Cell Culture and Staining." A coflow microfluidic dropmaker with 100 μM square channels was used to generate droplets approximately 1 nL in volume. The dropmaker combined three inlets containing:

1.) A 4× mixture of cells (900 cells/μL), suspended in an 18.75% v/v mixture of Optiprep™ Density Medium (Sigma Aldrich, Cat. No. D1556) and Phosphate Buffered Saline,
2.) 2× WarmStart LAMP Master Mix (New England Biolabs, Cat. No. E1700S),
3.) A 4× mixture containing LAMP primers, SUPERase•In™ RNase Inhibitor (Invitrogen, Cat. No. AM2696), 4× WarmStart LAMP Fluorescent Dye (New England Biolabs), and 4% v/v Triton X-100 (Sigma Aldrich Cat. No. T8787).

These aqueous flows were combined into droplets suspended in fluorinated oil (QX200™ Droplet Generation Oil for EvaGreen (Bio Rad, Cat. No. 1864005)). Flow rates were 50 μL/hour for inlets 1 and 3, 100 μL/hour for inlet 2, and 800 μL/hour for the oil inlet. The cell concentration (3,600 cells/μl) was chosen such that approximately one in every ten droplets contained a single cell. For microscopy experiments, droplets were collected into a microcentrifuge tube and incubated at 65° C. for 20 minutes prior to fluorescence measurements. Droplets were placed into a PDMS imaging chamber and imaged on a Nikon Eclipse Ti Epifluorescence Microscope.

Final RT-LAMP conditions included 1.6 μM each FIP/BIP primer, 0.2 μM each F3/B3 Primer, 0.4 μM each LoopF/B Primer, 1× WarmStart LAMP Master Mix (New England Biolabs), 0.5 U/μL SUPERase•In™ RNase Inhibitor (Invitrogen), 1% Triton X-100 (Sigma Aldrich), 4.7% v/v Optiprep™ Density Gradient Medium (Sigma Aldrich), 1× LAMP Fluorescent Dye (New England Biolabs), and 0.5× Phosphate Buffer.

Droplet RT-LAMP Experiments with Multiplexed Transducers

A coflow microfluidic dropmaker was used to encapsulate cells with LAMP components, logic gates, and lysis reagents. Prior to the experiment, U-2 OS and SK-BR-3 cells were stained separately with Calcein AM (BD Biosciences, Cat. No. 564061), as described above in "Cell Culture and Staining." 60 μm was chosen as the microfluidic channel width and height, generating droplets approximately 250 pL in volume. This dropmaker combined three aqueous inlets containing:

1.) A 10× mixture of cells (5,000 cells/μL), suspended in Phosphate Buffered Saline,
2.) 2× WarmStart LAMP Master Mix (New England Biolabs, Cat. No. E1700S),
3.) A 2.5× mixture containing LAMP primers, DNA complexes, SUPERase•In™ RNase Inhibitor (Invitrogen, Cat. No. AM2696), and 6.25% v/v Tween-20 (Sigma Aldrich Cat. No. P9416).

These aqueous flows were combined into droplets suspended in fluorinated oil (QX200™ Droplet Generation Oil for EvaGreen (Bio Rad, Cat. No. 1864005)). Flow rates were 80 μL/hour for inlet 1, 400 μL/hour for inlet 2, 320 μL/hour for inlet 3, and 1200 μL/hour for the oil inlet. The cell concentration (5,000 cells/μL) was chosen such that approximately one in every ten droplets contained a single cell. Droplets were collected into a microcentrifuge tube on ice and incubated at 65° C. for 60 minutes or 5 minutes (for negative controls) prior to fluorescence measurements. Droplets were then re-injected into a second microfluidic device for fluorescence measurements, with a droplet injection rate of 400 μL/hour and an oil reinjection rate of 1,200 μL/hour. Each droplet passed a set of lasers (Changchun New Industries Optoelectronics Tech. Co., Changchun, China) with 488 nm, 530 nm, and 637 nm excitation wavelengths, and fluorescence was measured via one photomultiplier tube (ThorLabs, Newton, N.J.) per channel. Fluorescence data was acquired via an FPGA card (National Instruments) and analyzed with LabView software (National Instruments).

Each condition included KRT19 and VIM primer sets, as listed in Table 1. Final RT-LAMP conditions included 1.6 μM each FIP/BIP primer, 0.2 μM each F3/B3 Primer, 0.4 μM each LoopF/B Primer, 100 nM RepF-HEX strand pre-annealed to 200 nM RepQ strand, 100 nM RepF2-AF647 strand pre-annealed to 200 nM RepQ2 strand, 110 nM KRT19→Rep Transducer Gate strand pre-annealed to 100 nM KRT19→Rep Transducer Output, 110 nM VIM→Rep Transducer Gate pre-annealed to 100 nM VIM→Rep Transducer Output, 1× WarmStart LAMP Master Mix (New England Biolabs), 0.5 U/μL SUPERase•In™ RNase Inhibitor (Invitrogen), and 2.5% v/v Tween-20 (Sigma Aldrich Cat. No. P9416).

Droplet ESR1 RT-LAMP

Experiments were carried out as in "Droplet RT-LAMP Experiments with Multiplexed Transducers," with some alterations. MCF7 and SK-BR-3 cells were stained separately with Calcein Red-Orange AM (Invitrogen), as described above in "Cell Culture and Staining." Cells were loaded into the device at a concentration of 9,000 cells/μL in Phosphate Buffered Saline with 125 pg/μL RNase A (Thermo Scientific, Cat. No. EN0531). Each condition included the ESR1 LAMP primer set at standard concentrations (as defined in "Batch RT-LAMP Experiments"). ESR1 LAMP primer sequences are listed in Table 1. Warmstart LAMP Dye (New England Biolabs) was added into inlet 3 as a general LAMP indicator. Final RT-LAMP conditions included 1× WarmStart LAMP Master Mix (New England Biolabs) with 1× WarmStart LAMP Dye, 0.5 U/μL SUPERase•In™ RNase Inhibitor (Invitrogen), and 2.5% v/v Tween-20 (Sigma Aldrich Cat. No. P9416). Droplets were collected on ice, incubated at 65° C. for 50 minutes, and fluorescence was measured using 473 nm and 532 nm lasers (Changchun New Industries Optoelectronics Tech. Co.) for excitation, similarly to the above experiment. Flow rates for droplet generation were 40 μL/hour for inlet 1, 100 μL/hour for inlet 2, 80 μL/hour for inlet 3, and 800 μL/hour for the oil inlet.

Droplet RT-LAMP with Integrated Device

Experiments were carried out as in "Droplet ESR1 RT-LAMP," with some alterations. MOLT-4 cells were stained with Calcein Red-Orange AM (Invitrogen), as described above in "Cell Culture and Staining." Cells were loaded into the device at a concentration of 9,000 cells/μL in Phosphate Buffered Saline. Each condition included the GAPDH LAMP primer set at standard concentrations (as defined in "Batch RT-LAMP Experiments"). Primer sequences are listed in Table 1. Final RT-LAMP conditions included 1× WarmStart LAMP Master Mix (New England Biolabs) with 1× WarmStart LAMP Dye, 0.5 U/μL SUPERase• In™ RNase Inhibitor (Invitrogen), and 2.5% v/v Tween-20 (Sigma Aldrich Cat. No. P9416). Droplets were generated, incubated, and analyzed in a single integrated device as shown in FIG. 12. Droplets travelled out of the droplet generator into a length of PE tubing (Scientific Commodities, Inc., Lake Havasu City, Ariz.), after having excess oil extracted for tight droplet packing. The PE tubing length was such that droplets spent 45 minutes within a 65° C. incubator before being reinjected into a microfluidic device for fluorescence measurement. Droplets were excited with 473 nm and 532 nm lasers, and data was acquired and analyzed similarly to the above experiment. Flow rates for droplet generation were 20 μL/hour for inlet 1, 50 μL/hour for inlet 2, 40 μL/hour for inlet 3, and 400 μL/hour for the oil inlet. Oil was subsequently extracted at 390 μL/hour and reinjected at 200 μL/hour prior to droplet measurement.

Catalyzed Hairpin Assembly Experiments

Catalyzed Hairpin Assembly (CHA) was performed in 10 μL reactions at 37° C. on a Tecan Spark plate reader. Fluorescence was measured with an excitation wavelength of 490 nm and an emission wavelength of 535. The reaction buffer consisted of TENaK (20 mM Tris, 1 mM EDTA, 140 mM NaCl, and 5 mM KCl, pH 8.0) plus 0.5% SDS. Each reaction contained DNA oligos including 50 nM H1, 400 nM H2, 50 nM H3, 400 nM H4, 10 nM CK19 Sensor, and 50 nM RepF-CHA pre-annealed to 100 nM RepQ-CHA. Oligos were separately annealed as described in "DNA Complexes and Primer Mixes," except for RepF-CHA and RepQ-CHA, which were annealed together. Sequences of each oligo are given in Table 2. For CHA background experiments, reactions were performed in triplicate with or without 100 pM of the DNA oligo "CK19 Input" present to initiate the reaction. Reactions proceeded for 12 hours.

For lysate inhibition experiments, MOLT-4 cells were titrated into the LAMP reactions with final concentrations ranging from $3.9*10^5$ cells/μL to $1.0*10^8$ cells/μL. In "CK19+" reactions, 10 nM of the DNA oligo "CK19 Input" was added to initiate the reaction, otherwise no initiator was added. Reactions proceeded for 8 hours.

Droplet Sorting Experiments

Droplets were generated similarly to the methods used in "Droplet ESR1 RT-LAMP" above, with some alterations. MCF7 cells were stained with Calcein Red-Orange AM (Invitrogen) and SK-BR-3 cells were stained separately with Calcein Violet AM (Invitrogen), as described above in "Cell Culture and Staining." Cells were mixed in a 1:1 ratio and loaded into the device at a concentration of 9,000 cells/μL total in Phosphate Buffered Saline. Each condition included the ESR1 LAMP primer set at standard concentrations (as defined in "Batch RT-LAMP Experiments"). Primer sequences are listed in Table 1. Warmstart LAMP Dye (New England Biolabs) was added into inlet 3 as a general LAMP indicator. Final RT-LAMP conditions included 1× WarmStart LAMP Master Mix (RNA & DNA) (New England Biolabs) with 1× WarmStart LAMP Dye, 0.5 U/μL SUPERase•In™ RNase Inhibitor (Invitrogen), and 2.5% v/v Tween-20 (Sigma Aldrich Cat. No. P9416). Flow rates for droplet generation were 40 μL/hour for inlet 1, 100 μL/hour for inlet 2, 80 μL/hour for inlet 3, and 800 μL/hour for the oil inlet. Droplets were collected on ice, incubated at 65° C. for 1 hour, and loaded into a sorting device as shown in FIG. 13. See also (Sciambi and Abate 2015). Sorting flow rates were 100 μL/hour for droplets, 400 μL/hour for reinjection oil, and 1,000 μL/hour for bias oil. Fluorescence was measured using 405 nm, 473 nm, and 532 nm lasers (Changchun New Industries Optoelectronics Tech. Co.) for excitation, similarly to the above experiment. Droplets were sorted based on high fluorescence in the LAMP dye channel (473 nm excitation). Each sorting pulse was applied through the sorting (positive) and reference (negative) electrodes using a 10 kHz square wave, with 800V amplitude and 250 burst cycles, generated by a Trek model 2210 high voltage amplifier (Trek Inc., Lockport, N.Y.). Sorting and reference electrodes were filled with 1M NaCl dissolved in de-ionized water. After sorting, droplets were placed into a PDMS imaging chamber and imaged on a Nikon Eclipse Ti Epifluorescence Microscope.

ACTB SNP-LAMP Detection Experiments

Experiments were performed in duplicate similarly to the methods used in "Batch RT-LAMP Experiments" above, with some modifications. Total RNA was extracted from MOLT-4 or SK-BR-3 cells using a GeneJET RNA Purification Kit (Thermo Scientific, Cat. No. K0731) and was added at a final concentration of 1 ng/μL. ACTB LAMP primers were added at standard concentrations (as defined in "Batch RT-LAMP Experiments"). Additionally, 1 μM "ACTB 4 B3-Sink" strand was added. All oligo sequences can be found in Table 1. Warmstart LAMP Dye (New England Biolabs) was added as a general LAMP indicator.

RESULTS

DNA-Based CTC Detection Circuit

The following examples show a DNA-based circuit that inputs multiple cellular transcripts, performs a logical computation, and outputs a binary CTC classification. Early experiments indicated that DNA strand displacement cascades were insufficient to detect transcript levels from single cells and therefore required an input amplification step. We therefore sought to develop amplification mechanisms that are sensitive, selective, and resistant to high lysate concentrations.

Figure 14A:
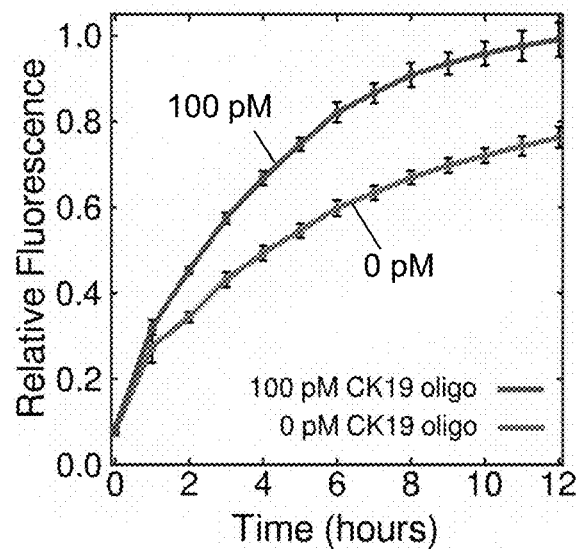
FIGS. 14A and 14B show effects of lysate on catalytic hairpin assembly (CHA) amplification.
Figure 14B:
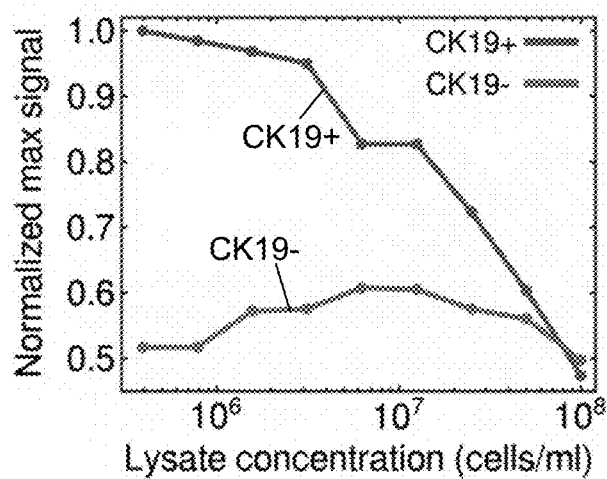

Signal amplification: We initially explored a catalytic hairpin assembly (CHA) amplification mechanism. CHA uses an input nucleic acid as a catalyst to assemble metastable hairpins, resulting in linear signal amplification. CHA amplification suffered from high signal background and strong cell lysate inhibition (FIGS. 14A and 14B). After thorough characterization, we concluded that CHA was insufficient to amplify transcripts from single cells in microfluidic droplets. We also tested hybridization chain reaction (HCR) as an amplification mechanism and found results similar to CHA. In FIG. 14A, error bars denote +/−1 standard deviation of the mean. These experiments were performed as described in "Catalyzed Hairpin Assembly Experiments."

Figure 15A:
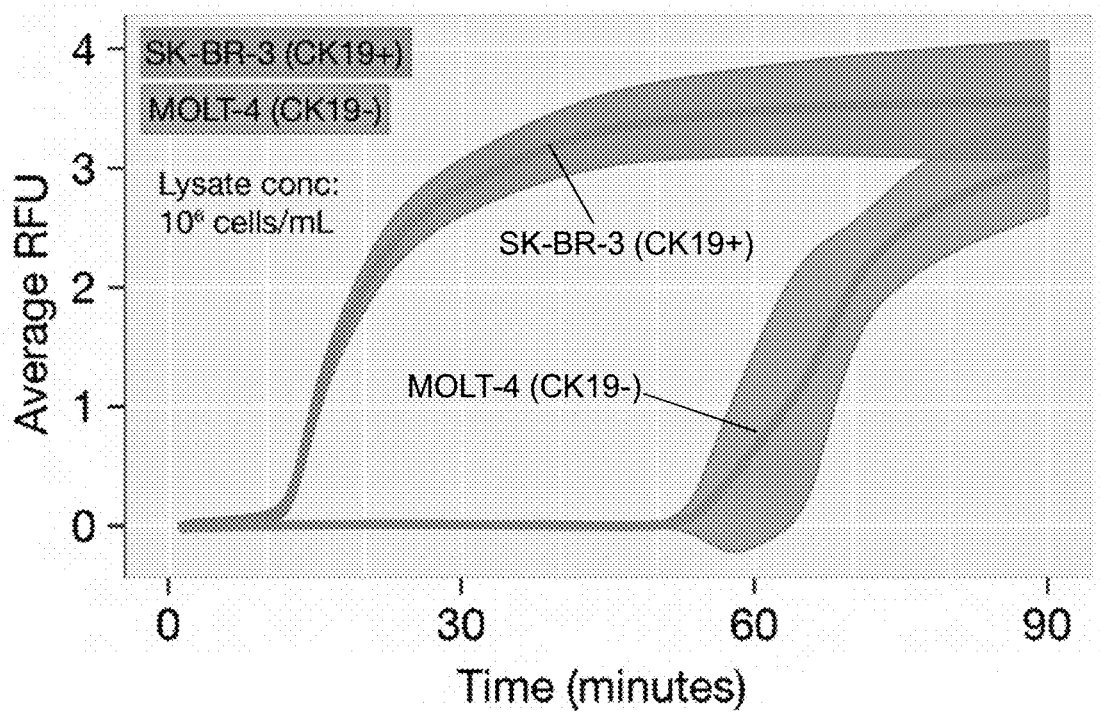
FIGS. 15A and 15B show RT-LAMP amplification of mRNA for the epithelial marker CK19 (KRT19) in CK19+ human breast cancer cells (SK-BR-3) versus CK19-leukocytes (MOLT-4).
Figure 15B:
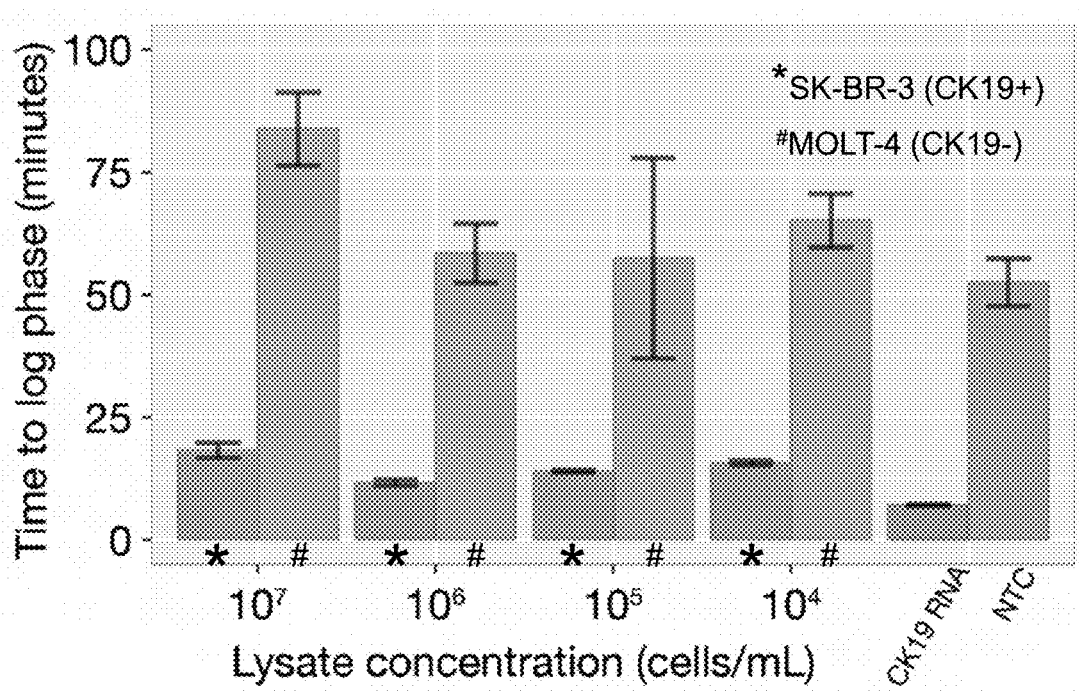

We identified reverse transcriptase loop-mediated isothermal amplification (RT-LAMP) as a robust technique for amplifying transcripts from single cells. LAMP uses six primers and a strand-displacing DNA polymerase to exponentially amplify nucleic acid targets. With RT-LAMP, we've achieved sub-nanomolar detection sensitivity and lysate resistance beyond the target working concentration of $10^6$ cells/ml. We tested RT-LAMP's ability to distinguish between human breast cancer cells (SK-BR-3) and leukocytes (MOLT-4) using primers specific to the epithelial marker Cytokeratin 19 (CK19, KRT19). These experiments revealed a broad (50 minute) detection window with a signal-to-background ratio>150 (FIGS. 15A and 15B). This outstanding signal amplification is more than sufficient to feed into downstream molecular logic gates and detect on microfluidic chips. Furthermore, we determined that CK19 LAMP reliably distinguishes SK-BR-3 and MOLT-4 lysates even at $10^7$ cells/mL, which is equivalent to one cell per 100 pL droplet (FIG. 15B). These experiments show that RT-LAMP on the epithelial marker KRT19 can distinguish between human breast cancer cells (SK-BR-3) and leukocytes (MOLT-4) under conditions equivalent to microdroplet reactions. Error bars denote +/−1 standard deviation of the mean in all experiments. These experiments were performed as described in "Batch RT-LAMP Experiments."

Molecular logic: A CTC detection circuit must integrate the signals from multiple transcripts to perform a CTC classification. DNA logic gates can perform complex molecular logic and computation on nucleic acid inputs. We have designed new logic gates that harness the strand-displacement activity of the LAMP polymerase to drive strand displacement. This new mechanism provides superior kinetics and less signal leakage than traditional random-walk branch migration cascades.

Figure 16:
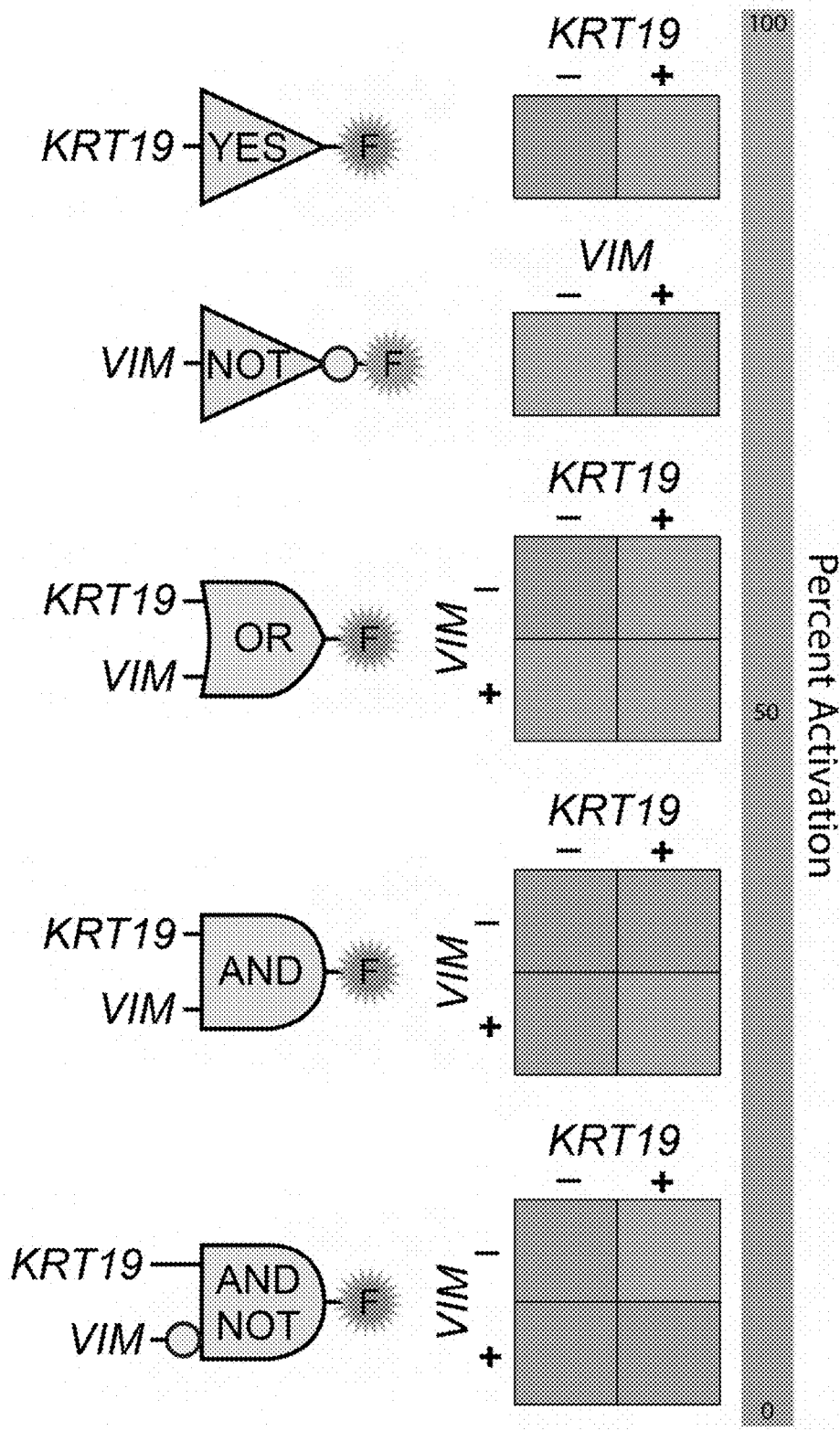
FIG. 16 shows fluorescent detection patterns of LAMP products of the epithelial phenotype marker KRT19 and/or the mesenchymal phenotype marker VIM using polymerase-dependent logic gates employing a YES logical operation, a NOT logical operation, an OR logical operation, an AND logical operation, or an AND-NOT logical operation. The YES logic gate was structured as shown in FIG. 4. The NOT logic gate was structured as shown in FIG. 10. The OR logic gate was structured as shown in FIGS. 7A-7D, with the threshold strand omitted. The AND logic gate was structured as shown in FIGS. 7A-7D. The AND-NOT logic gate was structured as shown in FIGS. 9A-9D.
Figure 18A:
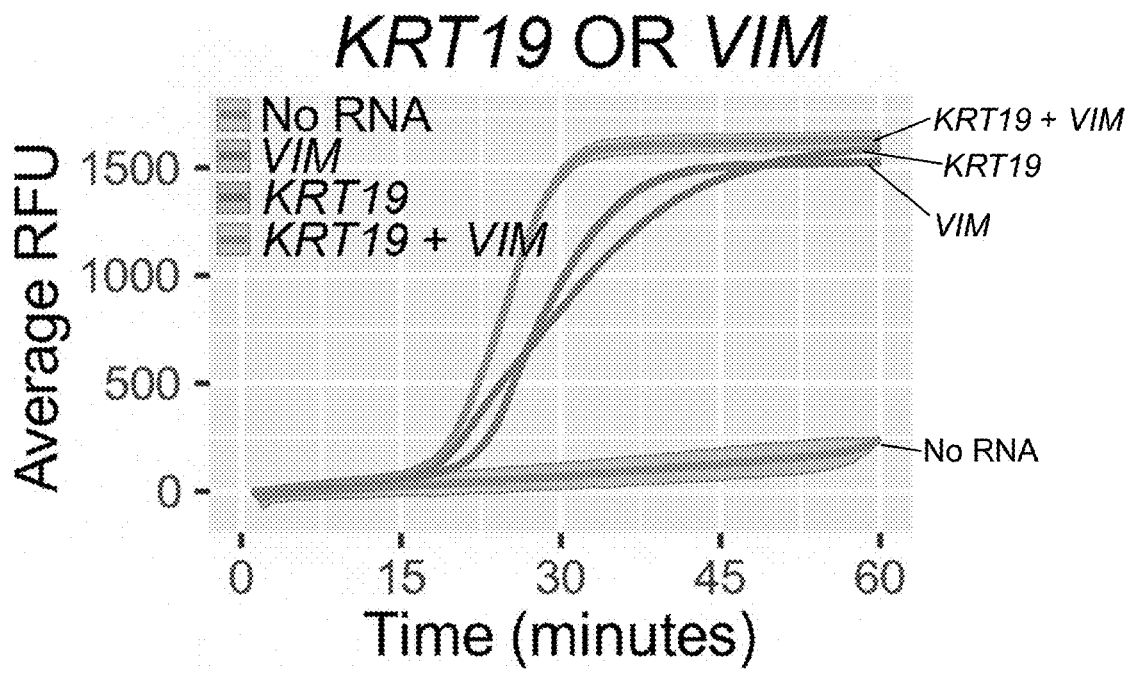
FIGS. 18A and 18B show fluorescent detection of KRT19 and/or VIM RNA using RT-LAMP and an OR logic gate (FIG. 18A) or an AND logic gate (FIG. 18B). The OR and logic gates were both structured as shown in FIGS. 7A-7D except that OR logic gate lacked a threshold strand. Error bars denote +/−1 standard deviation of the mean.
Figure 18B:
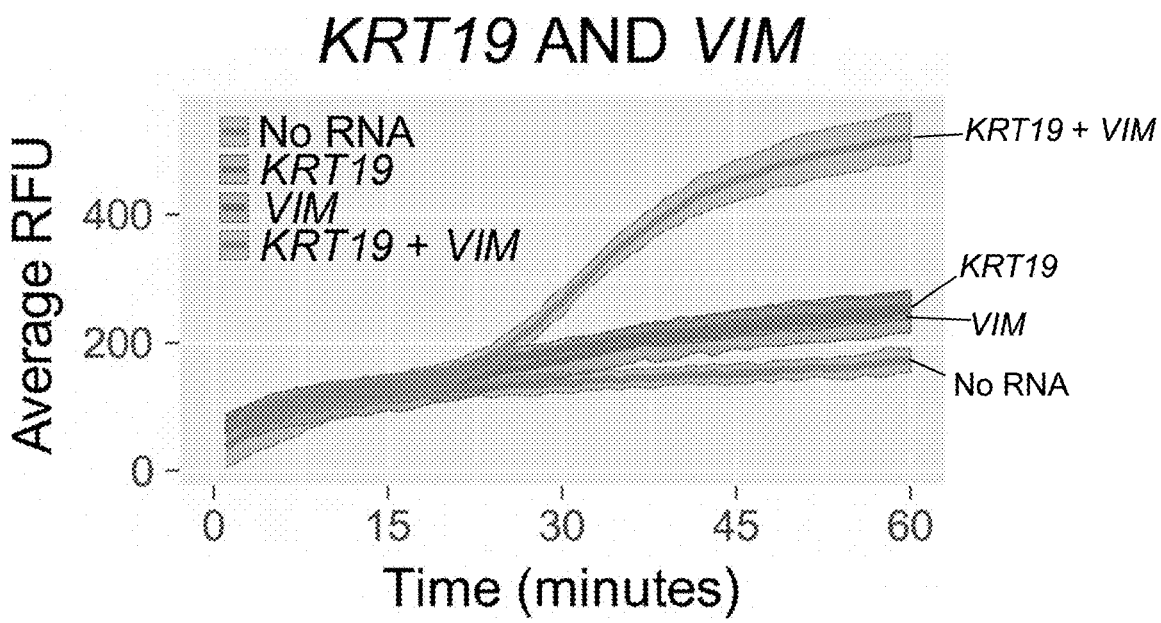
Figure 19A:
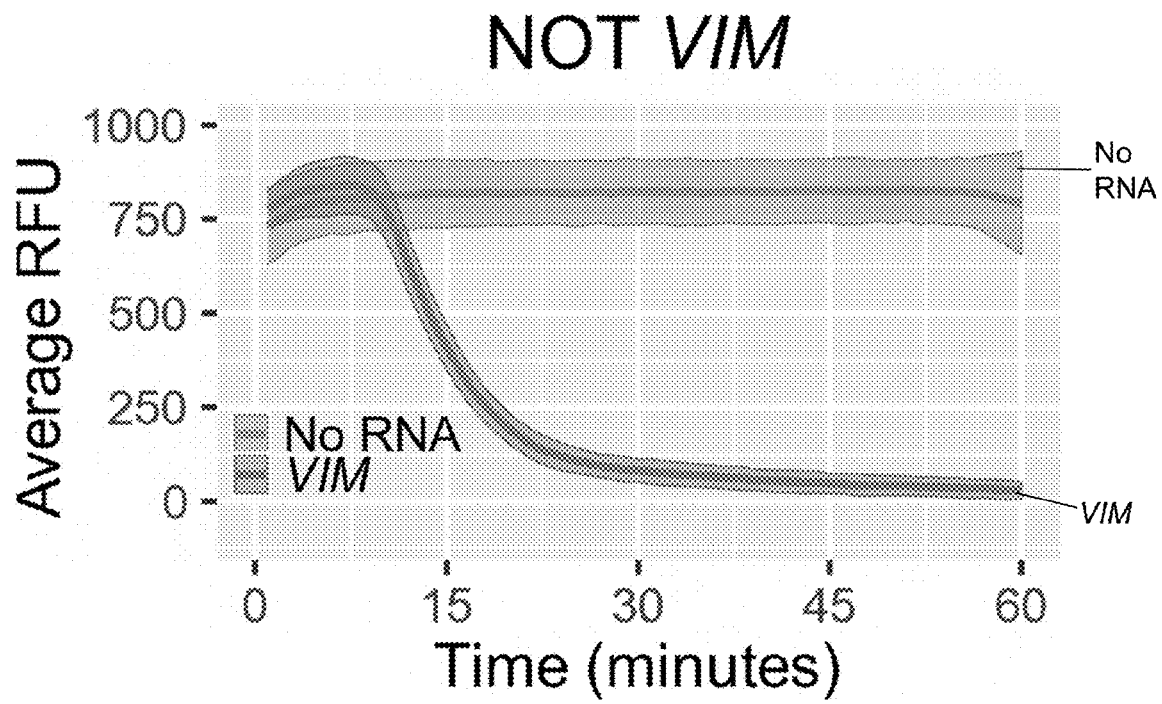
FIGS. 19A and 19B show fluorescent detection of KRT19 and/or VIM RNA using RT-LAMP and a NOT logic gate (FIG. 19A) or an AND-NOT logic gate (FIG. 19B). The NOT gate was structured as shown in FIG. 10, and the AND-NOT gate was structured as shown in FIGS. 9A-9D. Error bars denote +/−1 standard deviation of the mean.
Figure 19B:
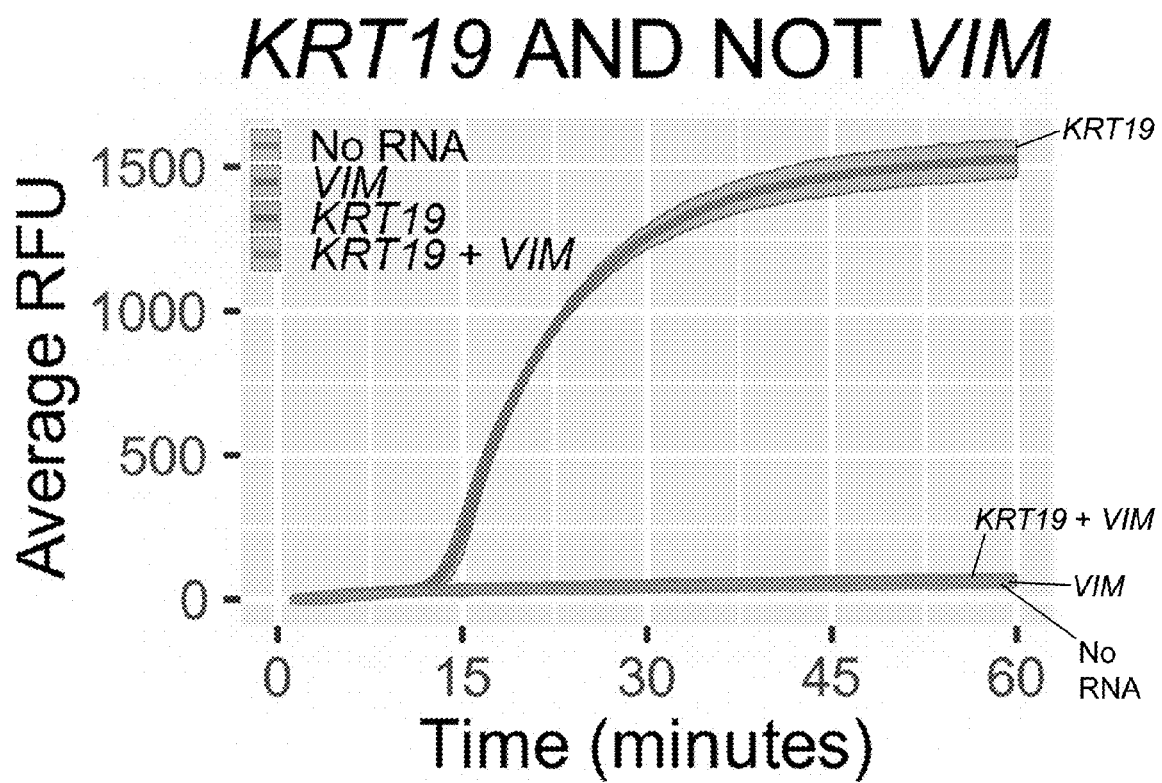

We have designed all fundamental one- and two-input logic gates using the polymerase-driven mechanism (FIGS. 4-11). In theory, any arbitrarily complex logical function could be computed by cascading these fundamental gates. As an initial demonstration, we built a YES gate that detects an epithelial marker (KRT19) (FIG. 4), a NOT gate that detects a mesenchymal marker (VIM) (FIG. 10), an OR gate that recognizes epithelial (KRT19) or mesenchymal (VIM) markers (FIGS. 7A-D), an AND gate that recognizes epithelial (KRT19) and mesenchymal (VIM) markers (FIGS. 7A-7D), and an AND-NOT gate that recognizes epithelial (KRT19) and mesenchymal (VIM) markers (FIGS. 9A-D). These gates are important for identifying CTCs that occupy states along the epithelial-mesenchymal or mesenchymal-epithelial transitions. The experiments on these gates demonstrated a strong and uniform fluorescence signal in the presence of KRT19 and/or VIM consistent with the designed logical operations of the logic gates (FIG. 16). FIG. 16 includes endpoint results from the time traces shown for the NOT gate (FIG. 19A), OR gate (FIG. 18A), AND gate (FIG. 18B), and AND-NOT gate (FIG. 19B). These experiments were performed as described under "AND Logic Gate Experiment with LAMP Inputs," "OR Logic Gate Experiment with LAMP Inputs," "YES Logic Gate Experiment with LAMP Inputs," "NOT Logic Gate Experiment with LAMP Inputs," and "AND-NOT Logic Gate Experiment with LAMP Inputs." Error bars denote +/−1 standard deviation of the mean in all plots.

Figure 17A:
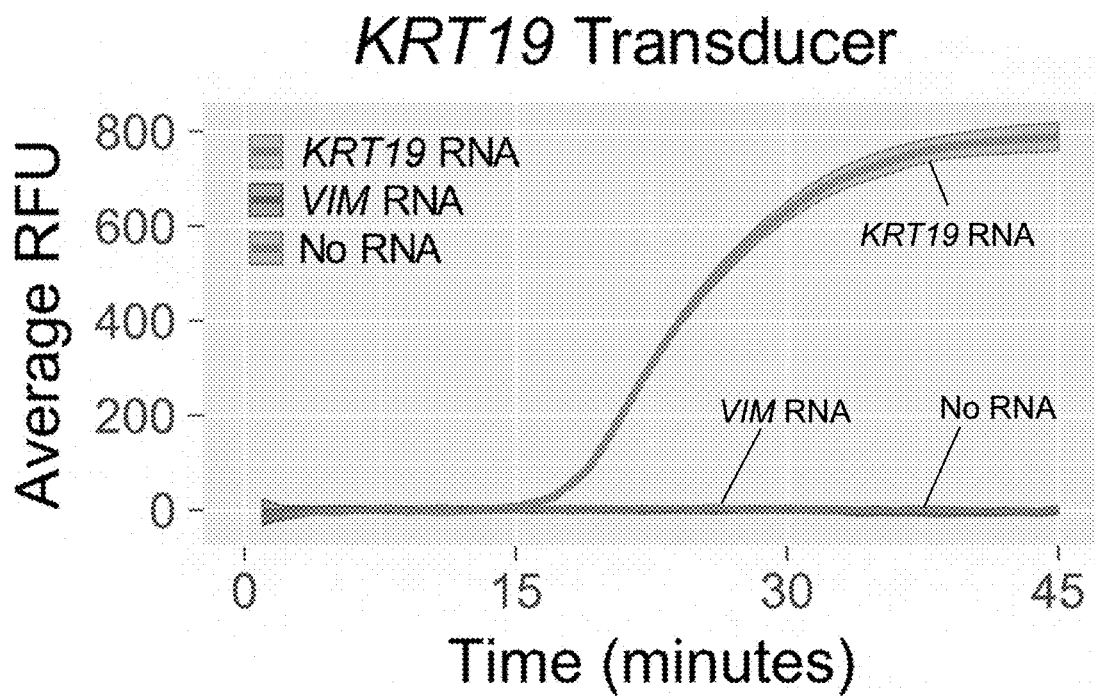
FIGS. 17A and 17B show fluorescent detection of KRT19 RNA (FIG. 17A) or VIM RNA (FIG. 17B) using RT-LAMP with a multiplex primer format and YES nucleic acid logic gates structured as shown in FIG. 4. Error bars denote +/−1 standard deviation of the mean.
Figure 17B:
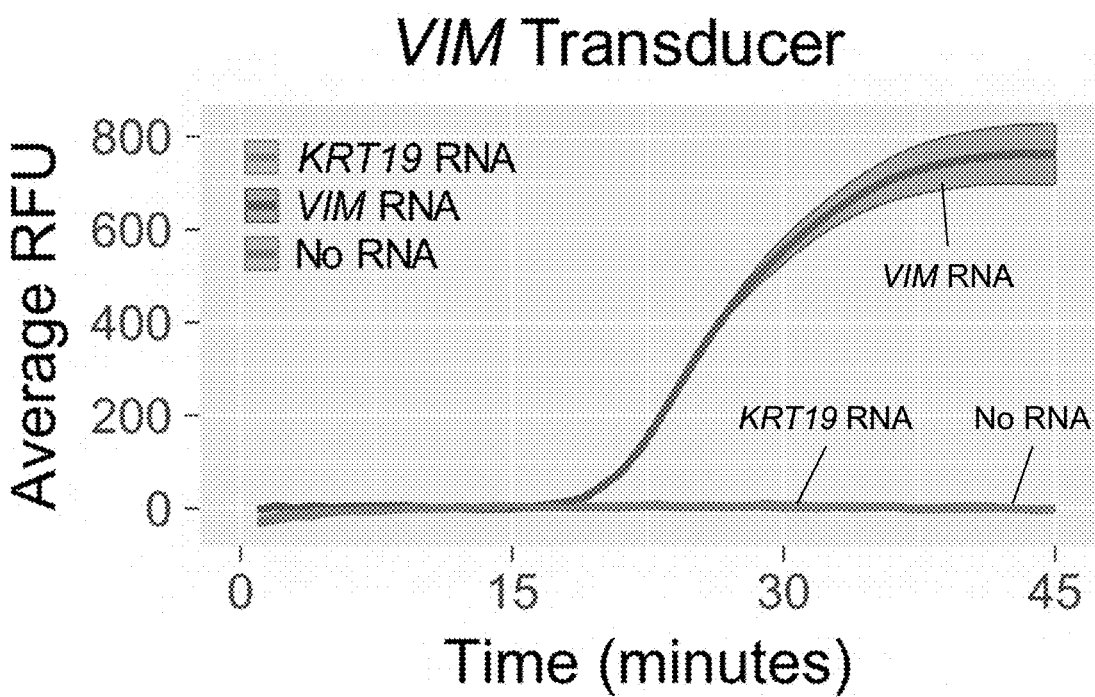

We additionally demonstrated that YES gates can operate orthogonally to detect specific amplification events in a multiplexed LAMP reaction. Experiments were conducted using orthogonal, multiplexed LAMP and YES logic gates recognizing either VIM (FIG. 17B) or KRT19 (FIG. 17A), as described above under "Transducer Orthogonality Experiments." Error bars denote +/−1 standard deviation of the mean.

Ultra-High-Throughput Microfluidic CTC Screening Device

The following examples provide an integrated microfluidic device that monitors the output of the DNA-based logic circuit developed in the experiments outlined above. The experiments demonstrate the ability to miniaturize RT-LAMP reactions in microfluidic droplets and apply this to distinguish phenotypic states of single cells.

Figure 20A:
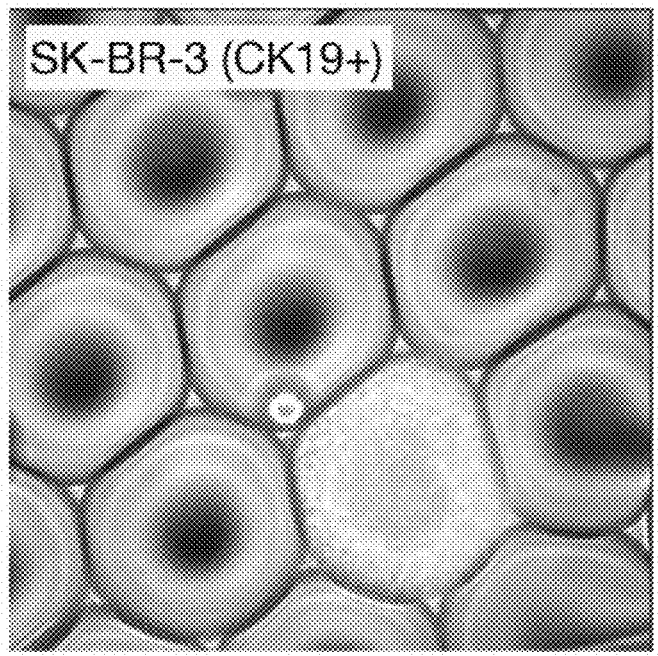
FIGS. 20A and 20B show RT-LAMP amplification of mRNA for the epithelial marker CK19 (KRT19) in CK19+ human breast cancer cells (SK-BR-3) (FIG. 20A) versus CK19− leukocytes (MOLT-4) (FIG. 20B) in aqueous droplets suspended in fluorinated oil, using a dsDNA-specific dye to indicate amplification.
Figure 20B:
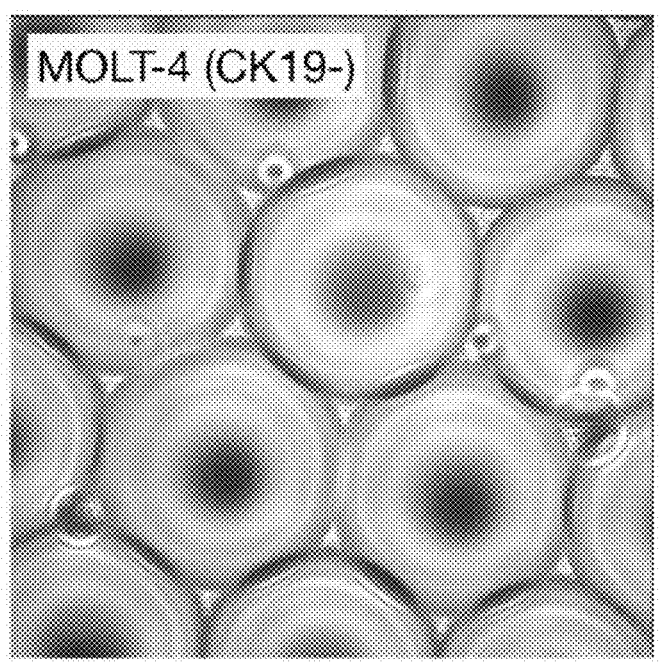

Single-cell analysis in microfluidic droplets: After optimizing LAMP conditions in bulk assays, we scaled them down to a microemulsion format. Single cells were loaded onto a microfluidic device and encapsulated in ~1 nL droplets containing lysis reagents, RT-LAMP reagents, and a dsDNA-specific LAMP indicator. A cell stain (Calcein Red-Orange AM, Invitrogen) was used to verify co-localization of cells and LAMP signal. The droplets were incubated for 20 minutes and imaged using fluorescence microcopy. Leukocytes (MOLT-4) displayed no KRT19 signal above background (FIG. 20B), whereas breast cancer cells (SK-BR-3) displayed strong KRT19 amplification (FIG. 20A). This experiment demonstrates the ability to distinguish cell types using LAMP in microemulsion drops. The experiment was performed as described in "Droplet RT-LAMP Experiments with dsDNA-Specific Reporter."

Figure 21:
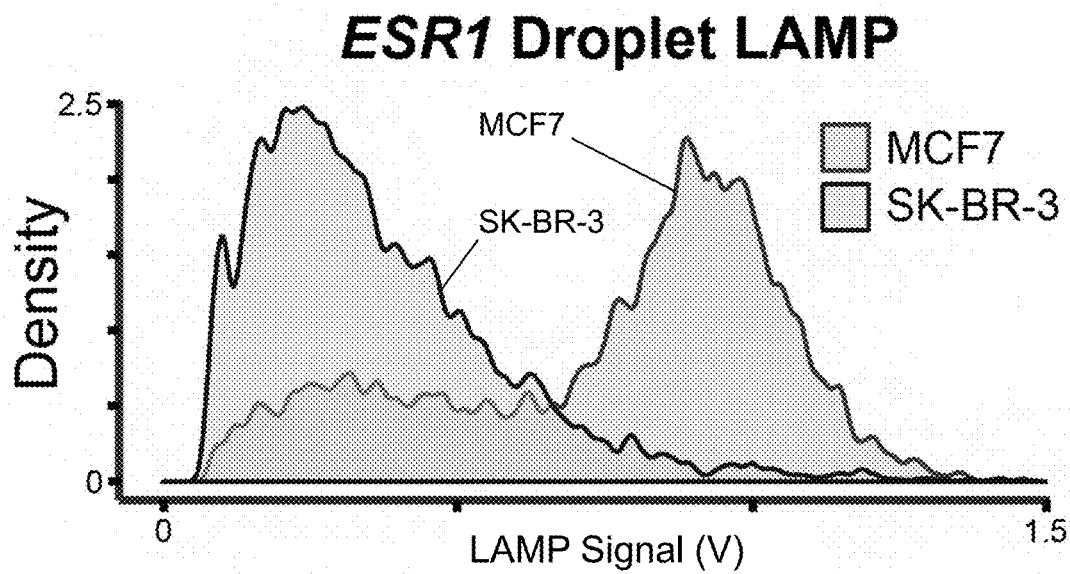
FIG. 21 shows a histogram of RT-LAMP amplification of the Estrogen Receptor (ER) mRNA transcript ESR1 in ER+ human breast cancer cells (MCF7) versus ER− breast cancer cells (SK-BR-3) in aqueous droplets suspended in fluorinated oil, using a dsDNA-specific dye to indicate amplification. Droplets were collected and heated in batch prior to detection.

We further demonstrated single-cell analysis with higher throughput using a fully microfluidic workflow with serial detection. We successfully applied this technique to analyze Estrogen Receptor (ER, ESR1) expression for thousands of MCF7 (ER+) and SK-BR-3 (ER−) cells, as shown in FIG. 21. As expected, a significantly larger portion of the MCF7 cells showed high fluorescence for the LAMP indicator than did the SK-BR-3 cells. This demonstrates that our method can successfully distinguish cells based on their mRNA expression in a high-throughput manner. This experiment was performed as described in "Droplet ESR1 RT-LAMP."

Figure 23A:
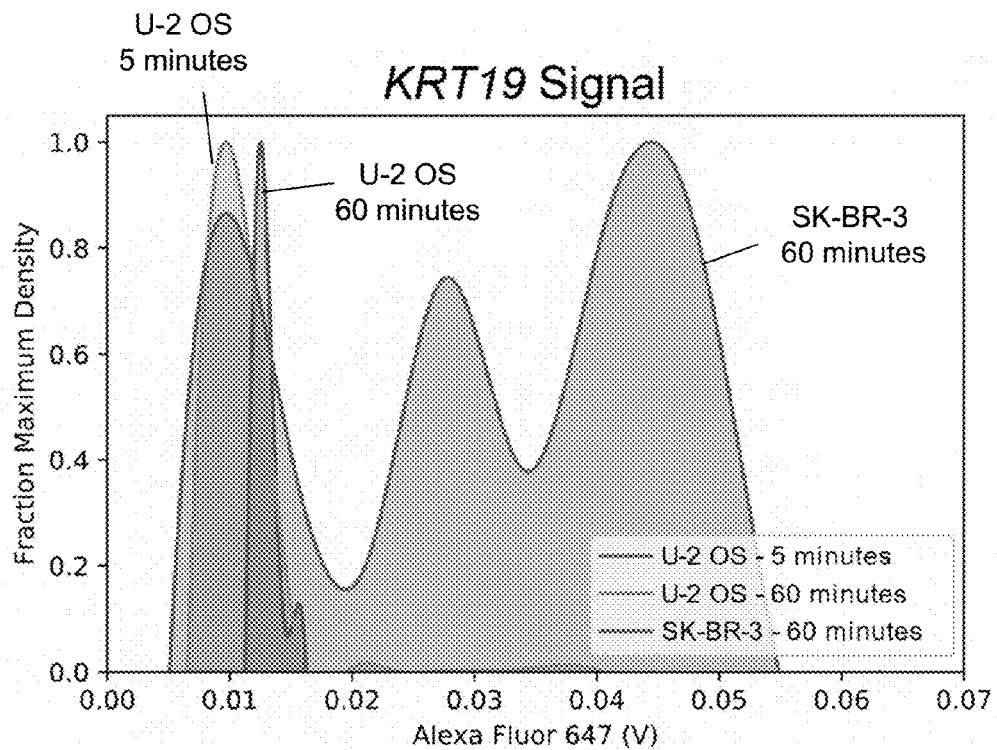
FIGS. 23A and 23B show histograms of RT-LAMP amplification of the epithelial marker CK19 (KRT19) and the mesenchymal marker VIM (VIM) using multiplexed and orthogonal YES logic gates and reporter complexes, where KRT19 amplification activates the Alexa Fluor 647 reporter, and VIM amplification activates the HEX reporter.
Figure 23B:
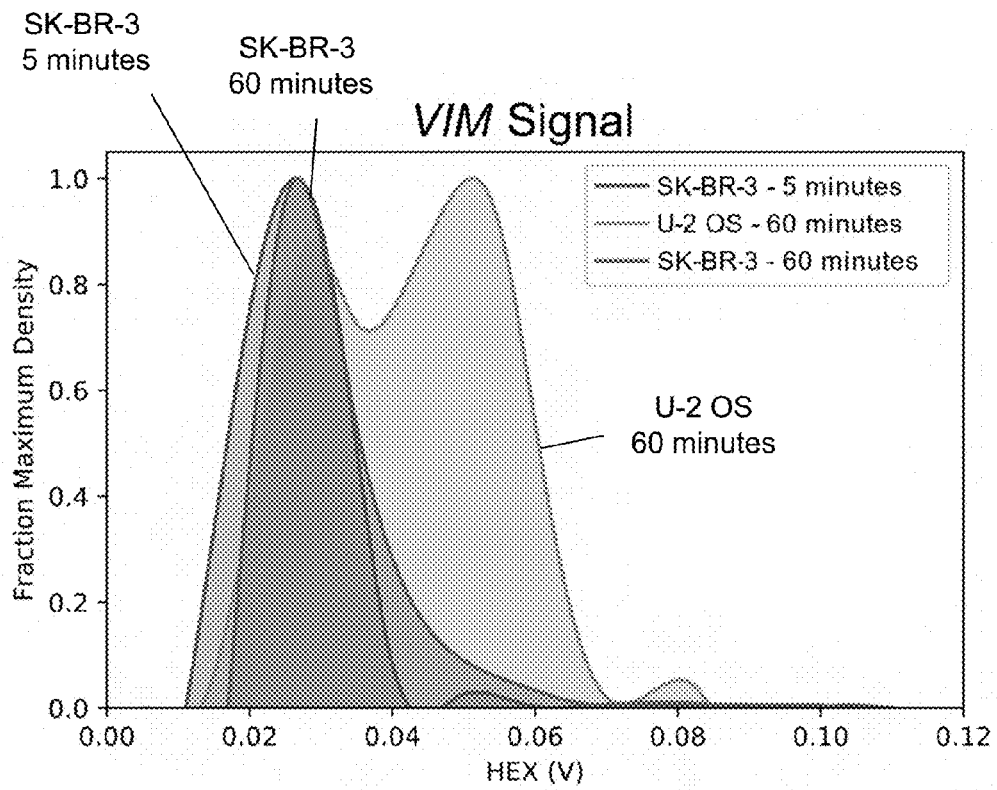

We additionally showed that multiple transcripts can be assayed simultaneously in these droplet assays, as shown in FIGS. 23A and 23B. We performed a multiplexed transducer experiment wherein KRT19 amplification activates an Alexa Fluor 647 reporter, and VIM amplification activates a HEX reporter. We encapsulated SK-BR-3 (CK19+/VIM−) and U-2 OS (CK19−/VIM+) cells into droplets with these transducers and reporters and saw that each cell type only activated its expected reporter. This experiment was performed as described in "Droplet RT-LAMP Experiments with Multiplexed Transducers."

Figure 22:
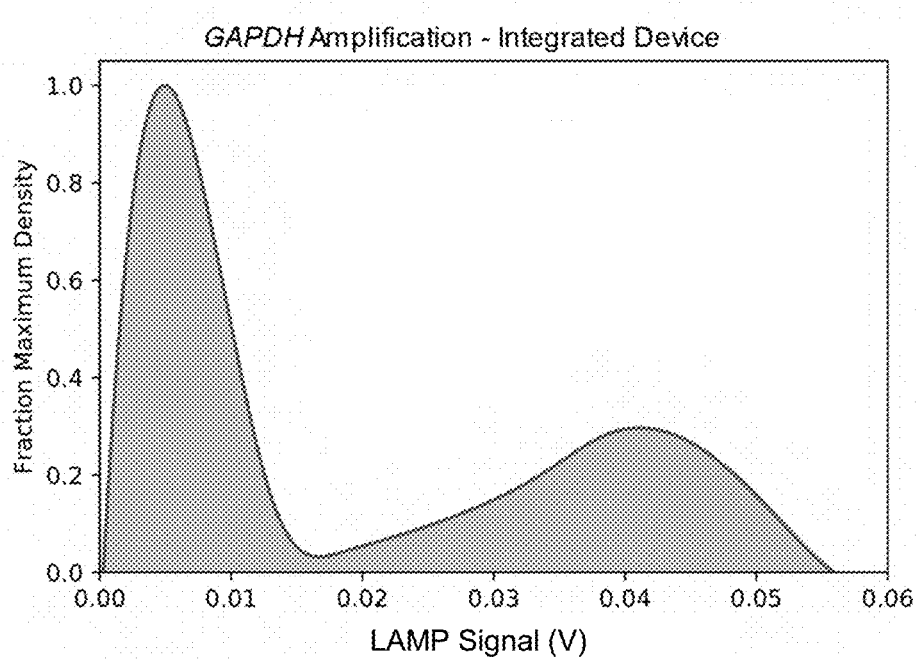
FIG. 22 shows a histogram of RT-LAMP amplification of a glyceraldehyde 3-phosphate dehydrogenase (GAPDH) mRNA transcript in human leukocyte cell line MOLT-4 in aqueous droplets suspended in fluorinated oil, using a dsDNA-dependent dye to indicate amplification. Droplets were generated, incubated, and analyzed in an integrated microfluidic device implementing the entire workflow.

Integrated microfluidic device: We integrated all three microfluidic steps into a continuous workflow that requires no user intervention. This device comprises three modules. The modules: (1) Encapsulate single cells in droplets containing the DNA circuit and amplification reagents; (2) Incubate the reaction for a specified time and temperature; and (3) Detect the circuit output using fluorescence spectroscopy. An exemplary system is shown in FIG. 12. As shown in FIG. 22, we were able to amplify a GAPDH transcript in thousands of MOLT-4 cells using this device. Based on these experiments, a fully automated microfluidic device for analyzing millions of cells per hour can be made.

This experiment was performed as described in "Droplet RT-LAMP with Integrated Device."

Figure 24A:
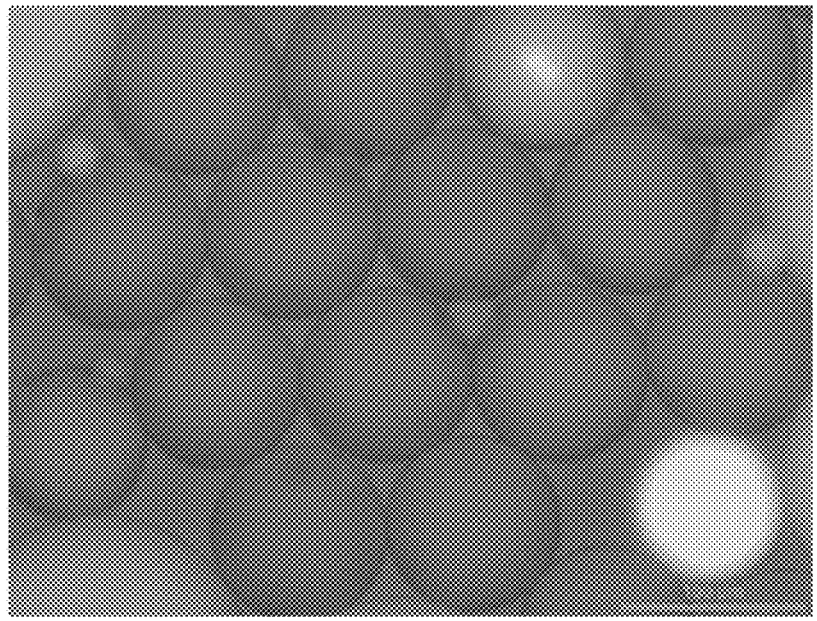
FIGS. 24A and 24B show droplets collected from the waste outlet (FIG. 24A) or sorted outlet (FIG. 24B) of a droplet sorting device discriminating between human ER+ breast cancer line MCF7 and ER− breast cancer line SK-BR-3 based on ESR1 (ER) LAMP amplification.
Figure 24B:
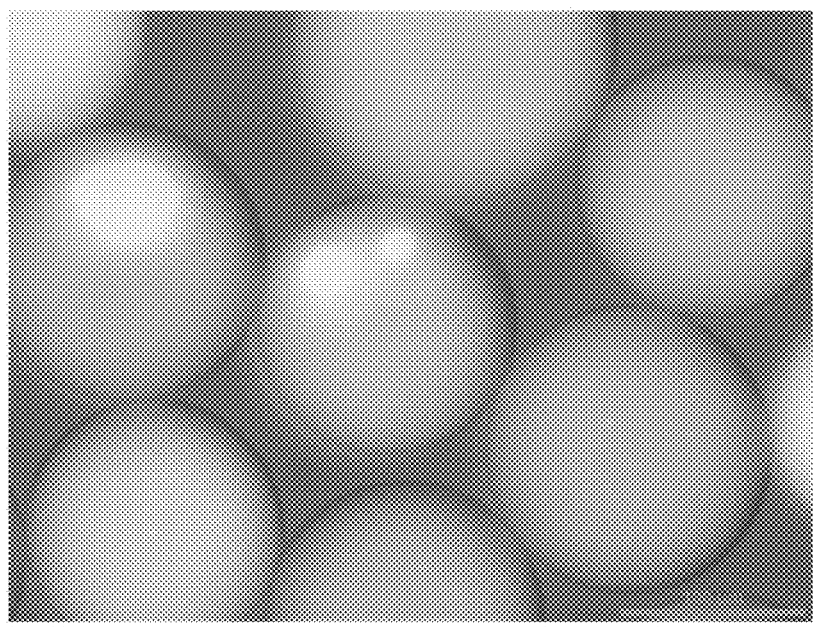

Microfluidic droplet sorting: We employed a dielectrophoretic sorting device to separate two cell types based on expression of an Estrogen Receptor (ER) transcript (ESR1). MCF7 (ER+) and SK-BR-3 (ER−) cells were separately stained, mixed together, then sorted based on RT-LAMP amplification. As shown in FIGS. 24A and 24B, this device successfully enriched green fluorescent droplets in the sorted outlet, which indicates successful ESR1 amplification. This experiment demonstrates our ability to physically separate cell populations based on their transcriptional status. These sorted and unsorted pools could be further analyzed by RNA sequencing, or other assays. This sorting device is depicted in FIG. 13. See also Sciambi and Abate 2015.

Additional logic circuits: The experiments outlined above demonstrate the ability to profile single cells in microfluidic droplets using strand displacement cascades. One of the advantages of the molecular logic circuits is the ability to swap in/out new elements to tailor assays to cancer types or even patients. Logic circuits can be built to profile multiple transcriptional inputs, such as informative molecular marker panels for specific cancer types. The microfluidic device can be used to detect and/or classify low-abundance CTCs in human blood samples.

Figure 25:
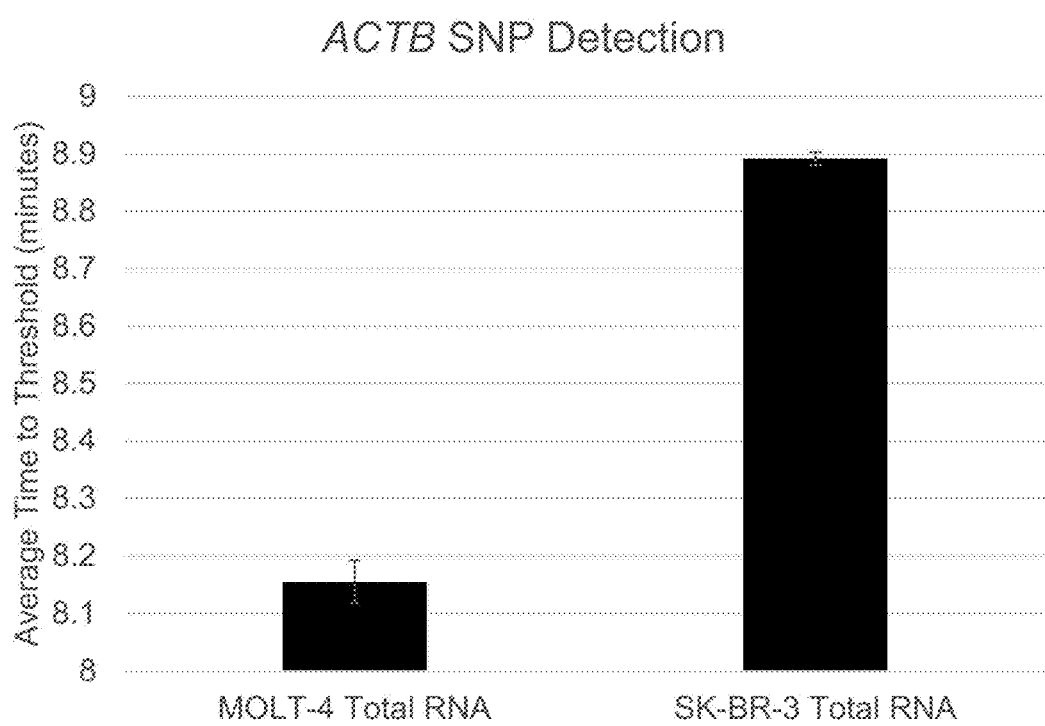
FIG. 25 shows LAMP-based SNP detection in total RNA samples from two cell lines: SK-BR-3, with only WT ACTB transcripts (SEQ ID NO:1), and MOLT-4, which contains an A→C SNP at position 960 of an ACTB transcript (SEQ ID NO:2). Error bars denote +/−1 standard deviation of the mean.

Additional samples and profiling characteristics: The assays and devices described herein can be used on samples other than blood samples. Cells from tissue biopsies, for example, can be dispersed and subjected to nucleic acid profiling as described herein. The profiling can be used to profile any of a number of nucleic acid characteristics and to classify cells in any of a number of formats. Profiling expression patterns of mRNAs and/or miRNAs and detecting or profiling SNPs provide only a few, non-limiting examples. We have demonstrated that LAMP-based SNP detection could be feasible in droplets, by discriminating between MOLT-4 and SK-BR-3 total RNA. MOLT-4 RNA, which contains a SNP in an ACTB transcript, amplified before SK-BR-3 RNA. These results are shown in FIG. 25. Error bars denote +/−1 standard deviation of the mean. This SNP experiment was performed as described in "ACTB SNP-LAMP Detection Experiments."

REFERENCES

Arezi B, McCarthy M, Hogrefe H. Mutant of Moloney murine leukemia virus reverse transcriptase exhibits higher resistance to common RT-qPCR inhibitors. Anal Biochem. 2010 May 15; 400(2):301-3.

Baccouche A, Montagne K, Padirac A, Fujii T, Rondelez Y. Dynamic DNA-toolbox reaction circuits: a walkthrough. Methods. 2014 May 15; 67(2):234-49.

Badolo A, Okado K, Guelbeogo W M, Aonuma H, Bando H, Fukumoto S, Sagnon N, Kanuka H. Development of an allele-specific, loop-mediated, isothermal amplification method (AS-LAMP) to detect the L1014F kdr-w mutation in *Anopheles gambiae* s. 1. Malar J. 2012 Jul. 6; 11:227.

Bendall S C, Nolan G P. From single cells to deep phenotypes in cancer. Nat Biotechnol. 2012 Jul. 10; 30(7):639-47.

Chen Y, Song Y, Wu F, Liu W, Fu B, Feng B, Zhou X. A DNA logic gate based on strand displacement reaction and rolling circle amplification, responding to multiple low-abundance DNA fragment input signals, and its application in detecting miRNAs. Chem Commun (Camb). 2015 Apr. 25; 51(32):6980-3.

Deng W, Xu H, Ding W, Liang H (2014) DNA Logic Gate Based on Metallo-Toehold Strand Displacement. PLoS ONE 9(11): e111650.

Eastburn D J, Sciambi A, Abate A R. Ultrahigh-throughput Mammalian single-cell reverse-transcriptase polymerase chain reaction in microfluidic drops. Anal Chem. 2013 Aug. 20; 85(16):8016-21.

Guo M T, Rotem A, Heyman J A, Weitz D A. Droplet microfluidics for high-throughput biological assays. Lab Chip. 2012 Jun. 21; 12(12):2146-55.

Hedman J, Rådström P. Overcoming inhibition in real-time diagnostic PCR. Methods Mol Biol. 2013; 943:17-48.

Kalisky T, Blainey P, Quake S R. Genomic analysis at the single-cell level. Annu Rev Genet. 2011; 45:431-45.

Kalisky T, Quake S R. Single-cell genomics. Nat Methods. 2011 April; 8(4):311-4.

Levsky J M, Singer R H. Gene expression and the myth of the average cell. Trends Cell Biol. 2003 January; 13(1): 4-6.

Li X, Ding T, Sun L, Mao C. Ultrasensitive DNA detection by cycle isothermal amplification based on nicking endonuclease and its application to logic gates. Biosens Bioelectron. 2011 Dec. 15; 30(1):241-8.

Li W, Yang Y, Yan H, Liu Y. Three-input majority logic gate and multiple input logic circuit based on DNA strand displacement. Nano Lett. 2013 Jun. 12; 13(6):2980-8.

Li W, Zhang F, Yan H, Liu Y. DNA based arithmetic function: a half adder based on DNA strand displacement. Nanoscale. 2016 Feb. 14; 8(6):3775-84.

Mary P, Dauphinot L, Bois N, Potier M C, Studer V, Tabeling P. Analysis of gene expression at the single-cell level using microdroplet-based microfluidic technology. Biomicrofluidics. 2011 June; 5(2):24109.

Massey M, Medintz I L, Ancona M G, Algar W R. Time-Gated FRET and DNA-Based Photonic Molecular Logic Gates: AND, OR, NAND, and NOR. ACS Sens. 2017 Aug. 25; 2(8):1205-1214.

Novak R, Zeng Y, Shuga J, Venugopalan G, Fletcher D A, Smith M T, Mathies R A. Single-cell multiplex gene detection and sequencing with microfluidically generated agarose emulsions. Angew Chem Int Ed Engl. 2011 Jan. 10; 50(2):390-5.

Okamoto A, Tanaka K, Saito I. DNA logic gates. J Am Chem Soc. 2004 Aug. 4; 126(30):9458-63.

Qian L, Winfree E. A simple DNA gate motif for synthesizing large-scale circuits. J R Soc Interface. 2011 Sep. 7; 8(62):1281-97.

Qian L, Winfree E, Bruck J. Neural network computation with DNA strand displacement cascades. Nature. 2011 Jul. 20; 475(7356):368-72.

Ravan H, Amandadi M, Esmaeili-Mahani S. DNA Domino-Based Nanoscale Logic Circuit: A Versatile Strategy for Ultrasensitive Multiplexed Analysis of Nucleic Acids. Anal Chem. 2017 Jun. 6; 89(11):6021-6028.

Sciambi A, Abate A R. Accurate microfluidic sorting of droplets at 30 kHz. Lab Chip. 2015 Oct. 22; 15:47-51.

Sieuwerts A M, Mostert B, Bolt-de Vries J, Peeters D, de Jongh F E, Stouthard J M, Dirix L Y, van Dam P A, Van Galen A, de Weerd V, Kraan J, van der Spoel P, Ramirez-Moreno R, van Deurzen C H, Smid M, Yu J X, Jiang J, Wang Y, Gratama J W, Sleijfer S, Foekens J A, Martens J W. mRNA and microRNA expression profiles in circulating tumor cells and primary tumors of metastatic breast cancer patients. Clin Cancer Res. 2011 Jun. 1; 17(11): 3600-18.

Tanner N A, Zhang Y, Evans T C Jr. Simultaneous multiple target detection in real-time loop-mediated isothermal amplification. Biotechniques. 2012 August; 53(2):81-9.

Teh S Y, Lin R, Hung L H, Lee A P. Droplet microfluidics. Lab Chip. 2008 February; 8(2):198-220.

Thubagere A J, Thachuk C, Berleant J, Johnson R F, Ardelean D A, Cherry K M, Qian L. Compiler-aided systematic construction of large-scale DNA strand displacement circuits using unpurified components. Nat Commun. 2017 Feb. 23; 8:14373.

Vyawahare S, Griffiths A D, Merten C A. Miniaturization and parallelization of biological and chemical assays in microfluidic devices. Chem Biol. 2010 Oct. 29; 17(10): 1052-65.

Wei H, Hu B, Tang S, Zhao G, Guan Y. Repressor logic modules assembled by rolling circle amplification platform to construct a set of logic gates. Sci Rep. 2016 Nov. 21; 6:37477.

White A K, Vanlnsberghe M, Petriv O I, Hamidi M, Sikorski D, Marra M A, Piret J, Aparicio S, Hansen C L. High-throughput microfluidic single-cell RT-qPCR. Proc Natl Acad Sci USA. 2011 Aug. 23; 108(34):13999-4004.

Xu W, Deng R, Wang L, Li J. Multiresponsive rolling circle amplification for DNA logic gates mediated by endonuclease. Anal Chem. 2014 Aug. 5; 86(15):7813-8.

Yang J, Shen L, Ma J, Schlaberg H I, Liu S, Xu J, Zhang C. Fluorescent nanoparticle beacon for logic gate operation regulated by strand displacement. ACS Appl Mater Interfaces. 2013 Jun. 26; 5(12):5392-6.

Yang J, Song Z, Liu S, Zhang Q, Zhang C. Dynamically Arranging Gold Nanoparticles on DNA Origami for Molecular Logic Gates. ACS Appl Mater Interfaces. 2016 Aug. 31; 8(34):22451-6.

Yang B, Zhang X B, Kang L P, Huang Z M, Shen G L, Yu R Q, Tan W. Intelligent layered nanoflare: "lab-on-a-nanoparticle" for multiple DNA logic gate operations and efficient intracellular delivery. Nanoscale. 2014 Aug. 7; 6(15):8990-6.

Yao D, Wang B, Xiao S, Song T, Huang F, Liang H. What Controls the "Off/On Switch" in the Toehold-Mediated Strand Displacement Reaction on DNA Conjugated Gold Nanoparticles? Langmuir. 2015 Jun. 30; 31(25):7055-61.

Yongkiettrakul S, Kampeera J, Chareanchim W, Rattanajak R, Pornthanakasem W, Kiatpathomchai W, Kongkasuriyachai D. Simple detection of single nucleotide polymorphism in *Plasmodium falciparum* by SNP-LAMP assay combined with lateral flow dipstick. Parasitol Int. 2017 February; 66(1):964-971.

Zanoli L M, Spoto G. Isothermal amplification methods for the detection of nucleic acids in microfluidic devices. Biosensors (Basel). 2012 Dec. 27; 3(1):18-43.Zhang C, Yang J, Xu J. Circular DNA logic gates with strand displacement. Langmuir. 2010 Feb. 2; 26(3):1416-9.

Zhang H, Jenkins G, Zou Y, Zhu Z, Yang C J. Massively parallel single-molecule and single-cell emulsion reverse transcription polymerase chain reaction using agarose droplet microfluidics. Anal Chem. 2012 Apr. 17; 84(8): 3599-606.

Zhu J, Zhang L, Dong S, Wang E. Four-way junction-driven DNA strand displacement and its application in building majority logic circuit. ACS Nano. 2013 Nov. 26; 7(11): 10211-7.

Zou C, Wei X, Zhang Z, Liu C, Zhou C, Liu Y. Four-Analog Computation Based on DNA Strand Displacement. ACS Omega 2017 2 (8), 4143-4160.

We claim:

1. A method of profiling a nucleic acid composition of a single cell comprising:
   isolating the single cell in a liquid droplet;
   lysing the single cell in the liquid droplet to release template nucleic acid from the cell;
   amplifying the template nucleic acid in the liquid droplet to generate amplified nucleic acid; and
   detecting the amplified nucleic acid in the liquid droplet, wherein the detecting comprises profiling the amplified nucleic acid by performing a molecular computation with a nucleic acid logic gate.

2. The method of claim 1, wherein the isolating comprises isolating the cell in an aqueous liquid droplet suspended in a water-immiscible medium.

3. The method of claim 1, wherein the isolating comprises isolating the cell in the liquid droplet with a lysis reagent, a DNA polymerase, amplification primers, deoxynucleotide triphosphates, an RNAse inhibitor, the nucleic acid logic gate, and a reporter.

4. A method of profiling a nucleic acid composition of a single cell comprising:
   isolating the single cell in a liquid droplet;
   lysing the single cell in the liquid droplet to release template nucleic acid from the cell;
   amplifying the template nucleic acid in the liquid droplet to generate amplified nucleic acid; and
   detecting the amplified nucleic acid in the liquid droplet, wherein the detecting comprises profiling the amplified nucleic acid by performing a molecular computation with a polymerase-dependent nucleic acid logic gate.

5. The method of claim 4, wherein the polymerase-dependent logic gate comprises an output strand annealed to a gate strand, the logic gate being configured to release the output strand from the gate strand in the presence of an input strand and a DNA polymerase, wherein:
   the output strand anneals to an output-strand annealing portion of the gate strand and does not anneal to an output-strand non-annealing portion of the gate strand, wherein the output-strand annealing portion is closer to a 5' end of the gate strand than the output-strand non-annealing portion;
   the input strand anneals to an input-strand annealing portion of the gate strand and does not anneal to an input-strand non-annealing portion of the gate strand, wherein the input-strand annealing portion is closer to a 3' end of the gate strand than the input-strand non-annealing portion; and
   annealing of the input strand to the gate strand and polymerase-mediated extension of the input strand along the gate strand to form an extended input strand are together necessary and sufficient for release of the output strand from the gate strand.

6. The method of claim 5, wherein the output-strand annealing portion and the input-strand non-annealing portion at least partially overlap, and wherein the input-strand annealing portion and the output-strand non-annealing portion at least partially overlap.

7. The method of claim 5, wherein:
   the output strand comprises a reporter-gate annealing portion that anneals to either a reporter strand or a quencher strand of a reporter gate.

8. The method of claim 7, wherein:
   the output strand further comprises a second-input-strand annealing portion that anneals to a second input strand, wherein the second-input-strand annealing portion is closer to a 3' end of the output strand than the reporter-gate annealing portion.

9. The method of claim 5, wherein the logic gate further comprises a threshold strand configured to anneal to the output strand.

10. The method of claim 5, wherein the input strand is comprised by the amplified nucleic acid.

11. The method of claim 5, wherein the input strand is an output strand from a second logic gate configured to detect a second input strand.

12. The method of claim 5, wherein the output strand is an input strand for a second logic gate.

13. The method of claim 5, wherein the output strand is an input strand for a reporter gate.

14. The method of claim 4, wherein a substantially constant temperature is maintained throughout and between each of the lysing, the amplifying, and the profiling the amplified nucleic acid.

15. The method of claim 1, wherein the detecting comprises detecting a single nucleotide polymorphism in the nucleic acid composition of the single cell.

16. The method of claim 1, wherein the isolating, the lysing, the amplifying, and the detecting all occur in a single, continuous network of channels.

17. The method of claim 1, wherein the isolating occurs prior to the lysing, the lysing occurs prior to the amplifying, and the amplifying occurs prior to the detecting.

18. The method of claim 1, wherein the lysing, the amplifying, and the detecting all occur without diluting the liquid droplet, adding additional reagents to the liquid droplet, and/or removing reagents or liquid from the liquid droplet after the isolating.

19. The method of claim 4, wherein the isolating comprises isolating the cell in the liquid droplet with a lysis reagent, a DNA polymerase, amplification primers, deoxynucleotide triphosphates, an RNAse inhibitor, the nucleic acid logic gate, and a reporter.

20. The method of claim 4, wherein the lysing, the amplifying, and the detecting all occur without diluting the liquid droplet, adding additional reagents to the liquid droplet, and/or removing reagents or liquid from the liquid droplet after the isolating.

* * * * *